US011530399B2

(12) United States Patent
Hagiwara et al.

(10) Patent No.: US 11,530,399 B2
(45) **Date of Patent: *Dec. 20, 2022**

(54) HEMICELLULASE COMPOSITIONS

(71) Applicant: AJINOMOTO CO., INC., Tokyo (JP)

(72) Inventors: Yusuke Hagiwara, Kanagawa (JP); Yasuhiro Mihara, Kanagawa (JP); Tomo Takagi, Kanagawa (JP); Satoshi Nakamura, Kanagawa (JP); Rie Yakushijin, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 54 days.

This patent is subject to a terminal disclaimer.

(21) Appl. No.: 17/085,536

(22) Filed: Oct. 30, 2020

(65) Prior Publication Data

US 2021/0062173 A1 Mar. 4, 2021

Related U.S. Application Data

(63) Continuation of application No. 16/266,542, filed on Feb. 4, 2019, now Pat. No. 10,851,361, which is a continuation of application No. PCT/JP2017/028415, filed on Aug. 4, 2017.

(30) Foreign Application Priority Data

Aug. 5, 2016 (JP) ............................ JP2016-154514

(51) Int. Cl.

| | |
|---|---|
| ***C12N 9/24*** | (2006.01) |
| ***C12N 1/20*** | (2006.01) |
| ***A23K 20/189*** | (2016.01) |
| ***A23K 10/14*** | (2016.01) |
| ***C12N 15/09*** | (2006.01) |
| ***C12P 19/02*** | (2006.01) |
| ***C13K 1/02*** | (2006.01) |

(52) U.S. Cl.

CPC ............ *C12N 9/2482* (2013.01); *A23K 10/14* (2016.05); *A23K 20/189* (2016.05); *C12N 1/20* (2013.01); *C12N 15/09* (2013.01); *C12P 19/02* (2013.01); *C13K 1/02* (2013.01)

(58) Field of Classification Search

None

See application file for complete search history.

(56) References Cited

U.S. PATENT DOCUMENTS

| | | | | |
|---|---|---|---|---|
| 8,956,842 | B2 | 2/2015 | Hwang et al. | |
| 10,851,361 | B2 * | 12/2020 | Hagiwara | C12N 15/09 |
| 2016/0150807 | A1 | 6/2016 | Krogh et al. | |
| 2019/0153416 | A1 | 5/2019 | Hagiwara et al. | |

FOREIGN PATENT DOCUMENTS

| | | | |
|---|---|---|---|
| KR | 10-1018790 | B1 | 3/2011 |
| WO | WO03/106654 | A2 | 12/2003 |
| WO | WO2008/037757 | A1 | 4/2008 |
| WO | WO2014/020142 | A1 | 2/2014 |
| WO | WO2014/020143 | A2 | 2/2014 |
| WO | WO2016/005522 | A1 | 1/2016 |

OTHER PUBLICATIONS

Accession A0A069DJA1. Oct. 1, 2014 (Year: 2014).*
Accession A0A090Y644. Nov. 26, 2014 (Year: 2014).*
Accession A0A0B2FJW6. Mar. 4, 2015 (Year: 2015).*
Database GenBank [www.ncbi.nlm.gov/Protein/72708984], Accession No. KHF37231.1, Nov. 26, 2014 [retrieved Oct. 2017].
Database GenBank [www.ncbi.nlm.nih.gov/Protein/ACT02895.1] Accession No. ACT02895.1, Dec. 11, 2013 [retrieved Oct. 17, 2017].
Database GenBank [www.ncbi.nlm.nih.gov/Protein/SDZ01154.1] Accession No. SDZ01154.1, Oct. 22, 2016 [retrieval date Oct. 17, 2017].
Database GenBank [www.ncbi.nlm.nih.gov/Protein/GAK42763.1] Accession No. GAK42763.1, Apr. 10, 2015 [retrieval date Oct. 17, 2017].
Database GenBank [www.ncbi.nlm.nih.gov/Protein/AGN37958.1] Accession No. AGN37958.1, Nov. 16, 2015 [retrieval date Oct. 17, 2017].
Padilha, I. Q. M., et al., "A glucuronoxylan-specific xylanase from a new Paenibacillus favisporus strain isolated from tropical soil of Brazil," Int. Microbiol. 2014;17:175-184.
Rose, D. J., et al., "A Method for the Determination of Soluble Arabinoxylan Released from Insoluble Substrates by Xylanases," Food Anal. Methods 2011;4:66-72.
Sakka, M., et al., "Characterization of Paenibacillus curdlanolyticus B-6 Xyn10D, a Xylanase That Contains a Family 3 Carbohydrate-Binding Module," Appl. Environmen. Microbiol. 2011;77(12):4260-4263.
International Search Report for PCT Patent App. No. PCT/JP2017/028415 (dated Oct. 31, 2017).
International Preliminary Report on Patentability for PCT Patent App. No. PCT/JP2017/028415 (dated Feb. 5, 2019).
Beauchemin, K. A., et al., "A rationale for the development of feed enzyme products for ruminants," Canadian Journal of Animal Science 2004;84(1):23-36.
Chica, R. A., et al., "Semi-rational approaches to engineering enzyme activity: combining the benefits of directed evolution and rational design," Current Opinion in Biotechnology 2005;16:378-384.
Singh, R. K., et al., "Protein Engineering Approaches in the Post-Genomic Era," Current Protein and Peptide Science 2017;18:1-11.
Yang, W., et al., "A novel bifunctional GH51 exo-a-L-arabinofuranosidase/endo-xylanase from *Alicyclobacillus* sp. A4 with significant biomass-degrading capacity," Biotechnol. Biofuels 2015;8:197 (pp. 1-11).

(Continued)

*Primary Examiner* — Christian L Fronda
(74) *Attorney, Agent, or Firm* — Cermak Nakajima & McGowan LLP; Shelly Guest Cermak

(57) ABSTRACT

Hemicellulase that degrades corn non-starch polysaccharides ("NSP"), DNA encoding the same, and a method of using the hemicellulase and its DNA are provided. Proteins having hemicellulase activity such as Xyn5A, Xyn10B, Xyn11A, Xyn30A, and Xyn43A are described.

29 Claims, 7 Drawing Sheets

Specification includes a Sequence Listing.

(56) References Cited

OTHER PUBLICATIONS

Accession BCK91338, Mar. 10, 2016, pp. 1-2.
Li, R., et al., "Molecular cloning and characterization of multidomain xylanase from manure library," World J. Microbiol. Biotechnol. 2009;25:2071-2078.
Extended European Search Report for European Patent App. No. 17837098.7 (dated Aug. 20, 2020).

* cited by examiner

HEMICELLULASE COMPOSITIONS

This application is a Continuation of, and claims priority under 35 U.S.C. § 120 to, U.S. patent application Ser. No. 16/266,542, filed Feb. 4, 2019, now allowed, which was a Continuation of, and claimed priority under 35 U.S.C. § 120 to, International Application No. PCT/JP2017/028415, filed Aug. 4, 2017, and claimed priority therethrough under 35 U.S.C. § 119 to Japanese Patent Application No. 2016-154514, filed Aug. 5, 2016, the entireties of which are incorporated by reference herein. Also, the Sequence Listing filed electronically herewith is hereby incorporated by reference (File name: 2020-10-30T_US-590C_Seq_List; File Size: 100 KB; Date recorded: Oct. 30, 2020).

BACKGROUND OF THE INVENTION

Field of the Invention

The present invention relates to a hemicellulase, DNA encoding it, and methods of using them.

Brief Description of the Related Art

Recently, the production of biofuels utilizing the energy provided by biomass, such as cereals, has become of interest. Furthermore, effective use of byproducts of these processes is necessary from the viewpoint of effectiveness and problems such as competition with foods. Examples of such byproducts can include dried distiller grains with solubles, also called "DDGS". DDGS is obtained by ethanol fermentation using starch of a cereal as the carbon source, adding soluble substances that are present in the fermentation broth other than ethanol to the residue after the distillation of ethanol, and drying the mixture. Since the typical chosen cereal is corn, DDGS can also be referred to as corn distillers grain. Since DDGS contains abundant proteins and lipids, it is used as a raw material in mixed feeds. However, saccharides in DDGS mainly are non-starch polysaccharides ("NSP"), also referred to as dietary fiber, such as cellulose and hemicellulose, and hence, utilization of DDGS is restricted. The term "hemicellulose" collectively can refer to polysaccharides that can be extracted from plant tissues with alkali, and includes xylan, arabinoxylan, xyloglucan, glucomannan, etc.

Regarding degradation of hemicellulose, for example, Rose et al. (Food Anal. Methods, 4:66-72 (2011)) describes solubilization of insoluble arabinoxylan by two kinds of xylanases produced by *Aspergillus oryzae*, which belong to Glucoside Hydrolase (GH) families 10 and 11, respectively. While these xylanases show an activity against oat bran and wheat bran, the activity thereof against corn bran is only about 1/100 of that against oat bran or wheat bran.

As xylanases solubilizing arabinoxylan from corn NSP, WO2014/020142 describes xylanase derived from *Fusarium verticillioides*, and WO2014/020143 describes xylanase derived from *Aspergillus clavatus*.

As enzymes releasing monosaccharides from corn NSP, US2016-0150807A describes alpha-xylosidase derived from *Bacteroides ovatus*.

There are many reports about xylanases produced by *Paenibacillus* bacteria. For example, WO2008/037757 describes xylanase derived from *P. pabuli*. While this xylanase was confirmed to show an insoluble arabinoxylan degradation activity against NSP of wheat and barley, it is unknown whether it shows an activity against corn NSP.

Sakka et al. (Appl. Environ. Microbiol., 77(12):4260-4263 (2011)) describes that 3CBM (3 carbohydrate-binding module) of xylanase derived from *P. curdlanolyticus* contributes degradation of insoluble arabinoxylan.

SUMMARY OF THE INVENTION

It is as aspect of the present invention to provide a hemicellulase, specifically a hemicellulase that can degrade corn NSP, DNA encoding it, and methods using both. Novel hemicellulases are described that can degrade corn NSP from *Paenibacillus* bacteria.

It is an aspect of the present invention to provide a protein selected from the group consisting of: (A1) a protein comprising the amino acid sequence of positions 1 to 535 of SEQ ID NO: 4, positions 1 to 536 of SEQ ID NO: 26, positions 1 to 536 of SEQ ID NO: 28, or positions 1 to 536 of SEQ ID NO: 30, wherein said protein has hemicellulase activity; (A2) a protein comprising the amino acid sequence of positions 1 to 535 of SEQ ID NO: 4, positions 1 to 536 of SEQ ID NO: 26, positions 1 to 536 of SEQ ID NO: 28, or positions 1 to 536 of SEQ ID NO: 30, but which includes substitution, deletion, insertion, and/or addition of 1 to 10 amino acid residues, wherein said protein has hemicellulase activity; (A3) a protein comprising an amino acid sequence showing an identity of 90% or higher to the amino acid sequence of positions 1 to 535 of SEQ ID NO: 4, positions 1 to 536 of SEQ ID NO: 26, positions 1 to 536 of SEQ ID NO: 28, or positions 1 to 536 of SEQ ID NO: 30, wherein said protein has hemicellulase activity; (B1) a protein comprising the amino acid sequence of positions 1 to 448 of SEQ ID NO: 6, wherein said protein has hemicellulase activity; (B2) a protein comprising the amino acid sequence of positions 1 to 448 of SEQ ID NO: 6, but which includes substitution, deletion, insertion, and/or addition of 1 to 10 amino acid residues, wherein said protein has hemicellulase activity; (B3) a protein comprising an amino acid sequence showing an identity of 90% or higher to the amino acid sequence of positions 1 to 448 of SEQ ID NO: 6, wherein said protein has hemicellulase activity; (C1) a protein comprising the amino acid sequence of positions 1 to 183 of SEQ ID NO: 9, wherein said protein has hemicellulase activity; (C2) a protein comprising the amino acid sequence of positions 1 to 183 of SEQ ID NO: 9, but which includes substitution, deletion, insertion, and/or addition of 1 to 10 amino acid residues, wherein said protein has hemicellulase activity; (C3) a protein comprising an amino acid sequence showing an identity of 90% or higher to the amino acid sequence of positions 1 to 183 of SEQ ID NO: 9, wherein said protein has hemicellulase activity; (D1) a protein comprising the amino acid sequence of positions 1 to 527 of SEQ ID NO: 12, positions 1 to 529 of SEQ ID NO: 32, or positions 1 to 390 of SEQ ID NO: 34, wherein said protein has hemicellulase activity; (D2) a protein comprising the amino acid sequence of positions 1 to 527 of SEQ ID NO: 12, positions 1 to 529 of SEQ ID NO: 32, or positions 1 to 390 of SEQ ID NO: 34, but which includes substitution, deletion, insertion, and/or addition of 1 to 10 amino acid residues, wherein said protein has hemicellulase activity; (D3) a protein comprising an amino acid sequence showing an identity of 90% or higher to the amino acid sequence of positions 1 to 527 of SEQ ID NO: 12, positions 1 to 529 of SEQ ID NO: 32, or positions 1 to 390 of SEQ ID NO: 34, wherein said protein has hemicellulase activity; (E1) a protein comprising the amino acid sequence of positions 1 to 608 of SEQ ID NO: 14, wherein said protein has hemicellulase activity; (E2) a protein comprising the amino acid sequence of positions 1 to 608 of SEQ ID NO: 14, but which includes substitution, deletion, insertion, and/or addition of 1 to 10 amino acid residues, wherein said protein has hemicellulase activity; and (E3) a protein comprising an amino acid sequence showing an identity of 90% or higher to the amino acid sequence of positions 1 to 608 of SEQ ID NO: 14, wherein said protein has hemicellulase activity.

It is a further aspect of the present invention to provide the protein as described above, wherein the protein is selected from the group consisting of (A1), (A2), (A3), (B1), (B2), (B3), (C1), (C2), (C3), (D1), (D2), and (D3), and wherein said protein has beta-1,4-xylanase activity.

It is a further aspect of the present invention to provide the protein as described above, wherein the proteins of (A2) and (A3) comprise the amino acid sequence of positions 218 to 239 of SEQ ID NO: 4.

It is a further aspect of the present invention to provide the protein as described above, wherein the protein is selected from the group consisting of (E1), (E2), and (E3), and wherein said protein has alpha-L-arabinofuranosidase activity.

It is a further aspect of the present invention to provide a hemicellulase preparation comprising at least one protein as described above.

It is a further aspect of the present invention to provide the hemicellulase preparation as described above, comprising at least two of said proteins.

It is a further aspect of the present invention to provide the hemicellulase preparation as described above, further comprising a protein selected from the group consisting of: (F1) a protein comprising the amino acid sequence of positions 1 to 469 of SEQ ID NO: 36, wherein said protein has a property of enhancing hemicellulase activity; (F2) a protein comprising the amino acid sequence of positions 1 to 469 of SEQ ID NO: 36, but which includes substitution, deletion, insertion, and/or addition of 1 to 10 amino acid residues, wherein said protein has a property of enhancing hemicellulase activity; and (F3) a protein comprising an amino acid sequence showing an identity of 90% or higher to the amino acid sequence of positions 1 to 469 of SEQ ID NO: 36, wherein said protein has a property of enhancing hemicellulase activity.

It is a further aspect of the present invention to provide the hemicellulase preparation as described above, comprising a protein selected from the group consisting of (A1), (A2), (A3), and combinations thereof.

It is a further aspect of the present invention to provide a DNA encoding the protein as described above.

It is a further aspect of the present invention to provide a vector containing the DNA as described above.

It is a further aspect of the present invention to provide a host having enhanced expression of the DNA as described above.

It is a further aspect of the present invention to provide the host as described above, which is a bacterium or a fungus.

It is a further aspect of the present invention to provide a method for producing a saccharification product, the method comprising: treating a hemicellulosic substrate with the protein as described above.

It is a further aspect of the present invention to provide the method as described above, wherein the hemicellulosic substrate is a biomass resource.

It is a further aspect of the present invention to provide an animal feed additive comprising at least one protein as described above.

It is a further aspect of the present invention to provide the animal feed additive as described above, further containing a protein selected from the group consisting of: (F1) a protein comprising the amino acid sequence of positions 1 to 469 of SEQ ID NO: 36, wherein said protein has a property of enhancing hemicellulase activity; (F2) a protein comprising the amino acid sequence of positions 1 to 469 of SEQ ID NO: 36, but which includes substitution, deletion, insertion, and/or addition of 1 to 10 amino acid residues, wherein said protein has a property of enhancing hemicellulase activity; and (F3) a protein comprising an amino acid sequence showing an identity of 90% or higher to the amino acid sequence of positions 1 to 469 of SEQ ID NO: 36, wherein said protein has a property of enhancing hemicellulase activity.

It is a further aspect of the present invention to provide an animal feed comprising at least one protein as described above.

It is a further aspect of the present invention to provide the animal feed as described above, further containing a protein selected from the group consisting of: (F1) a protein comprising the amino acid sequence of positions 1 to 469 of SEQ ID NO: 36, wherein said protein has a property of enhancing hemicellulase activity; (F2) a protein comprising the amino acid sequence of positions 1 to 469 of SEQ ID NO: 36, but which includes substitution, deletion, insertion, and/or addition of 1 to 10 amino acid residues, wherein said protein has a property of enhancing hemicellulase activity; and (F3) a protein comprising an amino acid sequence showing an identity of 90% or higher to the amino acid sequence of positions 1 to 469 of SEQ ID NO: 36, wherein said protein has a property of enhancing hemicellulase activity.

It is a further aspect of the present invention to provide *Paenibacillus* sp. AJ111229 strain (NITE BP-02241).

DETAILED DESCRIPTION OF EXEMPLARY EMBODIMENTS

<1> Hemicellulase and DNA Encoding it

Figure 1:
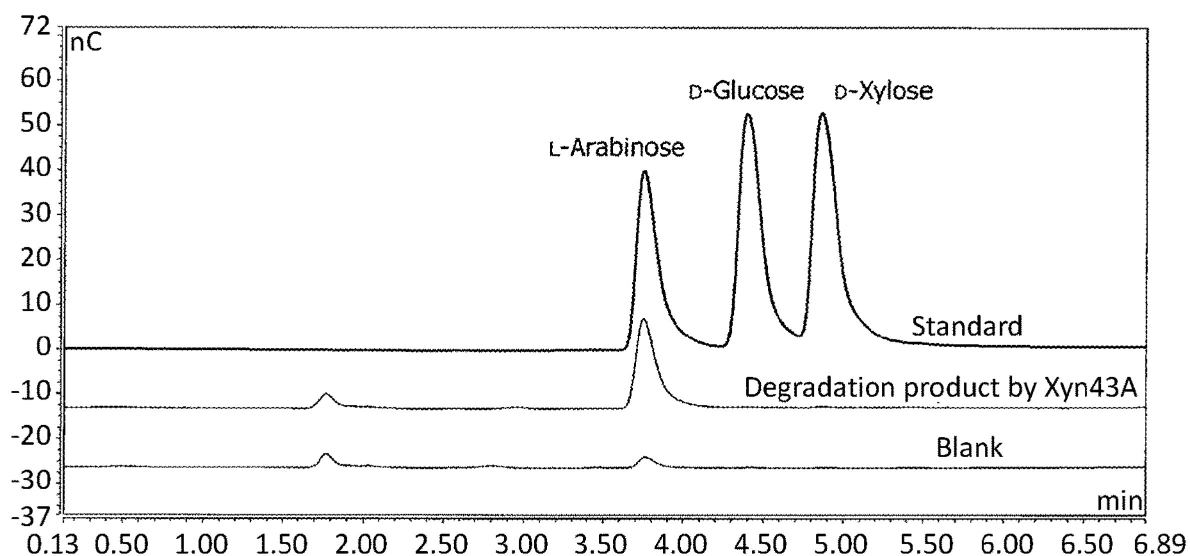
FIG. 1 shows a chromatogram of a reaction mixture of wheat arabinoxylan degradation by Xyn43A.

The present invention provides a hemicellulase and DNA encoding it. This hemicellulase can also be referred to as "hemicellulase as described herein". This DNA can also be referred to as "DNA as described herein".

The term "hemicellulase" collectively can refer to enzymes hydrolyzing hemicellulose (EC 3.2.1.8 or EC 3.2.1.89). Hemicellulose is a polysaccharide that can be extracted from plant tissues with alkali. Major examples of hemicellulose can include xylan, arabinoxylan, xyloglucan, glucomannan, etc. An activity of hydrolyzing hemicellulose can also be referred to as "hemicellulase activity".

The hemicellulase as described herein may have at least an activity of degrading xylan (xylanase activity) and/or an activity of degrading arabinoxylan (arabinoxylanase activity). A hemicellulase having xylanase activity and a hemicellulase having arabinoxylanase activity can also be referred to as "xylanase" (EC 3.2.1.8) and "arabinoxylanase", respectively. Hence, the hemicellulase as described herein may be xylanase (EC 3.2.1.8) or arabinoxylanase. The hemicellulase as described herein may have, specifically, an activity of cleaving beta-1,4-glycoside bond between xylose residues forming a backbone of xylan or arabinoxylan (beta-1,4-xylanase activity). A hemicellulase having beta-1,4-xylanase activity can also be referred to as "beta-1,4-xylanase (endo-1,4-beta-xylanase)". Hence, the hemicellulase as described herein may also be beta-1,4-xylanase (endo-1,4-beta-xylanase). The xylan and arabinoxylan can, for example, be derived from various plants and be insoluble or soluble. Examples of the plants can include, for example, corn, wheat, and beechwood. Xylose from the main chain of corn arabinoxylan has been modified with 4-O-methyl glucuronic acid as well as arabinose, and hence, corn arabinoxylan can also be referred to as "glucuronoarabinoxylan". The hemicellulase as described herein may have, specifically, an activity of cleaving the beta-1,4-glycoside bond between xylose residues that form the backbone of glucuronoarabinoxylan such as corn arabinoxylan (glucuronoarabinoxylan endo-1,4-beta-xylanase activity). A hemicellulase having glucuronoarabinoxylan endo-1,4-beta-xylanase activity can also be referred to as "glucuronoarabinoxylan endo-1,4-beta-xylanase" (EC 3.2.1.136). Hence, the hemicellulase as described herein may also be glucuronoarabinoxylan endo-1,4-beta-xylanase (EC 3.2.1.136). The hemicellulase as described herein may also have an activity of releasing side chain arabinose from arabinoxylan (alpha-L-arabinofuranosidase activity). A hemicellulase having alpha-L-arabinofuranosidase activity can also be referred to as "alpha-L-arabinofuranosidase" (EC 3.2.1.55). Hence, the hemicellulase as described herein may also be alpha-L-arabinofuranosidase (EC 3.2.1.55). The hemicellulase as described herein may have, particularly, an activity of degrading corn NSP, specifically an activity of degrading arabinoxylan contained in corn NSP, more specifically an activity of degrading insoluble arabinoxylan contained in corn NSP. The term "an activity of degrading insoluble arabinoxylan (insoluble arabinoxylan degradation activity)" may mean, particularly, an activity of generating soluble arabinoxylan from insoluble arabinoxylan.

The activities exemplified above each are an example of hemicellulase activity. The hemicellulase as described herein may have one of these hemicellulase activities, or may have two or more of these hemicellulase activities.

Hemicellulase activity can be measured by incubating an enzyme with a substrate, and measuring enzyme- and substrate-dependent generation of a product. The substrate and product can be appropriately chosen according to the kind of hemicellulase activity.

For example, xylanase activity and arabinoxylanase activity can be detected or measured by carrying out an enzymatic reaction using xylan and arabinoxylan as the substrates respectively, and measuring the generation amount of reducing termini. For example, beta-1,4-xylanase activity can be detected or measured by carrying out an enzymatic reaction using xylan or arabinoxylan as the substrate, and measuring the generation amount of reducing termini. For example, glucuronoarabinoxylan endo-1,4-beta-xylanase activity can be detected or measured by carrying out an enzymatic reaction using glucuronoarabinoxylan as the substrate, and measuring the generation amount of reducing termini. The amount of reducing termini can be measured by known methods such as dinitrosalicylic acid (DNS) method and Somogyi-Nelson method.

Furthermore, for example, alpha-L-arabinofuranosidase activity can be detected or measured by carrying out an enzymatic reaction using arabinoxylan as the substrate, and measuring the released amount of arabinose. The amount of arabinose can be measured by known methods such as ion chromatography.

Furthermore, for example, insoluble arabinoxylan degradation activity can be detected or measured by carrying out an enzymatic reaction using insoluble arabinoxylan as the substrate, and measuring the generation amount of soluble arabinoxylan. As the insoluble arabinoxylan, for example, corn NSP or corn DDGS (corn distillers grain from which soluble arabinoxylan has been removed) can be used. Specific examples of methods for detecting or measuring insoluble arabinoxylan degradation activity can include methods described in Example 3 or 7 below. The amount of soluble arabinoxylan can be measured by known methods such as phloroglucinol-acetate method (Sakka M. et al., Appl. Environ. Microbiol., 77(12):4260-4263, 2011).

Specific examples of the hemicellulase as described herein can include a protein having the amino acid sequence of (1) positions 1 to 535 of SEQ ID NO: 4, positions 1 to 536 of SEQ ID NO: 26, positions 1 to 536 of SEQ ID NO: 28, or positions 1 to 536 of SEQ ID NO: 30, (2) positions 1 to 448 of SEQ ID NO: 6, (3) positions 1 to 183 of SEQ ID NO: 9, (4) positions 1 to 527 of SEQ ID NO: 12, positions 1 to 529 of SEQ ID NO: 32, or positions 1 to 390 of SEQ ID NO: 34, or (5) positions 1 to 608 of SEQ ID NO: 14, and having hemicellulase activity. Proteins having the aforementioned amino acid sequences of (1) to (5) are also referred to as Xyn5A, Xyn10B, Xyn11A, Xyn30A, and Xyn43A, respectively. The expression "a gene or protein has a nucleotide or amino acid sequence" can mean that a gene or protein includes the nucleotide or amino acid sequence unless otherwise stated, and also includes that the gene or protein includes only the nucleotide or amino acid sequence.

Xyn5A, Xyn10B, Xyn11A, Xyn30A, and Xyn43A may have xylanase activity and/or arabinoxylanase activity.

Xyn5A, Xyn10B, Xyn11A, and Xyn30A may have, specifically, beta-1,4-xylanase activity. Xyn5A, Xyn10B, and Xyn11A may have beta-1,4-xylanase activity, particularly, against arabinoxylan. Xyn10B, Xyn11A, and Xyn30A may have beta-1,4-xylanase activity, particularly, against xylan. In an embodiment, Xyn10B and Xyn11A have an activity of degrading both beechwood xylan and insoluble wheat xylan. In an embodiment, Xyn5A has an activity of degrading insoluble wheat xylan, while it does not have an activity of degrading beechwood xylan. In an embodiment, Xyn30A does not have an activity of degrading insoluble wheat xylan, while it has an activity of degrading beechwood xylan. Xyn5A, Xyn10B, Xyn11A, and Xyn30A may have an activity of degrading corn NSP, specifically an activity of degrading arabinoxylan contained in corn NSP, more specifically an activity of degrading insoluble arabinoxylan contained in corn NSP.

Xyn43A may have alpha-L-arabinofuranosidase activity (EC 3.2.1.55).

The hemicellulase as described herein may also be a variant of any of the proteins having the aforementioned amino acid sequences, so long as the hemicellulase activity is maintained. Such a variant of which hemicellulase activity is maintained can also be referred to as "conservative variant". Furthermore, the hemicellulase as described herein may also be a fusion protein of any of proteins having the aforementioned amino acid sequences or variants thereof with another peptide. A protein defined with the aforementioned protein name can include not only the proteins exemplified above, but also can include conservative variants thereof, and fusion proteins of any of those proteins or variants thereof with another peptide. That is, for example, the term "Xyn5A" can include not only Xyn5A having the amino acid sequence of positions 1 to 535 of SEQ ID NO: 4, positions 1 to 536 of SEQ ID NO: 26, positions 1 to 536 of SEQ ID NO: 28, or positions 1 to 536 of SEQ ID NO: 30, but also can include conservative variants thereof and, and fusion proteins of any of those proteins or variants thereof with another peptide.

Hereinafter, examples of conservative variants of hemicellulase will be described.

The hemicellulase as described herein may be a protein having any of the aforementioned amino acid sequences of (1) to (5), but which includes substitution, deletion, insertion, and/or addition of one or several amino acid residues at one or several positions, so long as hemicellulase activity is maintained. Although the number meant by the term "one or several" mentioned above may differ depending on the positions of amino acid residues in the three-dimensional structure of the protein or the types of amino acid residues, specifically, it may be, for example, 1 to 10, 1 to 8, 1 to 5, or 1 to 3.

The aforementioned substitution, deletion, insertion, or addition of one or several amino acid residues are/is a conservative mutation that maintains the normal function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions can include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Furthermore, such substitution, deletion, insertion, addition, or inversion of amino acid residues as mentioned above includes a naturally occurring mutation due to an individual difference, or a difference of species of the organism from which the protein is derived (mutant or variant).

The hemicellulase as described herein may also be a protein having an amino acid sequence showing a high homology, for example, a homology of 90% or more, 95% or more, 97% or more, or 99% or more, to the total amino acid sequence of any of the aforementioned amino acid sequences of (1) to (5), so long as hemicellulase activity is maintained. "Homology" can mean "identity".

The hemicellulase as described herein may include a common sequence of the aforementioned hemicellulases. For example, Xyn5A may include a common sequence of the aforementioned Xyn5A, that is, a common sequence of two or more, or all of the amino acid sequences of positions 1 to 535 of SEQ ID NO: 4, positions 1 to 536 of SEQ ID NO: 26, positions 1 to 536 of SEQ ID NO: 28, and positions 1 to 536 of SEQ ID NO: 30. Such a common sequence can be determined by, for example, alignment. Specific examples of a common sequence of Xyn5A can include, for example, the amino acid sequence of positions 218 to 239 of SEQ ID NO: 4.

The hemicellulase as described herein may also be a fusion protein with another peptide. Examples of the other peptide can include marker peptides (marker proteins), peptide tags, and pro sequences or pre-pro sequences such as secretion signal peptides. That is, examples of the fusion protein can include, for example, precursors of hemicellulase. One kind of peptide or two or more kinds of peptides may be fused to hemicellulase. In cases where hemicellulase is a fusion protein with a signal peptide, the signal peptide may be cleaved after expression of the hemicellulase in a host cell capable of secretory production, and thereby only the hemicellulase moiety may be secreted outside the cell. In addition, even in cases where the hemicellulase is not secreted, the signal peptide may be cleaved in a host cell, and a mature protein may be generated. In cases where hemicellulase is a fusion protein, the aforementioned homology represents homology in the residual portion of hemicellulase from which such other peptide have been removed (e.g. mature protein moiety).

Marker peptides are not particularly limited, so long as they are peptides that can function as a marker, and specific examples thereof can include, for example, alkaline phosphatase, Fc region of antibody, HRP, GFP, etc. Specific examples of peptide tags can include, but are not particularly limited to, known peptide tags such as Myc tag, His tag, FLAG tag, and GST tag. Secretion signal peptides are not particularly limited, so long as they can function in a host for expressing DNA encoding hemicellulase, and examples thereof can include, for example, secretion signal peptides of Sec or Tat secretion system derived from coryneform bacteria for cases of using a coryneform bacterium as a host (see WO01/23591 and WO2005/103278), as well as secretion signal peptides of hemicellulase. The fusion protein can be produced in a conventional manner.

The DNA as described herein is not particularly limited, so long as it encodes the hemicellulase as described herein. Specific examples of the DNA as described herein can include DNAs encoding the aforementioned amino acid sequences of (1) to (5). More specific examples of the DNA as described herein can include DNAs having the nucleotide sequence of positions 115 to 1719 of SEQ ID NO: 3, positions 88 to 1695 of SEQ ID NO: 27, positions 97 to 1704 of SEQ ID NO: 29, or positions 88 to 1695 of SEQ ID NO: 31 (encoding Xyn5A); the nucleotide sequence of positions 136 to 1479 of SEQ ID NO: 5 (encoding Xyn10B); the nucleotide sequence of positions 85 to 633 of SEQ ID NO: 8 (encoding Xyn11A); positions 109 to 1689 of SEQ ID NO: 11, the nucleotide sequence of positions 91 to 1677 of SEQ ID NO: 33, or positions 91 to 1260 of SEQ ID NO: 35 (encoding Xyn30A); and the nucleotide sequence of positions 79 to 1902 of SEQ ID NO: 13 (encoding Xyn43A). The DNA as described herein may also be DNA encoding a conservative variant of any of proteins having these amino acid sequences. The DNA as described herein may also be DNA encoding a fusion protein of any of proteins having these amino acid sequences or variants thereof with another peptide. The DNA as described herein may further include a start codon at 5' terminal side of any of the aforementioned nucleotide sequences. The DNA as described herein may further include a stop codon at 3' terminal side of any of the aforementioned nucleotide sequences. The DNA as described herein may be added with a sequence such as promoter.

The DNA as described herein is not limited to those DNAs, and may also be DNA in which codons encoding amino acids in the coding region have been replaced with equivalent codons encoding the same amino acids. That is, the DNA as described herein may also be a variant of any of the DNAs exemplified above due to the degeneracy of codons.

The DNA as described herein also includes DNA that is able to hybridize under stringent conditions with a probe having a nucleotide sequence complementary to any of the aforementioned nucleotide sequences or with a probe that can be prepared from such a complementary sequence, and encodes a protein having hemicellulase activity. The term "stringent conditions" can refer to conditions under which a so-called specific hybrid is formed, and a non-specific hybrid is not formed. Examples of the stringent conditions can include those under which highly homologous DNAs hybridize to each other, for example, DNAs not less than 50%, 65%, 80% 90%, 95%, 97%, or 99% homologous, hybridize to each other, and DNAs less homologous than the above do not hybridize to each other, or conditions of washing of typical Southern hybridization, i.e., conditions of washing once, or 2 or 3 times, at a salt concentration and temperature corresponding to 1×SSC, 0.1% SDS at 60° C.; 0.1×SSC, 0.1% SDS at 60° C.; or 0.1×SSC, 0.1% SDS at 68° C. Furthermore, for example, when a DNA fragment having a length of about 300 bp is used as the probe, the washing conditions of the hybridization may be, for example, 50° C., 2×SSC and 0.1% SDS.

The percentage of the sequence identity between two sequences can be determined by, for example, using a mathematical algorithm. Non-limiting examples of such a mathematical algorithm can include the algorithm of Myers and Miller (1988) CABIOS 4:11-17, the local homology algorithm of Smith et al (1981) Adv. Appl. Math. 2:482, the homology alignment algorithm of Needleman and Wunsch (1970) J. Mol. Biol. 48:443-453, the method for searching homology of Pearson and Lipman (1988) Proc. Natl. Acad. Sci. 85:2444-2448, and an modified version of the algorithm of Karlin and Altschul (1990) Proc. Natl. Acad. Sci. USA 87:2264, such as that described in Karlin and Altschul (1993) Proc. Natl. Acad. Sci. USA 90:5873-5877.

By using a program based on such a mathematical algorithm, sequence comparison (i.e. alignment) for determining the sequence identity can be performed. The program can be appropriately executed by a computer. Examples of such a program can include, but are not limited to, CLUSTAL of PC/Gene program (available from Intelligenetics, Mountain View, Calif.), ALIGN program (Version 2.0), and GAP, BESTFIT, BLAST, FASTA, and TFASTA of Wisconsin Genetics Software Package, Version 8 (available from Genetics Computer Group (GCG), 575 Science Drive, Madison, Wis., USA). Alignment using these programs can be performed by using, for example, initial parameters. The CLUSTAL program is well described in Higgins et al. (1988) Gene 73:237-244, Higgins et al. (1989) CABIOS 5:151-153, Corpet et al. (1988) Nucleic Acids Res. 16:10881-90, Huang et al. (1992) CABIOS 8:155-65, and Pearson et al. (1994) Meth. Mol. Biol. 24:307-331.

In order to obtain a nucleotide sequence homologous to a target nucleotide sequence, in particular, for example, BLAST nucleotide search can be performed by using BLASTN program with score of 100 and word length of 12. In order to obtain an amino acid sequence homologous to a target protein, in particular, for example, BLAST protein search can be performed by using BLASTX program with score of 50 and word length of 3. See ncbi.nlm.nih.gov for BLAST nucleotide search and BLAST protein search. In addition, Gapped BLAST (BLAST 2.0) can be used in order to obtain an alignment including gap(s) for the purpose of comparison. In addition, PSI-BLAST (BLAST 2.0) can be used in order to perform repetitive search for detecting distant relationships between sequences. See Altschul et al. (1997) Nucleic Acids Res. 25:3389 for Gapped BLAST and PSI-BLAST. When using BLAST, Gapped BLAST, or PSI-BLAST, for example, initial parameters of each program (e.g. BLASTN for nucleotide sequences, and BLASTX for amino acid sequences) can be used. Alignment can also be manually performed.

The sequence identity between two sequences is calculated as the ratio of residues matching in the two sequences when aligning the two sequences so as to fit maximally with each other.

<2> Enzyme Enhancing Hemicellulase Activity and DNA Encoding it

The present invention provides an enzyme enhancing hemicellulase activity and DNA encoding it.

Specific examples of the enzyme enhancing hemicellulase activity can include a protein that includes the amino acid sequence of positions 1 to 469 of SEQ ID NO: 36, and having a property of enhancing hemicellulase activity. A protein having this amino acid sequence can be referred to as Abf51A.

The type and number of hemicellulase activity/activities enhanced by the enzyme enhancing hemicellulase activity are not particularly limited. The enzyme enhancing hemicellulase activity may have a property of enhancing, for example, one or more of the hemicellulase activities exemplified above. The enzyme enhancing hemicellulase activity may have a property of enhancing, specifically, for example, an activity of degrading wheat arabinoxylan and/or an activity of degrading corn NSP. The enzyme enhancing hemicellulase activity may also have a property of enhancing, for example, activity/activities of one or more of Xyn5A, Xyn10B, Xyn11A, Xyn30A, and/or Xyn43A. The enzyme enhancing hemicellulase activity may also have a property of enhancing, specifically, for example, an activity of Xyn5A.

The enzyme enhancing hemicellulase activity may or may not have hemicellulase activity.

The enzyme enhancing hemicellulase activity may also be a variant of any of proteins having the aforementioned amino acid sequence, so long as the property of enhancing hemicellulase activity is maintained. To such a variant, the descriptions concerning variants of hemicellulase can be similarly applied.

Whether a protein has a property of enhancing hemicellulase activity can be confirmed by carrying out an enzymatic reaction using a hemicellulase in the presence and absence of the protein, and comparing hemicellulase activities.

Specific examples of the DNA encoding the enzyme enhancing hemicellulase activity can include DNAs encoding the aforementioned amino acid sequence. More specific examples of the DNA encoding the enzyme enhancing hemicellulase activity can include DNAs having the nucleotide sequence of positions 82 to 1488 of SEQ ID NO: 37 (encoding Abf51A). The DNA encoding the enzyme enhancing hemicellulase activity may also be DNA encoding a conservative variant of any of proteins having the aforementioned amino acid sequence. The DNA encoding the enzyme enhancing hemicellulase activity may also be DNA encoding a fusion protein of any of proteins having the aforementioned amino acid sequence or variants thereof with another peptide. The DNA encoding the enzyme enhancing hemicellulase activity may further include a start codon at 5' terminal side of the aforementioned nucleotide sequence. The DNA encoding the enzyme enhancing hemicellulase activity may further include a stop codon at 3' terminal side of the aforementioned nucleotide sequence. The DNA encoding the enzyme enhancing hemicellulase activity may be added with a sequence such as promoter. In addition, to the DNA encoding the enzyme enhancing hemicellulase activity, the descriptions concerning the DNA as described herein can be similarly applied.

<3> Production of Hemicellulase

The hemicellulase as described herein can be obtained from, for example, a culture broth of the *Paenibacillus* sp. H2C strain as shown in Example 3. The strain H2C was deposited at the independent administrative agency, National Institute of Technology and Evaluation, Patent Microorganisms Depositary (NPMD; #122, 2-5-8 Kazusakamatari, Kisarazu-shi, Chiba-ken, 292-0818) on Apr. 15, 2016 under the provisions of the Budapest Treaty, and assigned an accession number of NITE BP-02241 with an identification reference of AJ111229.

The hemicellulase as described herein can be produced by making an appropriate host express DNA encoding it (the DNA as described herein). The DNA as described herein may also be referred to as "hemicellulase gene". The hemicellulase gene can be prepared by chemical synthesis, since the amino acid sequence of the hemicellulase as described herein has been identified. The DNA as described herein can also be cloned from the *Paenibacillus* sp. H2C strain on the basis of the sequence thereof by the PCR method etc.

The obtained gene can be used as it is, or after being modified as required. That is, a variant of a gene may be obtained by modifying the gene. The gene can be modified by a known method. For example, it can be modified by site-specific mutagenesis, or an objective mutation can be introduced into a target site of DNA. That is, for example, a coding region of a gene can be modified by the site-specific mutagenesis method so that a specific site of the encoded protein can include substitution, deletion, insertion, and/or addition of amino acid residues. Examples of the site-specific mutagenesis method can include a method using PCR (Higuchi, R., 61, in PCR Technology, Erlich, H. A. Eds., Stockton Press, 1989; Carter P., Meth., in Enzymol., 154, 382, 1987), and a method of using a phage (Kramer, W. and Frits, H. J., Meth. in Enzymol., 154, 350, 1987; Kunkel, T. A. et al., Meth. in Enzymol., 154, 367, 1987). Alternatively, a variant of a gene may also be totally synthesized.

In particular, a host having an enhanced expression of a hemicellulase gene can be used for production of the hemicellulase as described herein. The term "host having an enhanced expression of a hemicellulase gene" can refer to a host introduced with a hemicellulase gene in such a manner that the gene can be expressed, or a host that is a microorganism having a hemicellulase gene and in which expression of the gene has been enhanced.

The host is not particularly limited, so long as it can express the hemicellulase. Examples of the host can include, for example, bacteria, fungi, plant cells, insect cells, and animal cells. Preferred examples of the host can include microorganisms such as bacteria and fungi.

Examples of the bacteria can include gram-negative bacteria and gram-positive bacteria. Examples of the gram-negative bacteria can include, for example, bacteria belonging to the family Enterobacteriaceae, such as *Escherichia* bacteria, *Enterobacter* bacteria, and *Pantoea* bacteria. Examples of the gram-positive bacteria can include *Bacillus* bacteria, coryneform bacteria such as *Corynebacterium* bacteria, and actinomycetes. Examples of the *Escherichia* bacteria can include, for example, *Escherichia coli*. Examples of the *Corynebacterium* bacteria can include, for example, *Corynebacterium glutamicum* and *Corynebacterium ammoniagenes* (*Corynebacterium* stationis). Specific examples of *Escherichia coli* can include, for example, *Escherichia coli* K-12 strains such as W3110 strain (ATCC 27325) and MG1655 strain (ATCC 47076); *Escherichia coli* KS strain (ATCC 23506); *Escherichia coli* B strains such as BL21 (DE3) strain and a recA-strain thereof, BLR(DE3); and derivative strains thereof.

These strains are available from, for example, the American Type Culture Collection (Address: P.O. Box 1549, Manassas, Va. 20108, United States of America). That is, registration numbers are given to the respective strains, and the strains can be ordered by using these registration numbers (can refer to atcc.org). The registration numbers of the strains are listed in the catalogue of the American Type Culture Collection. These strains can also be obtained from, for example, the depositories at which the strains were deposited. The BL21(DE3) strain is available from, for example, Life Technologies (product number C6000-03).

Methods for introducing the hemicellulase gene into a host are not particularly limited. In a host, a hemicellulase gene may be harbored in such a manner that it can be expressed under control of a promoter that functions in the host. In the host, the hemicellulase gene may be present on a vector autonomously replicable independent of the chromosome, such as plasmid, or may be introduced into the chromosome. The host may have only one copy of the hemicellulase gene, or may have two or more copies of the hemicellulase gene. The host may have only one kind of hemicellulase gene, or may have two or more kinds of hemicellulase genes.

The promoter for expressing the hemicellulase gene is not particularly limited so long as it is a promoter that functions in the host. The "promoter that functions in a host" can refer to a promoter that has a promoter activity in the host. The promoter may be a promoter derived from, that is, native to, the host, or may be a heterologous promoter. The promoter may be the native promoter of the hemicellulase gene, or may be a promoter of another gene. The promoter may be stronger than the native promoter of the hemicellulase gene. Examples of strong promoters that function in Enterobacteriaceae bacteria, such as *Escherichia coli*, can include, for example, T7 promoter, trp promoter, trc promoter, lac promoter, tac promoter, tet promoter, araBAD promoter, rpoH promoter, msrA promoter, Pm1 promoter (derived from the genus *Bifidobacterium*), PR promoter, and PL promoter. Examples of strong promoters that function in coryneform bacteria can include the artificially modified P54-6 promoter (Appl. Microbiol. Biotechnol., 53, 674-679 (2000)), pta, aceA, aceB, adh, and amyE promoters inducible in coryneform bacteria with acetic acid, ethanol, pyruvic acid, or the like, cspB, SOD, and tuf (EF-Tu) promoters, which are potent promoters capable of providing a large expression amount in coryneform bacteria (Journal of Biotechnology, 104 (2003) 311-323; Appl. Environ. Microbiol., 2005 December; 71 (12):8587-96), as well as lac promoter, tac promoter, and trc promoter. Examples of promoters that function in fungi such as *Talaromyces cellulolyticus* can include, for example, glaA promoter, and promoters of genes encoding saccharide hydrolases, such as cellulase gene and xylanase gene. Furthermore, as the promoter, a highly-active type of an existing promoter may also be obtained by using various reporter genes. For example, by making the −35 and −10 regions in a promoter region closer to the consensus sequence, the activity of the promoter can be enhanced (WO00/18935). Examples of highly active-type promoter can include various tac-like promoters (Katashkina J I et al., Russian Federation Patent Application No. 2006134574) and pnlp8 promoter (WO2010/027045). Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

Also, a terminator for termination of gene transcription may be located downstream of the hemicellulase gene. The terminator is not particularly limited so long as it functions in the bacterium as described herein. The terminator may be a terminator derived from the host, or a heterogenous terminator. The terminator may be the native terminator of the hemicellulase gene, or a terminator of another gene. Specific examples of the terminator can include, for example, T7 terminator, T4 terminator, fd phage terminator, tet terminator, and trpA terminator.

The hemicellulase gene can be introduced into a host, for example, by using a vector containing the gene. A vector containing the hemicellulase gene can also be referred to as an expression vector or recombinant vector for the hemicellulase gene. The expression vector for the hemicellulase gene can be constructed by, for example, ligating a DNA fragment containing the hemicellulase gene with a vector that functions in the host. By transforming the host with the expression vector for the hemicellulase gene, a transformant into which the vector has been introduced can be obtained, i.e. the gene can be introduced into the host. As the vector, a vector autonomously replicable in the cell of the host can be used. The vector can be a multi-copy vector. Furthermore, the vector can have a marker such as an antibiotic resistance gene for selection of transformant. Furthermore, the vector may have a promoter and/or terminator for expressing the introduced gene. The vector may be, for example, a vector derived from a bacterial plasmid, a vector derived from a yeast plasmid, a vector derived from a bacteriophage, cosmid, phagemid, or the like. Specific examples of a vector autonomously replicable in Enterobacteriaceae bacteria such as *Escherichia coli* can include, for example, pUC19, pUC18, pHSG299, pHSG399, pHSG398, pBR322, pSTV29 (all of these are available from Takara Bio), pACYC184, pMW219 (NIPPON GENE), pTrc99A (Pharmacia), pPROK series vectors (Clontech), pKK233-2 (Clontech), pET series vectors (Novagen), pQE series vectors (QIAGEN), pCold TF DNA (TaKaRa), pACYC series vectors, and the broad host spectrum vector RSF1010. Specific examples of vector autonomously replicable in coryneform bacteria can include, for example, pHM1519 (Agric. Biol. Chem., 48, 2901-2903 (1984)); pAM330 (Agric. Biol. Chem., 48, 2901-2903 (1984)); plasmids obtained by improving these and having a drug resistance gene; plasmid pCRY30 described in Japanese Patent Laid-open (Kokai) No. 3-210184; plasmids pCRY21, pCRY2KE, pCRY2KX, pCRY31, pCRY3KE, and pCRY3KX described in Japanese Patent Laid-open (Kokai) No. 2-72876 and U.S. Pat. No. 5,185,262; plasmids pCRY2 and pCRY3 described in Japanese Patent Laid-open (Kokai) No. 1-191686; pAJ655, pAJ611, and pAJ1844 described in Japanese Patent Laid-open (Kokai) No. 58-192900; pCG1 described in Japanese Patent Laid-open (Kokai) No. 57-134500; pCG2 described in Japanese Patent Laid-open (Kokai) No. 58-35197; pCG4 and pCG11 described in Japanese Patent Laid-open (Kokai) No. 57-183799, pVK7 described in Japanese Patent Laid-open (Kokai) No. 10-215883; and pVC7 described in Japanese Patent Laid-open (Kokai) No. 9-070291. Specific examples of a vector autonomously replicable in fungi such as *Talaromyces cellulolyticus* can include, for example, pANC202 (J Ind Microbiol Biotechnol. 2013 August; 40(8):823-30). When the expression vector is constructed, for example, the hemicellulase gene having a native promoter region as it is may be incorporated into a vector, a coding region of the hemicellulase ligated downstream from such a promoter as mentioned above may be incorporated into a vector, or a coding region of the hemicellulase may be incorporated into a vector downstream from a promoter inherently present in the vector.

Vectors, promoters, and terminators available in various microorganisms are disclosed in detail in "Fundamental Microbiology Vol. 8, Genetic Engineering, KYORITSU SHUPPAN CO., LTD, 1987", and those can be used.

The hemicellulase gene can also be introduced into, for example, a chromosome of a host. A gene can be introduced into a chromosome by, for example, using homologous recombination (Miller, J. H., Experiments in Molecular Genetics, 1972, Cold Spring Harbor Laboratory). Examples of the gene transfer method utilizing homologous recombination can include, for example, a method using a linear DNA such as Red-driven integration (Datsenko, K. A., and Wanner, B. L., Proc. Natl. Acad. Sci. USA, 97:6640-6645 (2000)), a method of using a plasmid containing a temperature sensitive replication origin, a method of using a plasmid capable of conjugative transfer, a method of using a suicide vector not having a replication origin that functions in a host, and a transduction method using a phage. Only one copy, or two or more copies of a gene may be introduced. For example, by performing homologous recombination using a sequence which is present in multiple copies on a chromosome as a target, multiple copies of a gene can be introduced into the chromosome. Examples of such a sequence which is present in multiple copies on a chromosome can include repetitive DNAs, and inverted repeats located at the both ends of a transposon. Alternatively, homologous recombination may be performed by using an appropriate sequence on a chromosome such as a gene unnecessary for production of the objective substance as a target. Furthermore, a gene can also be randomly introduced into a chromosome by using a transposon or Mini-Mu (Japanese Patent Laid-open (Kokai) No. 2-109985, U.S. Pat. No. 5,882,888, EP 805867 B1). When the gene is introduced into a chromosome, for example, the hemicellulase gene having a native promoter region as it is may be incorporated into a chromosome, a coding region of the hemicellulase ligated downstream from such a promoter as mentioned above may be incorporated into a chromosome, or a coding region of the hemicellulase may be incorporated into a chromosome downstream from a promoter inherently present on the chromosome.

In addition, by replacing an expression control sequence such as promoter of the hemicellulase gene with a more potent expression control sequence in a *Paenibacillus* bacterium having this gene, expression of the hemicellulase gene can be enhanced.

Introduction of a gene into a chromosome can be confirmed by, for example, Southern hybridization using a probe having a sequence complementary to a part or the whole of the gene, or PCR using primers prepared on the basis of the nucleotide sequence of the gene.

The method for the transformation is not particularly limited, and conventionally known methods can be used. Examples of transformation method can include, for example, a method of treating recipient cells with calcium chloride so as to increase the permeability thereof for DNA, which has been reported for the *Escherichia coli* K-12 strain (Mandel, M. and Higa, A., J. Mol. Biol., 1970, 53, 159-162), a method of preparing competent cells from cells which are in the growth phase, followed by transformation with DNA, which has been reported for *Bacillus subtilis* (Duncan, C. H., Wilson, G. A. and Young, F. E., Gene, 1997, 1:153-167), and so forth. Furthermore, as the transformation method, there can also be used a method of making DNA-recipient cells into protoplasts or spheroplasts, which can easily take up recombinant DNA, followed by introducing a recombinant DNA into the DNA-recipient cells, which is known to be applicable to *Bacillus subtilis*, actinomycetes, and yeasts (Chang, S. and Choen, S. N., 1979, Mol. Gen. Genet., 168:111-115; Bibb, M. J., Ward, J. M. and Hopwood, O. A., 1978, Nature, 274:398-400; Hinnen, A., Hicks, J. B. and Fink, G. R., 1978, Proc. Natl. Acad. Sci. USA, 75:1929-1933). Furthermore, as the transformation method, the electric pulse method reported for coryneform bacteria (Japanese Patent Laid-open (Kokai) No. 2-207791) can also be used.

By culturing the host having the hemicellulase gene in a culture medium, the hemicellulase can be expressed. During the culture, the expression of the hemicellulase gene can be induced as required. Conditions for induction of gene expression can be appropriately chosen depending on various conditions such as the structure of gene expression system.

The culture medium and culture conditions are not particularly limited, so long as the host having the hemicellulase gene can proliferate, and the hemicellulase can be produced. The culture medium and culture conditions can be appropriately chosen depending on various conditions such as the type of the host. Culture can be carried out, for example, using a usual culture medium under usual conditions used for culturing microorganisms such as bacteria and fungi. Regarding specific culture medium compositions and culture conditions for culturing bacteria, for example, culture medium compositions and culture conditions used for production of various substances using bacteria such as *E. coli* and coryneform bacteria can be used as a reference.

As the culture medium, for example, a liquid culture medium containing a carbon source, nitrogen source, phosphate source, sulfur source, and ingredients such as other various organic and inorganic ingredients as required can be used. The types and concentrations of the culture medium components can be appropriately chosen by those skilled in the art.

The carbon source is not particularly limited, so long as the host having the hemicellulase gene can utilize it. Specific examples of the carbon source can include, for example, saccharides such as glucose, fructose, sucrose, lactose, galactose, xylose, arabinose, blackstrap molasses, hydrolysate of starch, and hydrolysate of biomass, organic acids such as acetic acid, fumaric acid, citric acid, succinic acid, and malic acid, alcohols such as glycerol, crude glycerol, and ethanol, and aliphatic acids. Examples of the carbon source also can include biomass containing a hemicellulose component described below. As the carbon source, one kind of carbon source may be used, or two or more kinds of carbon sources may be used in combination.

Specific examples of the nitrogen source can include, for example, ammonium salts such as ammonium sulfate, ammonium chloride, and ammonium phosphate, organic nitrogen sources such as peptone, yeast extract, meat extract, corn steep liquor, and soybean protein decomposition product, ammonia, and urea. As the nitrogen source, one kind of nitrogen source may be used, or two or more kinds of nitrogen sources may be used in combination.

Specific examples of the phosphate source can include, for example, phosphate salts such as potassium dihydrogenphosphate and dipotassium hydrogenphosphate, and phosphoric acid polymers such as pyrophosphoric acid. As the phosphate source, one kind of phosphate source may be used, or two or more kinds of phosphate sources may be used in combination.

Specific examples of the sulfur source can include, for example, inorganic sulfur compounds such as sulfates, thiosulfates, and sulfites, and sulfur-containing amino acids such as cysteine, cystine, and glutathione. As the sulfur source, one kind of sulfur source may be used, or two or more kinds of sulfur sources may be used in combination.

Specific examples of the other various organic and inorganic components can include, for example, inorganic salts such as sodium chloride, and potassium chloride; trace metals such as iron, manganese, magnesium, and calcium; vitamins such as vitamin B1, vitamin B2, vitamin B6, nicotinic acid, nicotinamide, and vitamin B12; amino acids; nucleic acids; and organic components containing these such as peptone, casamino acid, yeast extract, and soybean protein decomposition product. As the other various organic and inorganic components, one kind of component may be used, or two or more kinds of components may be used in combination.

The culture can be performed, for example, aerobically as aeration culture or shaking culture using a liquid culture medium. The culture temperature may be, for example, 15 to 43° C. The pH during the culture may be, for example, 5 to 9. The culture period may be, for example, 2 hours to 20 days. The culture can be performed as batch culture, fed-batch culture, continuous culture, or a combination of these. The culture may also be performed as separate pre-culture and main culture. For example, the pre-culture may be performed on a solid culture medium such as an agar medium, and the main culture may be performed in a liquid culture medium.

By culturing the host having the hemicellulase gene in a culture medium under such conditions as mentioned above, a culture broth containing the hemicellulase is obtained. The hemicellulase can be accumulated in, for example, microbial cells of the host and/or the culture medium. The term "microbial cell" may be appropriately read as "cell" depending on the type of the host.

Production of the hemicellulase can be confirmed by, for example, measuring hemicellulase activity in an appropriate fraction such as culture supernatant and cell extract.

The hemicellulase may be used in a state that it is contained in the culture broth or the like, or may be separated and purified from the culture broth or the like as required and used as a crude enzyme fraction or a purified enzyme.

That is, for example, when the hemicellulase is accumulated in microbial cells of the host, by subjecting the cells to disruption, lysis, extraction, etc. as required, the hemicellulase can be collected. The microbial cells can be collected from the culture broth by centrifugation or the like. Disruption, lysis, extraction, etc. of the cells can be performed by known methods. Examples of such methods can include, for example, disruption by ultrasonication, disruption in Dyno-Mill, disruption in bead mill, disruption with French press, and lysozyme treatment. One of these methods may be used alone, or two or more of these methods may be used in combination as required. Also, for example, when the hemicellulase is accumulated in the culture medium, a culture supernatant can be obtained by centrifugation or the like, and the hemicellulase can be collected from the culture supernatant.

The hemicellulase can be purified by known methods used for purification of enzymes. Examples of such methods can include, for example, ammonium sulfate fractionation, ion exchange chromatography, hydrophobic chromatography, affinity chromatography, gel filtration chromatography, and isoelectric precipitation. One of these methods may be used alone, or two or more of these methods may be used in combination as required. The hemicellulase may be purified to a desired extent.

Not only the purified hemicellulase, but also any fraction containing the hemicellulase may be used as the "hemicellulase" for such a use purpose as degradation of hemicellulose. Such a fraction containing the hemicellulase is not particularly limited, so long as it contains the hemicellulase so that the hemicellulase can act on cellulose. Examples of such a fraction can include, for example, culture broth, culture supernatant, processed product of microbial cells (disruption product, lysate, extract (cell-free extract). etc.), partially purified products (roughly purified products) of these, and combinations of these. These fractions each may be used alone, or may be used together with a purified hemicellulase.

In the culture broth, other enzyme(s) different from the hemicellulase as described herein may also be produced and accumulated together with the hemicellulase as described herein. The hemicellulase as described herein may be collected as a mixture with such other enzyme(s), or may be collected separately from such other enzyme(s).

The hemicellulase as described herein may be made into a preparation (formulation) as required. That is, the present invention provides a hemicellulase preparation containing the hemicellulase as described herein. This hemicellulase preparation can also be referred to as "hemicellulase preparation as described herein". The dosage form of the hemicellulase preparation as described herein is not particularly limited, and can be appropriately chosen according to various conditions such as use purpose of the hemicellulase. Examples of the dosage form can include, for example, solution, suspension, powder, tablet, pill, and capsule. For preparing such a preparation, for example, pharmaceutically acceptable additives such as excipients, binders, disintegrating agents, lubricants, stabilizers, corrigents, odor-masking agents, perfumes, diluents, and surfactants can be used.

The type and number of hemicellulase contained in the hemicellulase preparation as described herein are not particularly limited. The number of kinds of hemicellulase contained in the hemicellulase preparation as described herein may be one or more, two or more, or three or more. While any hemicellulase included in the hemicellulase as described herein independently shows hemicellulase activity, a combination of two or three or more hemicellulases shows an increased specific activity. Hence, a hemicellulase preparation containing a combination of these enzymes is useful for degradation of hemicellulose. The combination of enzymes is not particularly limited. Specific examples of the combination of enzymes can include, for example, combinations of Xyn5A and Xyn10B; Xyn5A and Xyn30A; Xyn5A and Xyn43A; Xyn10B and Xyn30A; Xyn10B and Xyn43A; and Xyn30A and Xyn43A. The mixing ratio of hemicellulases in such a preparation is not particularly limited. In cases of a combination of two kinds of enzymes, examples of the mixing ratio can include, for example, 95:5 to 5:95, or 70:30 to 30:70, in terms of weight ratio.

The hemicellulase preparation as described herein may contain other enzyme(s) in addition to the hemicellulase as described herein. The type and number of the other enzyme (s) contained in the hemicellulase preparation as described herein are not particularly limited. The number of kinds of the other enzyme(s) contained in the hemicellulase preparation as described herein may be one or more, two or more, or three or more. Examples of the other enzymes can include hemicellulases other than the hemicellulase as described herein. Examples of the other enzymes also can include saccharide hydrolases other than hemicellulases, such as cellulase and xylobiase (beta-xylosidase). Examples of the other enzymes also can include the enzyme enhancing hemicellulase activity, such as Abf51A. The combination of the hemicellulase as described herein and other enzyme(s) is not particularly limited. The combination of the hemicellulase as described herein and other enzyme(s) may be, for example, a combination by which the activity of the hemicellulase as described herein is enhanced. Specific examples of the combination of the hemicellulase as described herein and other enzyme(s) can include, for example, a combination of one or more of Xyn5A, Xyn10B, Xyn11A, Xyn30A, and Xyn43A with Abf51A. Particular examples of the combination of the hemicellulase as described herein and other enzyme(s) can include a combination including Xyn5A and Abf51A. In other words, the hemicellulase preparation as described herein may contain at least Xyn5A.

The other enzyme can be produced in a similar manner with the hemicellulase as described herein. When two or more kinds of enzymes, such as the hemicellulase as described herein and other enzyme(s), are used in combination, these enzymes may be collectively produced, or may be each independently produced. For example, by co-expressing the hemicellulase as described herein and the enzyme enhancing hemicellulase activity in a single host, these enzymes can be collectively produced.

<4> Use of Hemicellulase

The hemicellulase as described herein can be used for the degradation of hemicellulose. For example, by treating a hemicellulosic substrate with the hemicellulase as described herein, a saccharification product can be produced.

The type and number of hemicellulase to be used are not particularly limited. The number of kinds of hemicellulase to be used may be one or more, two or more, or three or more. The hemicellulase as described herein may be used independently, or may be used in combination with component (s) other than the hemicellulase, such as other enzymes. The hemicellulase as described herein may be used, for example, as a form of an enzyme preparation containing the hemicellulase, in particular, an enzyme preparation containing the hemicellulase and other enzyme(s). Examples of such an enzyme preparation can include the hemicellulase preparation as described herein. Examples of the other enzymes can include those exemplified above. To the combination of enzymes, the descriptions concerning the combination of enzymes in the hemicellulase preparation as described herein can be similarly applied. The hemicellulase as described herein may be used as a free form, or may be used as an immobilized enzyme immobilized to a solid phase such as resin. When a plurality of enzymes is used, these enzymes may simultaneously act on a hemicellulosic substrate, or may successively or independently act on a hemicellulosic substrate.

Examples of the hemicellulosic substrate can include, for example, biomass resources containing hemicellulose. The term "biomass resource" can include cellulosic and/or lignocellulosic biomass produced by plants or algae and containing a hemicellulose component. Examples of such biomass can include, for example, DDGS such as corn DDGS, bagasse, wood, bran, wheat straw, rice straw, rice husk, soybean meal, soybean curd refuse, coffee grounds, rice bran, etc.

As methods for degrading or hydrolyzing biomass resources, known methods can be used. For example, the biomass resource may be a dried product or a wet product, and the biomass resource can be preliminarily ground to a size of 100-1000 μm in order to improve treatment efficiency. The grounding can be carried out by using a machine such as ball mill, vibration mill, cutter mill, and hammer mill. The ground biomass resource can be suspended in an aqueous medium. Then, to degrade or hydrolyze the biomass resource, the hemicellulase as described herein and, as required, cellulase can be added to the aqueous medium, and the mixture can be heated with stirring. In this method, it is sufficient that the pH and temperature of the reaction mixture each are within a range in which chosen enzyme(s), such as the hemicellulase as described herein, is/are not inactivated. For example, usually, when the reaction is carried out under ordinary pressure, the temperature may be within a range of 5 to 70° C., 25 to 60° C., or 35 to 50° C., and the pH may be within a range of 3.0 to 10.0, or 5.0 to 8.0. For example, when using Cellic Ctec of Novozymes as cellulase, exemplary conditions can be 35 to 55° C. and pH4.5 to 6.0. Examples of the amount of enzyme can include 0.1 to 0.5% (w/w TS, total solid). The reaction period can be chosen according to the amount of enzyme etc.

The use amount of the hemicellulase as described herein is not particularly limited, and it may be appropriately chosen by carrying out a preliminarily experiment etc.

By degrading the biomass resource as described above, saccharide(s) is/are generated, that is, a saccharide solution is obtained. Examples of saccharides can include, for example, glucose, xylose, mannose, and arabinose. Specifically, for example, by saccharifying a hemicellulose component, a saccharide solution containing xylose and arabinose is obtained. Specifically, for example, by saccharifying a cellulose component, a saccharide solution containing glucose is obtained.

The obtained saccharide solution can be used as it is, or after being subjected to such a treatment as concentration, dilution, drying, fractionation, purification, and conversion as required, depending on the use purpose thereof. For example, the obtained saccharide solution can be used after isomerization or degradation by chemical reaction or enzymatic reaction. For example, the obtained saccharide solution can also be used as a dried product after removal of moisture. In addition, component(s) in the saccharide solution can be fractionated and used as required. The term "fractionated product" also includes a roughly-purified product and a purified product. Examples of the purified product can include saccharides such as glucose, xylose, mannose, and arabinose.

The saccharide solution obtained by the aforementioned method, including processed products such as fractionated product, can be used as, for example, a carbon source for production of an objective substance by fermentation. Examples of the objective substance can include, for example, alcohols such as methanol, ethanol, propanol, isopropanol, butanol, and butanediol. Other examples of the objective substance can include acetic acid, lactic acid, propionic acid, 3-hydroxypropionic acid, succinic acid, citric acid, amino acids, and nucleic acids.

The hemicellulase as described herein can also be used as a component of an animal feed composition. The term "animal feed composition" may be synonymous to the term "animal feed". The animal feed composition can be produced by a usual method using the same components as those of a usual feed composition depending on the type of the animal to be administered with the composition, except that the animal feed composition contains the hemicellulase as described herein. The animal feed composition as described herein can be obtained by adding the hemicellulase as described herein or the enzyme preparation containing the same, or an animal feed additive containing the hemicellulase as described herein described below at any stage of production process of a feed composition, or by adding and mixing the hemicellulase as described herein or the enzyme preparation containing the same, or an animal feed additive containing the hemicellulase as described herein described below with a usual feed composition. One kind of hemicellulase may be used, or two or more kinds of hemicellulases may be used. Feed component(s) other than the hemicellulase is/are not particularly limited, and can include a biomass resource containing a hemicellulosic substrate, such as soybean meal, corn, DDGS, milo, barley, wheat, wheat bran, cassava, and rice bran. The animal feed composition may contain other enzyme(s) in addition to the hemicellulase as described herein. Examples of the other enzymes can include amylase, protease, pectinase, phytase, lipase, and the like, as well as the enzymes exemplified above. The animal to be fed with the feed is not particularly limited, and examples thereof can include ruminants such as cattle, goat, sheep, and deer; domestic animals such as pig and boar; poultry such as chicken, quail, turkey, duck, and goose; and the like. The form of the feed is not particularly limited, and the feed may be in any form such as mash, pellet, granule, crumble, flake, and powder.

The hemicellulase as described herein or the enzyme preparation containing the same can also be used as an animal feed additive. The animal feed additive is typically added and mixed with an animal feed before administration of the feed. The animal feed additive may also be administered to an animal independently of the feed, or the animal feed additive and the feed as separate ingredients may also be simultaneously administered to an animal. In cases where the animal feed additive is not mixed with an animal feed before administration as with the latter case, the animal feed additive can be regarded as an enzyme preparation for promoting use of the animal feed. The term "animal feed additive" can include such an enzyme preparation.

The animal feed additive may include only the hemicellulase as described herein or the enzyme preparation containing the same, or may contain another feed additive ingredient. When the other feed additive ingredient is contained, the feed additive (feed additive composition) can be produced by a usual method using the same components as those of a usual feed additive depending on the type of the animal to be administered with the additive. The animal feed additive as described herein can be obtained by adding the hemicellulase as described herein or the enzyme preparation containing the same at any stage of production process of a feed additive, or by adding and mixing the hemicellulase as described herein or the enzyme preparation containing the same with a usual feed composition. One kind of hemicellulase may be used, or two or more kinds of hemicellulases may be used in combination.

Examples of the ingredient other than the hemicellulase as described herein can include carriers, excipients, disintegrants, diluents, antioxidants, binders, nutritional supplement ingredients, agents for promoting use of nutrients, and the like. Examples of carriers can include starch, maltodextrin, calcium carbonate, cyclodextrin, wheat or wheat component, sucrose, glucose, sodium sulfate, talc, polyvinyl alcohol, sorbitol, glycerol, benzoate, sorbate, propylene glycol, 1,3-propanediol, paraben, sodium chloride, citrate, acetate, phosphate, calcium, pyrosulfite, formate, and the like. Examples of excipients can include cellulose such as microcrystalline cellulose, lactose, sodium citrate, calcium carbonate, calcium hydrogen phosphate, glycine, starch, lactose, high molecular weight polyethylene glycol, and the like. Examples of disintegrants can include starch, sodium starch glycolate, croscarmellose sodium, certain complex silicate, and the like. Examples of diluents can include water, ethanol, propylene glycol, glycerin, and the like. Examples of antioxidants can include ethoxyquin, dibutylhydroxytoluene, butylhydroxyanisole, and the like. Examples of binders can include sodium alginate, sodium caseinate, sodium carboxymethylcellulose, propylene glycol, sodium polyacrylate, and the like. Examples of nutritional supplement ingredients can include amino acids, vitamins, minerals, and the like. Examples of agents for promoting use of nutrients can include antimicrobial agents, antibiotics, perfumes, taste-imparting agents, enzymes, probiotics, and the like.

One kind of such an ingredient as mentioned above may be used, or any combination of plural kinds of such ingredients as mentioned above may be used. The animal feed additive may contain other enzyme(s) in addition to the hemicellulase as described herein. Such other enzyme(s) may be the same as those described for the animal feed.

The form of the animal feed additive is not particularly limited, and the feed additive may be in any form such as mash, pellet, granule, crumble, flake, and powder. When the feed additive has a powdery form, the feed additive can be produced by processing a solution containing the enzyme as it is or a mixture of such an enzyme solution with such ingredient(s) as mentioned above into a powdery form by spray drying or the like.

The hemicellulase as described herein, the enzyme preparation containing the same, and the animal feed additive each may be used as a pretreatment agent for a feed before administering the feed to an animal. Conditions for the pretreatment can be set according to the aforementioned reaction conditions for degradation or saccharification of a biomass resource.

The amount of the hemicellulase as described herein that is present in the feed composition (feed) or the feed additive is not particularly limited, and it can be set according to the type and the amount of the biomass resource contained in the feed.

EXAMPLES

Hereinafter, the present invention will be more specifically explained with reference to the following non-limiting examples.

Example 1: Isolation of Corn NSP-Degrading Microorganisms and Identification of Strain (1) Screening of Corn NSP-Degrading Microorganisms by Enrichment Culture A culture medium containing NSP, an insoluble fiber extract derived from corn seed coat (Nisshoku CELLFER, Nihon Shokuhin Kako; "CELLFER" is a trademark of this company), as the sole carbon source was prepared, and enrichment culture was carried out using about 50 kinds of soil samples sampled in Japan. The culture medium for enrichment culture was prepared by dissolving $NH_4NO_3$ 1.0 g, $K_2HPO_4$ 1.0 g, $NaH_2PO_4.2H_2O$ 1.3 g, $MgSO_4$. $7H_2O$ 0.2 g, $FeSO_4.7H_2O$ 0.01 g, $MnSO_4.7H_2O$ 0.01 g, $ZnSO_4.7H_2O$ 0.01 g, $CaCl_2$).$2H_2O$ 0.01 g, and Nisshoku CELLFER 2 g in ultra pure water to a volume of 1.0 L. The pH of this culture medium was 6.7. Hereinafter, this culture medium is referred to as corn NSP-containing enrichment culture medium. A solid culture medium obtained by adding agar to this culture medium is referred to as corn NSP-containing enrichment culture solid medium. In addition, for the purpose of observing the activity of xylanase produced by microorganisms grown on the solid medium based on halo, a culture medium containing 0.5% insoluble xylan derived from Oat spelt (Sigma) instead of Nisshoku CELLFER was prepared. Upon preparation, xylan particles were homogenized by ultrasonication using an ultrasonic cleaner (FU-10C, TGK). Hereinafter, this culture medium is referred to as Oat spelt xylan-containing enrichment culture solid medium.

One spatulaful of each soil sample was suspended in 1 mL of sterilized water, and left to stand for about 1 minute. A 50 μL-aliquot of the supernatant was collected, and inoculated to 2 mL of the corn NSP-containing enrichment culture medium in a culture test tube. Shaking culture was carried out at 160 rpm at a room temperature using a water bath shaker PERSONAL-11 (TAITEC). After culturing for 2 weeks or longer, culture test tubes were subjected to visual observations, and test tubes of which the turbidity of the culture medium due to corn NSP was lowered were selected.

(2) Measurement of Corn NSP Hydrolysis Activity by Dinitrosalicylic Acid Method

The culture broth was centrifuged (4° C., 20,400×g, 10 minutes), to obtain a culture supernatant. A hydrolysis reaction of corn NSP was carried out using this culture supernatant, and the amount of generated reduced termini was quantified by a coloring method using dinitrosalicylic acid (Sumner, J. B. et al., J. Biol. Chem. 65, 393-395, 1925). The procedure is shown below.

Corn NSP (Nisshoku CELLFER) was suspended in 50 mM Britton-Robinson buffer adjusted to pH 6.0 to a final concentration of 1.5%. This suspension was subjected to ultrasonication for 30 minutes using an ultrasonic cleaner, to obtain a substrate solution. An 80 μL-aliquot of the substrate solution was added with 20 μL of an enzyme sample (culture supernatant), and a reaction was carried out at 37° C. for 24 hours. After the enzymatic reaction, the reaction was terminated by addition of 100 μL of 1 M NaOH. An insoluble substrate was precipitated by centrifugation (4° C., 7,000×g, 5 minutes), and 100 μL of a supernatant was collected. This supernatant (100 μL) was added with 100 μL of a coloring reagent prepared by the method described in Sumner, J. B. et al., and the mixture was boiled at 100° C. for 5 minutes. After cooling with ice, the mixture was diluted with 550 μL of ultra pure water. The absorbance at a wavelength of 545 nm was measured, to quantify the amount of reduced termini generated by hydrolyzation of the substrate.

The corn NSP hydrolysis activity of each culture supernatant was measured as described above, test tubes showing the corn NSP hydrolysis activity were identified.

(3) Acquisition of Single Clone and Identification of Strain

The culture broths of the test tubes for which the corn NSP hydrolysis activity were observed were each applied to the corn NSP-containing enrichment culture solid medium, and cultured at a room temperature. The grown microorganism was suspended in sterilized water, and serially diluted. Each diluted suspension was applied to Oat spelt xylan-containing enrichment culture solid medium, and cultured at a room temperature. A single clone was obtained on the basis of a halo on the solid medium due to xylanase activity as an indicator, and designated as H2C strain.

Identification of the H2C strain was carried out on the basis of morphological observation, physiological and biochemical property test, and nucleotide sequence analysis of 16S rDNA. It was revealed that this strain is a gram-negative *bacillus* having motility, forms spores, and is positive for both catalase reaction and oxidase reaction. In addition to these properties, due to the fact or the like that this strain showed a high homology of 94.4 to 97.4% with the nucleotide sequence of the genus *Paenibacillus* in nucleotide sequence analysis of 16S rDNA, it was revealed that this strain should be classified as the genus *Paenibacillus*. Furthermore, a physiological and biochemical test using a bacteria identification test kit API 50 CHB (bioMerieux) was carried out. As a result, the H2C strain oxidized L-arabinose, D-xylose, glucose, and the like, did not oxidize glycerol, erythritol, D-arabinose, and the like, showed beta-galactosidase activity, did not produce acetoin, did not hydrolyze gelatin, and did not reduce nitrate. No known species of the genus *Paenibacillus* perfectly matched with these properties was found. From the above, while the H2C strain was considered to be included in the genus *Paenibacillus*, the results of the nucleotide sequence analysis of 16S rDNA and the physiological and biochemical property test indicate that the H2C strain is different from any known species of the genus *Paenibacillus*, and hence, there may be a possibility that the H2C strain constitutes a novel species of the genus *Paenibacillus*. Therefore, this strain was designated as *Paenibacillus* sp. H2C strain.

Example 2: Determination of Genome Sequence

The genome sequence of the H2C strain was determined using a next generation sequencer according to the following procedure.

The H2C strain was inoculated to 50 mL of LB medium, and cultured with shaking at 30° C. and 120 rpm for 2 days. Obtained cells were harvested by centrifugation, and the genomic DNA was extracted using Genomic tip 100/G (Qiagen) according to the attached manual. A library was prepared from the obtained genomic DNA using Nextera DNA Sample Prep Kit (Illumina), and the genome sequence was analyzed using a next generation sequencer MiSeq v2 (Illumina) and MiSeq Reagent Kit v2 500 cycle (Illumina). ORF prediction and annotation were carried out using Genaris Annotation System (Genaris). As a result of assembling of the obtained sequence, 109 contigs were obtained, and a nucleotide sequence of 6, 988, 404 bp was determined. As a result of gene identification, 6,128 CDSs were predicted.

Example 3: Identification of Enzymes (Xyn5A, Xyn10B, Xyn11A, and Xyn30A) Based on Corn NSP Hydrolysis Activity The culture supernatant of the H2C strain was fractionated on the basis of the corn NSP hydrolysis activity as an indicator, and enzymes having this activity and genes thereof were identified.

(1) Measurement Method of Corn NSP Hydrolysis Activity by Phloroglucinol-Acetate Method A reaction was carried out using corn NSP (Nisshoku CELLFER) as a substrate, and the amount of soluble arabinoxylan released from corn NSP was measured by phloroglucinol-acetate method (Sakka M. et al., Appl. Environ. Microbiol., 77(12):4260-4263, 2011), to thereby evaluate the enzyme activity. The procedure is shown below.

First, Nisshoku CELLFER was suspended in 50 mM Britton-Robinson buffer (pH 6.0) to a final concentration of 2.5%, to obtain a substrate solution. A 400 μL-aliquot of the substrate solution was added with 100 μL of an enzyme sample, and a reaction was carried out at 37° C. and pH 6.0 for 2 hours. After the enzymatic reaction, the reaction was terminated by boiling at 100° C. for 5 minutes. An insoluble substrate was precipitated by centrifugation (4° C., 7,000×g, 5 minutes), and 100 μL of a supernatant was recovered. Separately, a phloroglucinol-acetate reagent was prepared by mixing 11 mL of acetic acid, 0.2 mL of hydrochloric acid, 0.5 mL of ethanol solution containing 20% phloroglucinol (Tokyo Kasei), and 0.1 mL of 1.75% glucose solution. The aforementioned supernatant (100 μL) was added with 500 μL of the phloroglucinol-acetate reagent, and the mixture was boiled at 100° C. for 25 minutes. After cooling with ice, the absorbance at wavelengths of 552 nm and 510 nm was measured, and the difference thereof ($A_{552}$-$A_{510}$) was calculated. Similarly, a colorimetric reaction and absorbance measurement were carried out using a xylose solution as a standard instead of the supernatant, and a calibration curve was prepared on the basis of the $A_{552}$-$A_{510}$ value. The amount of pentose contained in each sample was calculated using this calibration curve, and taken as the amount of soluble arabinoxylan produced by hydrolysis by the enzymatic reaction.

(2) Preparation of Culture Supernatant of H2C Strain

LB medium was used for culturing the H2C strain. As an inducer, corn NSP (Nisshoku CELLFER) was added to a final concentration of 0.2%. Culture was carried out with shaking at 30° C. using a shaking culture apparatus (Able, ML-316). After 48 hours, 1.5 L of a culture broth of the H2C strain was obtained. The culture broth was centrifuged (4° C., 29,100×g, 10 minutes), and the obtained supernatant was subjected to filter filtration (0.20 μm). Ammonium sulfate was added and dissolved to the supernatant to a final concentration of 0.7 M, and the resulting precipitate was removed by centrifugation (4° C., 29,100×g, 10 minutes). The obtained supernatant was subjected to filter filtration (0.20 μm), and used as a starting material for enzyme purification.

(3) Fractionation by Column Chromatography

Fractionation and purification of the enzyme was carried out by a combination of various kinds of column chromatography shown below. The corn NSP hydrolysis activity of obtained fractions was measured by the phloroglucinol-acetate method.

(a) Hydrophobic Interaction Chromatography Using HiLoad 16/10 Phenylsepharose

The sample was applied to HiLoad 16/10 Phenylsepharose column (GE Healthcare) equilibrated with 0.05 M Tris-HCl buffer (pH 7.0) containing 0.7 M ammonium sulfate. After washing the column with the same buffer, adsorbed proteins were eluted with an ammonium sulfate linear concentration gradient of 0.7 to 0 M.

(b) Anion Exchange Chromatography Using HiTrap Q HP

The buffer of the sample was exchanged for 20 mM Tris-HCl buffer (pH 8.0) using a centrifugal filter unit (Amicon Ultra-15, 10 kDa, Merck Millipore). This sample was applied to HiTrap Q HP, 5 mL column (GE Healthcare) equilibrated with the same buffer. After washing the column with the same buffer, adsorbed proteins were eluted with an NaCl linear concentration gradient of 0 to 1 M.

(c) Cation Exchange Chromatography Using HiTrap SP HP

The buffer of the sample was exchanged for 50 mM MES sodium buffer (pH 6.0) using Amicon Ultra-15, 10 kDa. This sample was applied to HiTrap SP HP, 5 mL column (GE Healthcare) equilibrated with the same buffer. After washing the column with the same buffer, adsorbed proteins were eluted with an NaCl linear concentration gradient of 0 to 1 M.

(d) Gel Filtration Chromatography Using HiLoad 16/600 Superdex 200 pg

The sample was concentrated using Amicon Ultra-15, 10 kDa. This sample was applied to HiLoad 16/600 Superdex 200 pg column (GE Healthcare) equilibrated with 20 mM Tris-HCl buffer (pH 7.0) containing 100 mM NaCl, and eluted with the same buffer.

(4)N-Terminal Amino Acid Sequence Analysis

The sample was concentrated using Amicon Ultra-15, 10 kDa, and separated by electrophoresis using 4-20% mini-protean TGX precast gel (Bio-Rad). Separated proteins were transferred from the gel to a PVDF membrane (Min iBlot Gel Transfer Stacks, Thermo Fisher Scientific) using iBlot Dry Blotting system (Thermo Fisher Scientific), and then stained using CBB Stain One (Nacalai Tesque). Bands were excised, and the N-terminal amino acid sequence was determined using a protein sequencer (Procise 492H, Applied Biosystems).

(5) Purification of Each Enzyme (a) Xyn5A and Xyn10B

The sample prepared in (2) was subjected to HiLoad 16/10 Phenylsepharose column chromatography. As a result, two fractions eluted at ammonium sulfate concentrations of 0.05 M and 0.45 M showed a high corn NSP hydrolysis activity. Furthermore, the fraction eluted at an ammonium sulfate concentration of 0.05 M was collected, subjected to buffer exchange, and then subjected to HiTrap Q HP column chromatography. As a result, corn NSP hydrolysis activity was confirmed in a non-adsorbed fraction. Furthermore, when this non-adsorbed fraction was subjected to HiTrap SP HP column chromatography, corn NSP hydrolysis activity was confirmed in a non-adsorbed fraction. Furthermore, when this non-adsorbed fraction was separated by SDS-PAGE, a plurality of bands was confirmed. As a result of N-terminal amino acid analysis of each band, partial sequences shown in SEQ ID NO: 1 and SEQ ID NO: 2 were obtained.

As a result of searching for these partial sequences in protein sequences presumed to be encoded by the genome of the H2C strain, the partial sequence shown in SEQ ID NO: 1 matched with the amino acid sequence of positions 1 to 8 of SEQ ID NO: 4 encoded by the nucleotide sequence of SEQ ID NO: 3. Because this protein of SEQ ID NO: 4 has high homology with proteins of GH family 5, it was designated as Xyn5A. From the result of N-terminal amino acid analysis, it was presumed that the amino acid sequence of the mature protein of Xyn5A corresponds to positions 1 to 535 of SEQ ID NO: 4 and is encoded by the nucleotide sequence of positions 115 to 1719 of SEQ ID NO: 3. In addition, the partial sequence shown in SEQ ID NO: 2 matched with the amino acid sequence of positions 1 to 15 of SEQ ID NO: 6 encoded by the nucleotide sequence of SEQ ID NO: 5. Because this protein of SEQ ID NO: 6 has high homology with proteins of GH family 10, it was designated as Xyn10B. From the result of N-terminal amino acid analysis, it was presumed that the amino acid sequence of the mature protein of Xyn10B corresponds to positions 1 to 448 of SEQ ID NO: 6 and is encoded by the nucleotide sequence of positions 136 to 1479 of SEQ ID NO: 5. The positions −38 to −1 of SEQ ID NO: 4 and the positions −45 to −1 of SEQ ID NO: 6 are presumed to be signal peptides.

(b) Xyn11A

A fraction eluted with an ammonium sulfate concentration of 0.45 M in HiLoad 16/10 Phenylsepharose column chromatography in (a) was collected, subjected to buffer exchange, and then subjected to HiTrap SP HP column chromatography. As a result of subjecting an eluted fraction showing corn NSP hydrolysis activity to SDS-PAGE, a single band was confirmed. As a result of N-terminal amino acid analysis of this band, a partial sequence shown in SEQ ID NO: 7 was obtained. As a result of searching for this partial sequence in protein sequences presumed to be encoded by the genome of the H2C strain, the partial sequence matched with the amino acid sequence of positions 29 to 38 of SEQ ID NO: 9 encoded by the nucleotide sequence of SEQ ID NO: 8. Because this protein has high homology with proteins of GH family 11, it was designated as Xyn11A. From the result of N-terminal amino acid analysis, it was presumed that the amino acid sequence of the mature protein of Xyn11A corresponds to positions 1 to 183 of SEQ ID NO: 9 and is encoded by the nucleotide sequence of positions 85 to 633 of SEQ ID NO: 8. The positions −28 to −1 of SEQ ID NO: 9 are presumed to be a signal peptide.

(c) Xyn30A

As a result of HiTrap SP HP column chromatography in (b), corn NSP hydrolysis activity was confirmed also in a non-adsorbed fraction. The obtained non-adsorbed fraction was subjected to HiTrap Q HP column chromatography, and a non-adsorbed fraction was further subjected to HiLoad 16/600 Superdex 200 pg column chromatography. As a result of subjecting an eluted fraction showing corn NSP hydrolysis activity to SDS-PAGE, a single band was confirmed. As a result of N-terminal amino acid analysis of this band, a partial sequence shown in SEQ ID NO: 10 was obtained. As a result of searching for this partial sequence in protein sequences presumed to be encoded by the genome of the H2C strain, the partial sequence matched with the amino acid sequence of positions 37 to 50 of SEQ ID NO: 12 encoded by the nucleotide sequence of SEQ ID NO: 11. Because this protein has high homology with proteins of GH family 30, it was designated as Xyn30A. From the result of N-terminal amino acid analysis, it was presumed that the amino acid sequence of the mature protein of Xyn30A corresponds to positions 1 to 527 of SEQ ID NO: 12 and is encoded by the nucleotide sequence of positions 109 to 1689 of SEQ ID NO: 11. The positions −36 to −1 of SEQ ID NO: 12 are presumed to be a signal peptide.

(d) Xyn43A

As a result of analyzing the genomic sequence of the H2C strain, a gene of an enzyme having high homology with GH family 43 enzymes, and this enzyme was designated as Xyn43A. As shown in Example 9, it is presumed that the amino acid sequence of SEQ ID NO: 14 is the amino acid sequence of Xyn43A precursor (pro sequence). It was presumed that the amino acid sequence of the mature protein of Xyn43A corresponds to positions 1 to 608 of SEQ ID NO: 14 and is encoded by the nucleotide sequence of positions 79 to 1902 of SEQ ID NO: 13. The positions −26 to −1 of SEQ ID NO: 14 are presumed to be a signal peptide.

Example 4: Preparation of NSP Degrading Enzymes in *E. coli*

Recombinant enzymes of the four enzymes identified from the culture supernatant of the H2C strain and the Xyn43A identified by genome analysis were prepared. These enzymes are also referred to as NSP degrading enzymes.

(1) Construction of Expression Strains for Xyn10B, Xyn11A, Xyn30A, and Xyn43A

By using the genomic DNA of the H2C strain as a template and primers P1 and P2 (SEQ ID NOs: 15 and 16), a region containing a nucleotide sequence encoding Xyn10B was PCR-amplified. PCR-amplification was carried out using PrimeStar Max (Takara Bio). The reaction solution was prepared according to the composition attached to the kit, and 30 cycles of reaction at 98° C. for 10 seconds, 55° C. for 10 seconds, and 68° C. for 10 seconds were carried out. The obtained PCR fragment was ligated with pET-21b (+) vector (Merck Millipore) digested with NdeI and XhoI using In-Fusion HD Cloning Kit (Clontech). *E. coli* JM109 was transformed with this ligation reaction solution, and an objective plasmid was extracted from an ampicillin resistant strain. *E. coli* BL21(DE3) was transformed with this plasmid, to obtain an expression strain of Xyn10B. Similarly, an expression strain of Xyn11A was obtained by using primers P3 and P4 (SEQ ID NOs: 17 and 18), an expression strain of Xyn30A was obtained by using primers P5 and P6 (SEQ ID NOs: 19 and 20), and an expression strain of Xyn43A was obtained by using primers P7 and P8 (SEQ ID NOs: 21 and 22). In these expression strains, proteins with His-tag added to the C-terminus of the mature proteins are expressed for Xyn10B, Xyn11A, and Xyn30A, and a protein with His-tag added to the C-terminus of the precursor protein containing the signal peptide is expressed for Xyn43A. Incidentally, it is presumed that the signal peptide of Xyn43A is cleaved after expression and a mature protein is generated.

(2) Construction of Expression Strain of Xyn5A

By using the genomic DNA of the H2C strain as a template and primers P9 and P10 (SEQ ID NOs: 23 and 24), PCR-amplification was carried out under the same conditions as (1). The obtained PCR fragment was ligated with pETDuet-1 vector (Merck Millipore) digested with BamHI and HindIII using In-Fusion HD Cloning Kit (Clontech). *E. coli* JM109 was transformed with this ligation reaction solution, and an objective plasmid was extracted from an ampicillin resistant strain. *E. coli* BL21(DE3) was transformed with this plasmid, to obtain an expression strain of Xyn5A. In this expression strain, Xyn5A added with His-tag at the N-terminus is expressed.

(3) Construction of Expression Strain of *Fusarium verticillioides* Xylanase in *E. coli*

As a control, a strain expressing Fvexyn4, a xylanase derived from *Fusarium verticillioides* described in WO2014/020142, in *E. coli* was constructed, and a purified enzyme was prepared. First, the nucleotide sequence of Fvexyn4 gene described in SEQ ID NO: 6 of WO2014/020142 was codon-optimized for *E. coli*, NdeI site was added upstream thereof and XhoI site was added downstream thereof. Synthesis of the resulting nucleotide sequence was outsourced to GenScript, to obtain the resulting nucleotide sequence in a form inserted in EcoRV site of pUC57 vector. Next, the plasmid was treated with the restriction enzymes NdeI and XhoI, subjected to agarose gel electrophoresis, and a DNA fragment containing the Fvexyn4 gene was recovered from the gel. The DNA fragment was ligated to pET21-b(+) treated with NdeI and XhoI using DNA Ligation Kit (Takara Bio), to prepare an expression plasmid. *E. coli* JM109 was transformed with this ligation reaction solution, and an objective plasmid was extracted from an ampicillin resistant strain. *E. coli* BL21 (DE3) was transformed with this plasmid, to obtain an expression strain of Fvexyn4. In this expression strain, Fvexyn4 added with His-tag at the C-terminus is expressed.

(4) Purification of Recombinant Enzymes

Each expression strain was grown in LB medium containing 100 mg/L ampicillin at 37° C. for 6 hours. A 1.6 mL-aliquot of the obtained culture broth was inoculated into 160 mL of Overnight Express Instant TB Medium (Merck) containing 100 mg/L ampicillin, and shaking culture was carried out using a Sakaguchi flask. The culture conditions were set to 30° C. for 18 hours for Xyn5A and Xyn30A, and 18° C. for 40 hours for Xyn11A, Xyn10B, Xyn43A, and FveXyn4.

After completion of the culture, cells were harvested from the obtained culture broth by centrifugation, suspended in a buffer solution consisting of 20 mM Tris-HCl (pH 7.6), 300 mM NaCl, and 10 mM imidazole, and subjected to ultrasonic disruption. Cell debris was removed from the disrupted solution by centrifugation, and the obtained supernatant was taken as a soluble fraction.

The obtained soluble fraction was applied to a His-tag protein purification column HisTALON Superflow Cartridge (CV=5 mL, Clontech; HisTALON and Superflow are trademarks of this company) equilibrated with the aforementioned buffer solution, to allow adsorption on the carrier. Proteins not adsorbed on the carrier (non-adsorbed proteins) were washed off with the aforementioned buffer solution, and then adsorbed proteins were eluted with a solution identical to the aforementioned buffer solution except that imidazole concentration was changed to 150 mM at a flow rate of 5 mL/min.

Eluted fractions containing the enzyme were collected, and buffer-exchanged into 50 mM Britton-Robinson buffer (pH 6.0) using Amicon Ultra-15, 10 kDa, to obtain a purified enzyme solution.

As a control, xylanase was purified from Econase XT (ABVista; Econase is a trademark of this company), which is commercially available as a feed enzyme, according to the method of WO2014/020142.

The concentration of each obtained purified enzyme was measured using Protein Assay Lowry Kit (Nacalai Tesque) with Quick Start BSA Standard set (Bio-Rad) as a standard.

Example 5: Evaluation of Beta-1,4-Xylanase Activity of Xyn5A, Xyn10B, Xyn11A, and Xyn30A Xylanase activity of each purified enzyme of Xyn5A, Xyn10B, Xyn11A, and Xyn30A prepared in Example 4 was evaluated. Beechwood-derived soluble xylan (Sigma, X4252) and insoluble wheat arabinoxylan (Megazyme, P-WAXYI) were used as a substrate for activity evaluation, and the amount of reducing termini generated by the enzymatic reaction was evaluated. Each of these substrates is a polysaccharide having beta-1,4-linked xylose as the main chain. The procedure is shown below.

First, these substrates were each suspended in 50 mM Britton-Robinson buffer adjusted to pH 6.0 to a final concentration of 1.875%, and the suspension was subjected to ultrasonication for 30 minutes using an ultrasonic cleaner, to obtain a substrate solution. An 80 μL-aliquot of this substrate solution was added with 20 μL of a diluted solution of the purified enzyme solution prepared in Example 4, and a reaction was carried out at 37° C. for 10 minutes. As a blank sample, the reaction was carried out using 50 mM Britton-Robinson buffer (pH 6.0) instead of the enzyme solution. After the enzymatic reaction, the reaction was terminated by addition of 100 μL of 1 M NaOH. An insoluble substrate was precipitated by centrifugation (4° C., 20,400×g, 10 minutes), and a supernatant was recovered. The amount of reduced termini in this supernatant was quantified by the dinitrosalicylic acid method in the same manner as in Example 1. A colorimetric reaction and absorbance measurement were similarly carried out using a xylose solution as a standard, to prepare a calibration curve. The amount of reduced termini generated by hydrolysis of the substrate was quantified using this calibration curve. The amount of reduced termini in the blank sample was subtracted from the amount of reduced termini in each sample, to calculate the amount of reduced termini generated by the enzymatic reaction.

The reducing termini-generating activity of each NSP-degrading enzyme is shown in Table 1. Xyn5A showed the reducing termini-generating activity only against insoluble wheat arabinoxylan, and Xyn30A showed the reducing termini-generating activity only against beechwood xylan. Xyn10B and Xyn11A showed the reducing termini-generating activity against both substrates. These results revealed that these four enzymes have beta-1,4-xylanase activity.

TABLE 1

| | Reducing termini-generating activity against each substrate (μmol/min/mg) | |
|---|---|---|
| | Beechwood xylan | Insoluble wheat arabinoxylan |
| Xyn5A | 0.00 | 4.62 |
| Xyn10B | 85.9 | 41.1 |
| Xyn11A | 140.5 | 43.7 |
| Xyn30A | 17.6 | 0.00 |

Example 6: Evaluation of Alpha-L-Arabinofuranosidase Activity of Xyn43A

It has been reported that GH family 43, to which Xyn43A is considered to belong, has alpha-L-arabinofuranosidase activity which releases side chain arabinose from arabinoxylan (Lagaert et al., Biotechnology Advances 32, 316-332, 2014). Therefore, in order to confirm the arabinofuranosidase activity possessed by Xyn43A, insoluble wheat arabinoxylan (Megazyme, P-WAXYI) decomposition reaction by Xyn43A was carried out, to evaluate the release of arabinoxylan. Wheat arabinoxylan has a structure in which arabinofuranose (arabinose) residues are bound to the xylan main chain via α-1,2 bond and/or α-1,3 bond.

An enzymatic reaction using insoluble wheat arabinoxylan as a substrate was carried out using a diluted solution of the purified enzyme solution of Xyn43A prepared in Example 4 in the same manner as in Example 5, and a supernatant was recovered. This supernatant was diluted, and separated using an ion chromatograph for saccharide analysis (Thermo Fisher Scientific, Dionex ICS-5000+). CarboPac SA10-4 μm (Thermo Fisher Scientific) was used as the column, and 1 mM potassium hydroxide was used for elution. Separated saccharides were detected by pulsed amperometric detection (PAD) method. Separately, standards for xylose, arabinose, and glucose were separated under the same conditions, and the concentration of each component contained in the sample was quantified.

The results are shown in FIG. 1. A peak was detected at the same retention time as that of the arabinose standard in the reaction supernatant after the reaction using Xyn43A, whereas no peak was detected in the blank sample. From the above, it was shown that Xyn43A has alpha-L-arabinofuranosidase activity. The amount of generated arabinose was quantified, and the arabinose release activity per enzyme weight was calculated to be 2.0 μmol/min/mg.

Example 7: Evaluation of Corn NSP Degradation Activity of Each NSP Degrading Enzyme (1) DDGS Decomposition Reaction Regarding the activity of each NSP degrading enzyme, the activity to decompose and solubilize insoluble arabinoxylan contained in corn was evaluated. The procedure is shown below.

First, corn DDGS, which is commercially available as a feed, was pulverized, and then passed through a sieve of 0.25 mm mesh. Next, in order to preliminarily remove soluble arabinoxylan contained in the corn DDGS, 500 mg of the corn DDGS was weighed in a 50 mL tube (Falcon), suspended in 20 mL of distilled water, and stirred at 37° C. for 30 minutes. DDGS was recovered by centrifugation (8,000 rpm, 10 minutes), and the supernatant was removed.

The recovered DDGS was suspended in 10 mL of 100 mM Britton-Robinson buffer (pH 6.5), and added with distilled water to a volume of 18 mL. This DDGS suspension was dispensed into 1.5 mL tubes by 0.45 mL per tube while stirring. The purified enzyme solution prepared in Example 4 was diluted with 50 mM Britton-Robinson buffer (pH 6.5) to a final concentration of 100 μg-protein/mL, to obtain a diluted enzyme solution. The diluted enzyme solution was dispensed into the DDGS suspension in the 1.5 mL tubes by 0.05 mL per tube so that the total amount became 0.5 mL (the enzyme concentration in the reaction solution was 10 μg/mL, the DDGS concentration in the reaction solution was about 25 mg/mL). These tubes were placed on a rotator and agitated for 5 hours in an incubator at 37° C., to carry out decomposition reaction of DDGS. A reaction was carried out in triplicate for each enzyme. As a control, a reaction in which 50 mM Britton-Robinson buffer (pH 6.5) was added instead of the diluted enzyme solution was also carried out. In addition, in order to evaluate the effect of mixing enzymes, a reaction was also carried out using a composition in which two kinds of diluted enzyme solutions were mixed in equal amounts (each enzyme was contained 5 μg/mL in the reaction solution, and the total enzyme concentration was 10 μg/mL).

After the reaction, the reaction was terminated by heating each tube at 100° C. for 2 minutes. Furthermore, the reaction solution was centrifugally filtered using Ultrafree-MC Centrifugal Filter Unit (Merck Millipore) having a pore diameter of 0.22 μm to remove DDGS, and a filtrate was recovered and used as a soluble fraction.

(2) Measurement of Amount of Arabinoxylan Contained in Soluble Fraction

The soluble fraction was mixed with 0.4 M sulfuric acid, and hydrolyzed by heating at 125° C. for 1 hr. This hydrolysate was separated using an ion chromatograph for saccharide analysis in the same manner as in Example 6, and the concentrations of xylose and arabinose were quantified. The total value of the concentrations of xylose and arabinose contained in the soluble fraction was taken as the free arabinoxylan concentration.

Figure 2:
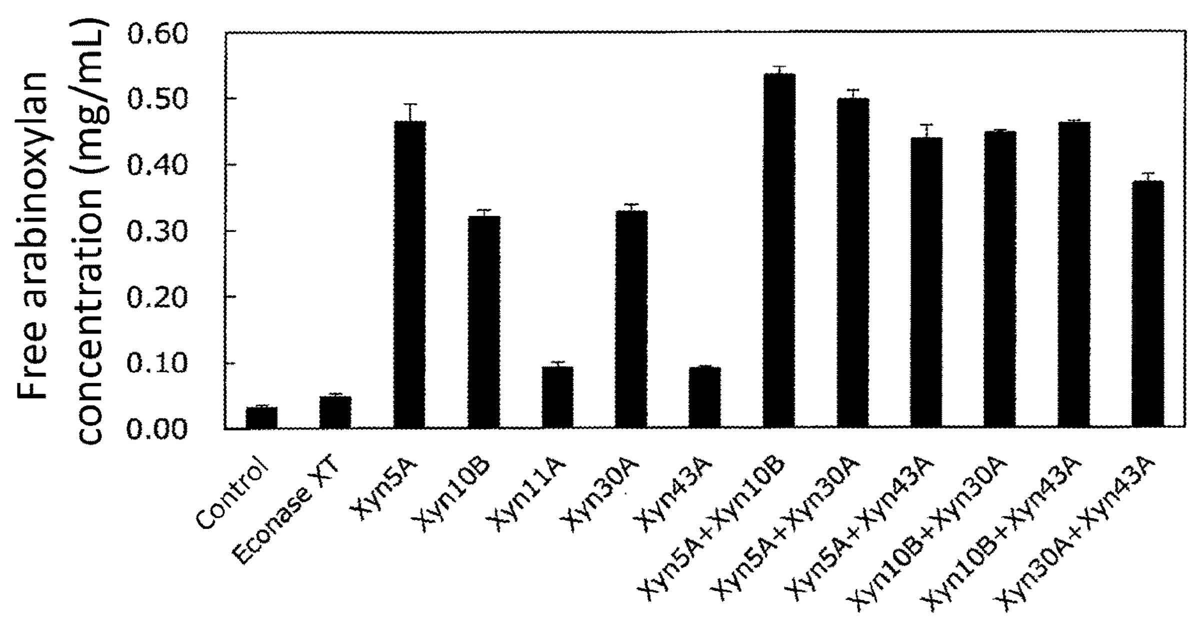
FIG. 2 shows a diagram showing release of soluble arabinoxylan from corn DDGS by various enzymes (enzyme concentration=10 μg/mL).

The results are shown in FIG. 2 (N=3, error bars each represent standard deviation). It was confirmed that all of the NSP degrading enzymes derived from *Paenibacillus* sp. H2C strain had the activity of releasing arabinoxylan from corn DDGS. In addition, it was shown that all of these enzymes are able to release a larger amount of arabinoxylan as compared to the xylanase purified from Econase XT. Furthermore, mixing of different enzymes enabled release of a larger amount of arabinoxylan than that observed when one enzyme was allowed to act solely.

Example 8: Evaluation of Addition Concentration of NSP Degrading Enzyme and Free Arabinoxylan Concentration In order to evaluate the relationship between the enzyme concentration and the free arabinoxylan concentration from DDGS, the corn DDGS degradation activity under conditions of enzyme concentration lower that in Example 7 was evaluated.

The reaction was carried out in the same manner as in Example 7(1), using a solution obtained by diluting the purified enzyme solution prepared in Example 4 to a final concentration of 0.1 μg/mL or 1 μg/mL (the enzyme concentration in the reaction solution is 10 ng/mL or 100 ng/mL). In addition, the arabinoxylan concentration contained in the soluble fraction was quantified by the same method as in Example 7(2).

Figure 3:
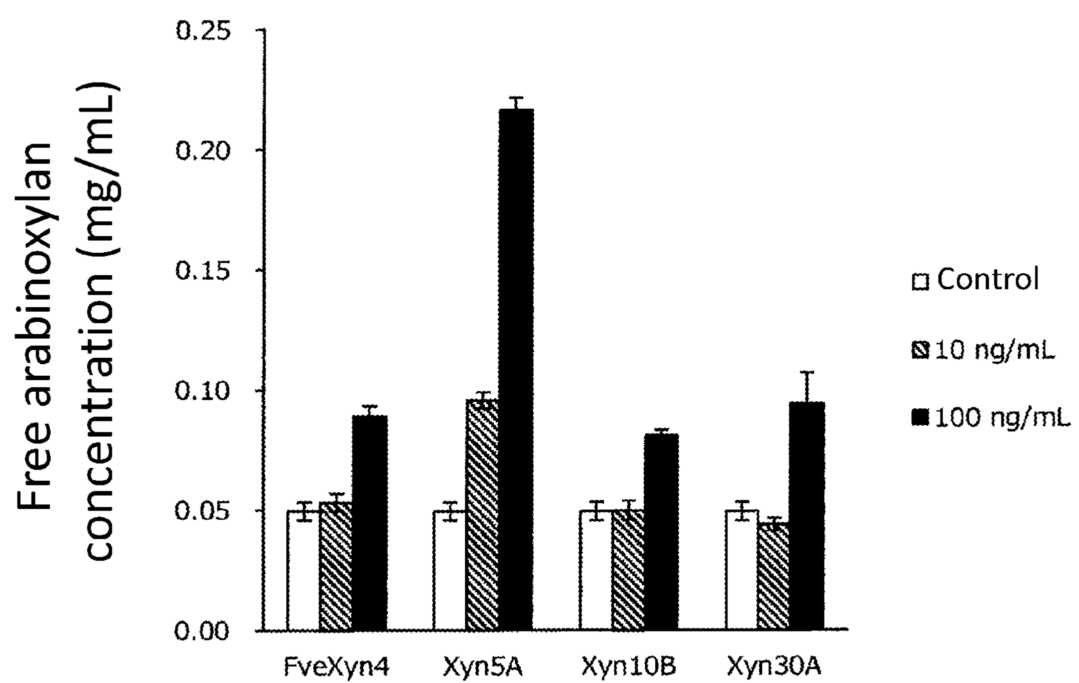
FIG. 3 shows a diagram showing release of soluble arabinoxylan from corn DDGS under different enzyme concentrations.

The results are shown in FIG. 3 (N=3, error bars each represent standard deviation). It was shown that Xyn5A release a larger amount of arabinoxylan from DDGS as compared to FveXyn4 under any conditions of enzyme concentrations of 10 ng/mL or 100 ng/mL.

Example 9: Analysis of N-Terminus of Xyn43A Mature Protein

Xyn43A purified in the same manner as in Example 4 was concentrated by ultrafiltration, subjected to SDS-PAGE using Mini-Protean TGX Precast Gels 4-20% (Bio-Rad), and then transferred to a PVDF membrane using iBlot Gel Transfer Stacks (Thermo Fisher Scientific) and iBlot Dry Blotting system. The PVDF membrane was stained using CBB (CBB Stain One, Nacalai Tesque), a band was excised, and the N-terminal amino acid sequence of 10 amino acids was determined using a protein sequencer (Procise 492H, Applied Biosystems). The result is shown in SEQ ID NO: 25. As a result of comparison with the amino acid sequence of Xyn43A shown in SEQ ID NO: 14, 7 amino acids matched with the amino acid sequence of positions 27 to 36 from the N terminus (positions 1 to 10 in SEQ ID NO: 14). From the above, it was inferred that cleavage occurs between Ala at position 26 from the N terminus (position −1 in SEQ ID NO: 14) and Ala at position 27 from the N terminus (position 1 in SEQ ID NO: 14), to thereby generate a mature protein. A possible example of the reason why the amino acid sequences do not completely match is contamination of the purified enzyme with the precursor.

Example 10: Preparation of Xyn5A Homologues in *E. coli*

(1) Acquisition of Amino Acid Sequences of P1XP2_GH5, JDR-2_GH5, and BcGH5

In order to search for enzymes having the same function as Xyn5A of the H2C strain, a search based on BlastP (blast.ncbi.nlm.nih.gov/Blast.cgi?PAGE=Proteins) was carried out for databases of published sequence information using the amino acid sequence of Xyn5A mature protein as a query, to thereby obtain amino acid sequences highly homologous to the amino acid sequence of Xyn5A. As for these amino acid sequences, the secretory signal peptide sequence was predicted using SignalP (cbs.dtu.dk/services/SignalP). Three of them are shown in Table 2. The enzymes of these amino acid sequences were designated as P1XP2_GH5, JDR-2_GH5, and BcGH5. In the table, the column titled "Identity" shows the amino acid sequence identity to Xyn5A.

TABLE 2

Sequences highly homologous to Xyn5A

| Enzyme name | Source | Accession number | Identity (%) | Amino acid sequence (signal sequence/ mature protein) | Nucleotide sequence (mature protein) |
|---|---|---|---|---|---|
| P1XP2_GH5 | *Paenibacillus* sp. P1XP2 | KHF37231.1 | 83 | SEQ ID NO: 26 (positions −29 to −1/ positions 1 to 536) | SEQ ID NO: 27 (positions 88 to 1695) |
| JDR-2_GH5 | *Paenibacillus* sp. JDR-2 | ACT02895.1 | 82 | SEQ ID NO: 28 (positions −32 to −1/ positions 1 to 536) | SEQ ID NO: 29 (positions 97 to 1704) |
| BcGH5 | *Bacillus caseinilyticus* | SDZ01154.1 | 77 | SEQ ID NO: 30 (positions −29 to −1/ positions 1 to 536) | SEQ ID NO: 31 (positions 88 to 1695) |

(2) Construction of Expression Strains of P1XP2_GH5, JDR-2_GH5, and BcGH5 in *E. coli*

The nucleotide sequence encoding the precursor proteins of P1XP2_GH5, JDR-2_GH5, and BcGH5 were codon-optimized for *E. coli*, NdeI site was added upstream thereof and XhoI site was added downstream thereof. Synthesis of the resulting nucleotide sequences was outsourced to Eurofins Genomics, to obtain the resulting nucleotide sequences in a form inserted in pTAKN-2 vector for P1XP2_GH5 and JDR-2_GH5, or in pEX-K4J1 vector for BcGH5. Next, the plasmids were each treated with the restriction enzymes NdeI and XhoI, subjected to agarose gel electrophoresis, and a DNA fragment containing each gene was recovered from the gel. The DNA fragment was ligated to pET21-b(+) treated with NdeI and XhoI using DNA Ligation Kit (Takara Bio), to prepare an expression plasmid. *E. coli* JM109 was transformed with this ligation reaction solution, and an objective plasmid was extracted from an ampicillin resistant strain. *E. coli* BL21(DE3) was transformed with these plasmids, to obtain expression strains of P1XP2_GH5, JDR-2_GH5, and BcGH5. In these expression strains, the precursor proteins of P1XP2_GH5, JDR-2_GH5, and BcGH5 including a signal peptide and added with His-tag at the C-terminus are expressed. Incidentally, it is presumed that these signal peptides are cleaved after expression and mature proteins are generated.

(3) Purification of Recombinant Enzymes

Each expression strain was grown in LB medium containing 100 mg/L ampicillin at 37° C. for 6 hours. A 1.6 mL-aliquot of the obtained culture broth was inoculated into 160 mL of Overnight Express Instant TB Medium (Merck) containing 100 mg/L ampicillin, and shaking culture was carried out using a Sakaguchi flask. The culture conditions were set to 30° C. for 18 hours.

After completion of the culture, cells were harvested from the obtained culture broth by centrifugation, suspended in a buffer solution consisting of 20 mM Tris-HCl (pH 7.6), 300 mM NaCl, and 10 mM imidazole, and subjected to ultrasonic disruption. Cell debris was removed from the disrupted solution by centrifugation, and the obtained supernatant was taken as a soluble fraction.

The obtained soluble fraction was applied to a His-tag protein purification column HisTALON Superflow Cartridge (CV=5 mL, Clontech; HisTALON and Superflow are trademarks of this company) equilibrated with the aforementioned buffer solution, to allow adsorption on the carrier. Proteins not adsorbed on the carrier (non-adsorbed proteins) were washed off with the aforementioned buffer solution, and then adsorbed proteins were eluted with a solution identical to the aforementioned buffer solution except that imidazole concentration was changed to 150 mM at a flow rate of 5 mL/min.

Eluted fractions containing the enzyme were collected, and buffer-exchanged into 50 mM Britton-Robinson buffer (pH 6.0) using Amicon Ultra-15, 10 kDa, to obtain a purified enzyme solution.

The concentration of each purified enzyme obtained was measured using Protein Assay Lowry Kit (Nacalai Tesque) with Quick Start BSA Standard set (Bio-Rad) as a standard.

Example 11: Evaluation of Beta-1,4-Xylanase Activity of P1XP2_GH5, JDR-2_GH5, and BcGH5

Xylanase activity of each purified enzyme of P1XP2_GH5, JDR-2_GH5, and BcGH5 prepared in Example 10 was evaluated. Insoluble wheat arabinoxylan (Megazyme, P-WAXYI) was used as a substrate for activity evaluation, and the amount of reducing termini generated by the enzymatic reaction was evaluated. The procedure is shown below.

First, these substrates were each suspended in 50 mM Britton-Robinson buffer adjusted to pH 6.0 to a final concentration of 1.875%, and the suspension was subjected to ultrasonication for 30 minutes using an ultrasonic cleaner, to obtain a substrate solution. An 80 μL-aliquot of this substrate solution was added with 20 μL of a diluted solution of the purified enzyme solution prepared in Example 10, and a reaction was carried out at 37° C. for 10 minutes. As a blank sample, the reaction was carried out using 50 mM Britton-Robinson buffer (pH 6.0) instead of the enzyme solution. After the enzymatic reaction, the reaction was terminated by addition of 100 μL of 1 M NaOH. An insoluble substrate was precipitated by centrifugation (4° C., 20,400×g, 10 minutes), and a supernatant was recovered. The amount of reduced termini in this supernatant was quantified by the dinitrosalicylic acid method in the same manner as in Example 1. A colorimetric reaction and absorbance measurement were similarly carried out using a xylose solution as a standard, to prepare a calibration curve. The amount of reduced termini generated by hydrolysis of the substrate was quantified using this calibration curve. The amount of reduced termini in the blank sample was subtracted from the amount of reduced termini in each sample, to calculate the amount of reduced termini generated by the enzymatic reaction.

The reducing termini-generating activity of each enzyme is shown in Table 3. All of these enzymes showed the reducing termini-generating activity, and hence, it was revealed that these three enzymes have beta-1,4-xylanase activity.

TABLE 3

Reducing termini-generating activity of each enzyme against wheat arabinoxylan

| Enzyme name | Activity (μmol/min/mg) |
|---|---|
| P1XP2_GH5 | 20.0 |
| JDR-2_GH5 | 21.5 |
| BcGH5 | 20.8 |

Example 12: Evaluation of Corn NSP Degradation Activity of P1XP2_GH5, JDR-2_GH5, and BcGH5

The reaction was carried out in the same manner as in Example 7(1), using each of solutions obtained by diluting the purified enzyme solution of Xyn5A prepared in Example 4 and the purified enzyme solutions prepared in Example 10 to a final concentration of 10 μg/mL (the enzyme concentration in the reaction solution is 1 μg/mL). However, the reaction period was changed to 2 hours. In addition, the arabinoxylan concentration contained in the soluble fraction was quantified by the same method as in Example 7(2).

Figure 4:
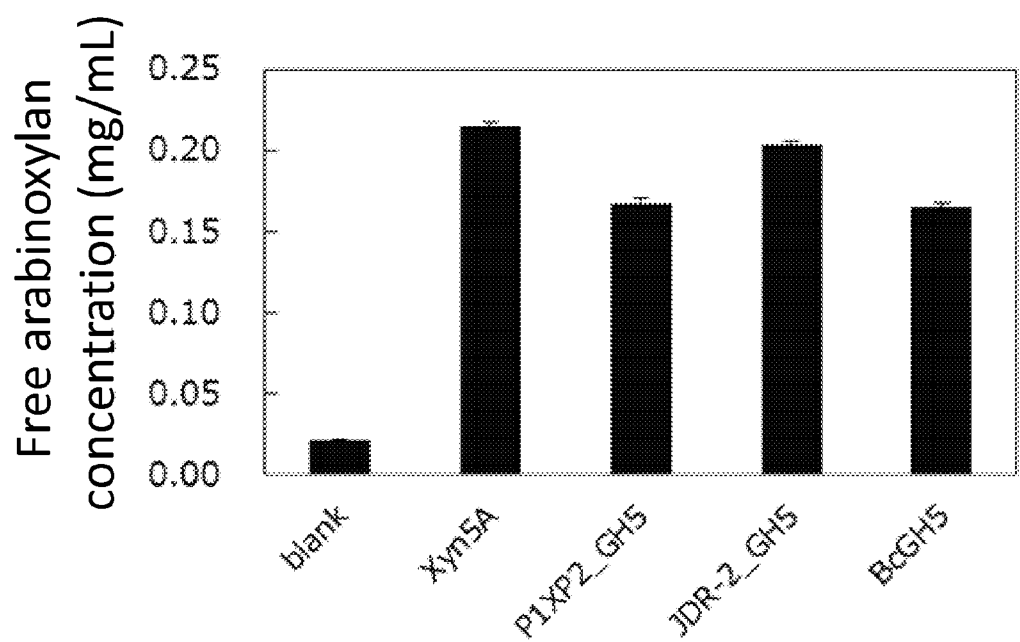
FIG. 4 shows a diagram showing release of soluble arabinoxylan from corn DDGS by various enzymes (enzyme concentration=1 μg/mL).

The results are shown in FIG. 4 (N=2, error bars each represent standard deviation). All of these enzymes released a larger amount of arabinoxylan than that observed for the case of the reaction without addition of enzyme (blank), and hence, it was revealed that they have an activity of releasing arabinoxylan from DDGS.

Example 13: Preparation of Xyn30A Homologues in *E. coli*

(1) Acquisition of Amino Acid Sequences of TCA20 GH30 and BaGH30

In order to search for enzymes having the same function as Xyn30A of the H2C strain, a search based on BlastP (https://blast.ncbi.nlm.nih.gov/Blast.cgi?PAGE=Proteins) was carried out for databases of published sequence information using the amino acid sequence of Xyn30A mature protein as a query, to thereby obtain amino acid sequences highly homologous to the amino acid sequence of Xyn30A. As for these amino acid sequences, the secretory signal peptide sequence was predicted using GENETYX Ver. 10 (Genetyx). Two of them are shown in Table 4. The enzymes of these amino acid sequences were designated as TCA20_GH30 and BaGH30. In the table, the column titled "Identity" shows the amino acid sequence identity to Xyn30A.

TABLE 4

| Sequences highly homologous to Xyn30A | | | | | |
|---|---|---|---|---|---|
| Enzyme name | Source | Accession number | Identity (%) | Amino acid sequence (signal sequence/ mature protein) | Nucleotide sequence (mature protein) |
| TCA20_GH30 | *Paenibacillus* sp. TCA20 | GAK42763.1 | 75 | SEQ ID NO: 32 (positions −30 to −1/ positions 1 to 529) | SEQ ID NO: 33 (positions 91 to 1677) |
| BaGH30 | *Bacillus amylo-liquefaciens* | KJD54725.1 | 78 | SEQ ID NO: 34 (positions −30 to −1/ positions 1 to 390) | SEQ ID NO: 35 (positions 91 to 1260) |

(2) Construction of Expression Strains of TCA20_GH30 and BaGH30 in *E. coli*

The nucleotide sequence encoding the mature proteins of TCA20 GH30 and BaGH30 were codon-optimized for *E. coli*, NdeI site was added upstream thereof and XhoI site was added downstream thereof. Synthesis of the resulting nucleotide sequences was outsourced to Eurofins Genomics, to obtain the resulting nucleotide sequences in a form inserted in pEX-K4J1 vector. Next, the plasmids were each treated with the restriction enzymes NdeI and XhoI, subjected to agarose gel electrophoresis, and a DNA fragment containing each gene was recovered from the gel. The DNA fragment was ligated to pET21-b(+) treated with NdeI and XhoI using DNA Ligation Kit (Takara Bio), to prepare an expression plasmid. *E. coli* JM109 was transformed with this ligation reaction solution, and an objective plasmid was extracted from an ampicillin resistant strain. *E. coli* BL21 (DE3) was transformed with these plasmids, to obtain expression strains of TCA20 GH30 and BaGH30. In these expression strains, the mature proteins of TCA20 GH30 and BaGH30 added with His-tag at the C-terminus are expressed.

(3) Purification of Recombinant Enzymes

Purified enzyme solutions were prepared using the expression strains constructed in (2) in the same manner as that in Example 10(3).

Example 14: Evaluation of Beta-1,4-Xylanase Activity of TCA20 GH30 and BaGH30

Xylanase activity of each purified enzyme of TCA20 GH30 and BaGH30 prepared in Example 13 was evaluated. Beechwood-derived xylan (Sigma, X4252) was used as a substrate for activity evaluation, and the evaluation was carried out in the same manner as that in Example 11.

The reducing termini-generating activity of each enzyme is shown in Table 5. All of these enzymes showed the reducing termini-generating activity, and hence, it was revealed that these two enzymes have beta-1,4-xylanase activity.

TABLE 5

| Reducing termini-generating activity of each enzyme against beechwood-derived xylan | |
|---|---|
| Enzyme name | Activity (μmol/ min/mg) |
| TCA20_GH30 | 27.3 |
| BaGH30 | 24.0 |

Example 15: Evaluation of corn NSP degradation activity of TCA20 GH30 and BaGH30

The reaction was carried out in the same manner as in Example 7(1), using each of solutions obtained by diluting the purified enzyme solution of Xyn30A prepared in Example 4 and the purified enzyme solutions prepared in Example 13 to a final concentration of 10 μg/mL (the enzyme concentration in the reaction solution is 1 μg/mL). However, the reaction period was changed to 2 hours. In addition, the arabinoxylan concentration contained in the soluble fraction was quantified by the same method as in Example 7(2).

Figure 5:
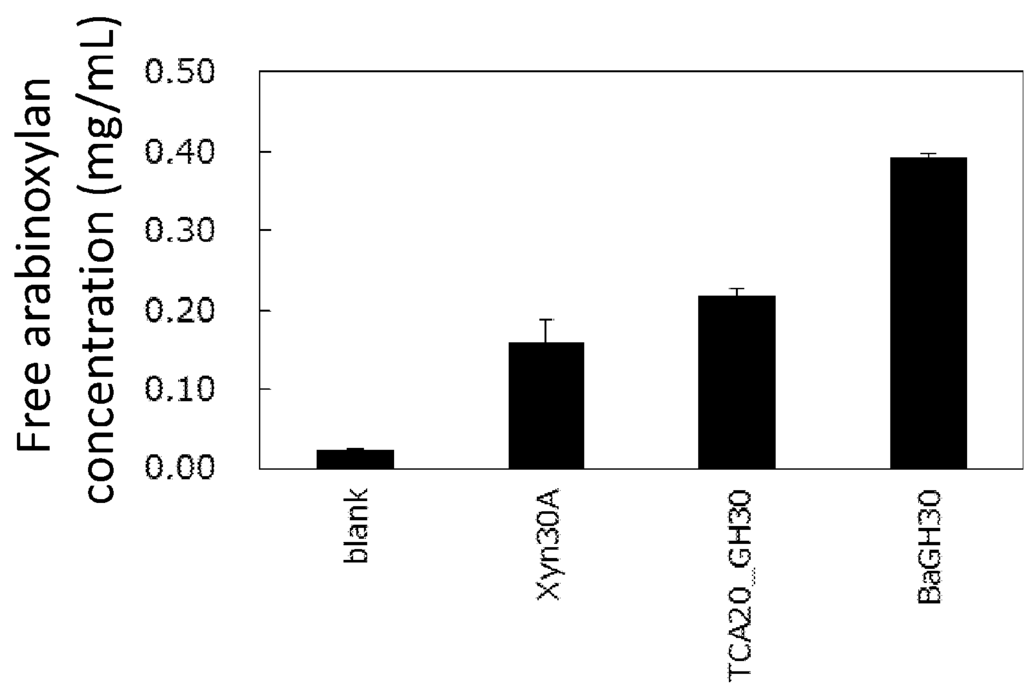
FIG. 5 shows a diagram showing release of soluble arabinoxylan from corn DDGS by various enzymes (enzyme concentration=1 μg/mL).

The results are shown in FIG. 5 (N=2, error bars each represent standard deviation). All of these enzymes released a larger amount of arabinoxylan than that observed for the case of the reaction without addition of enzyme (blank), and hence, it was revealed that they have an activity of releasing arabinoxylan from DDGS.

Example 16: Preparation of Abf51A in *E. coli*

(1) Acquisition of Sequence of Abf51A

As a result of analyzing the genomic sequence of the H2C strain, a gene of an enzyme having high homology with GH family 51 enzymes, and this enzyme was designated as Abf51A. The amino acid sequence of Abf51A precursor (pro sequence) is presumed to be SEQ ID NO: 36. As for this amino acid sequence, the secretory signal peptide sequence was predicted using GENETYX Ver. 10 (Genetyx). It was presumed that the amino acid sequence of the mature protein of Abf51A corresponds to positions 1 to 469 of SEQ ID NO: 36 and is encoded by the nucleotide sequence of positions 82 to 1488 of SEQ ID NO: 37. The positions −27 to −1 of SEQ ID NO: 36 are presumed to be a signal peptide.

Construction of Expression Strain for Abf51A

By using the genomic DNA of the H2C strain as a template and primers P11 and P12 (SEQ ID NOs: 38 and 39), a region containing a nucleotide sequence encoding Abf51A was PCR-amplified. PCR-amplification was carried out using PrimeStar Max (Takara Bio). The reaction solution was prepared according to the composition attached to the kit, and 30 cycles of reaction at 98° C. for 10 seconds, 55° C. for 10 seconds, and 68° C. for 10 seconds were carried out. The obtained PCR fragment was ligated with pET-21b (+) vector (Merck Millipore) digested with NdeI and XhoI using In-Fusion HD Cloning Kit (Clontech). *E. coli* JM109 was transformed with this ligation reaction solution, and an objective plasmid was extracted from an ampicillin resistant strain. *E. coli* BL21(DE3) was transformed with this plasmid, to obtain an expression strain of Abf51A. In this expression strain, a protein with His-tag added to the C-terminus of the mature protein is expressed. Incidentally, it is presumed that the signal peptide of Abf51A is cleaved after expression and a mature protein is generated.

Purification of Recombinant Enzyme

The expression strain of Abf51A was cultured overnight at 37° C. using LB medium, and the culture broth was inoculated into fresh LB medium in an amount of 1% (v/v). Once the strain was cultured at 37° C. to reach an exponential growth phase (0D660 was about 0.40 to 0.60), isopropyl-β-D-thiogalactopyranoside (IPTG, Nacalai Tesque) at a final concentration of 0.5 mM was added. The culture was further continued at 18° C. for 18 hours, to induce expression of the objective gene. Cells harvested by centrifugation (4° C., 6,900×g, 10 minutes) were suspended in 50 mM Britton-Robinson buffer (pH 6.5). The cells were disrupted using an ultrasonicator Bioruptor UCD-250 (Cosmo Bio), then centrifuged again (4° C., 20,400×g, 10 minutes), and the obtained supernatant was taken as a cell-free extract.

The cell-free extract was purified by a batch method using Ni Sepharose 6 Fast Flow (GE Healthcare), which is a nickel-immobilized carrier for purifying His-tag proteins. The binding buffer used was 50 mM Tris-HCl buffer (pH 7.5) containing 25 mM imidazole, and the elution buffer used was 50 mM Tris-HCl buffer (pH 7.5) containing 500 mM imidazole. First, 133 μL of 75%-slurried carrier was taken in a 1.5 mL microtube, washed with sterilized ion exchange water and the binding buffer in volumes of 2.5 times the volume of the carrier, and then equilibrated with an equal volume of the binding buffer. Next, the sample was added to the carrier, and gently stirred at 4° C. for 30 minutes using a rotator (Aikuru, Iwaki). The carrier was washed three times with 5 volume of the binding buffer, and then eluted three times with 2 volume of the elution buffer. The elution fraction dialyzed against 10 mM Britton-Robinson buffer (pH 6.5) was taken as a purified enzyme solution.

The concentration of the obtained purified enzyme was quantified. The Lowry method (DC Protein Assay, Bio-Rad) was used for protein quantification. The protein concentration was calculated on the basis of a calibration curve prepared using bovine serum albumin (BSA, Sigma) as a standard substance.

Example 17: Evaluation of Wheat Arabinoxylan Degradation Activity of Abf51A and Xyn5A Insoluble arabinoxylan derived from wheat (WAX, Megazyme, P-WAXYI) was suspended in 50 mM Britton-Robinson buffer (pH 6.5) to a final concentration of 1.2%, to obtain a substrate solution. A 80 μL-aliquot of this substrate solution was mixed with 10 μL of 2.15 pmol/mL Abf51A purified enzyme solution, 10 μL of 2.68 pmol/μL Xyn5A purified enzyme solution (Example 4), or both, filled up to 100 μL, and a reaction was carried out at pH 6.5 and 37° C. After the enzymatic reaction, the reaction was terminated by addition of 100 μL of 1 M NaOH. An insoluble substrate was precipitated by centrifugation (4° C., 20,400×g, 10 minutes), and a supernatant was recovered. The amount of reduced termini generated by hydrolysis of the substrate in this supernatant was quantified by the dinitrosalicylic acid method.

Figure 6:
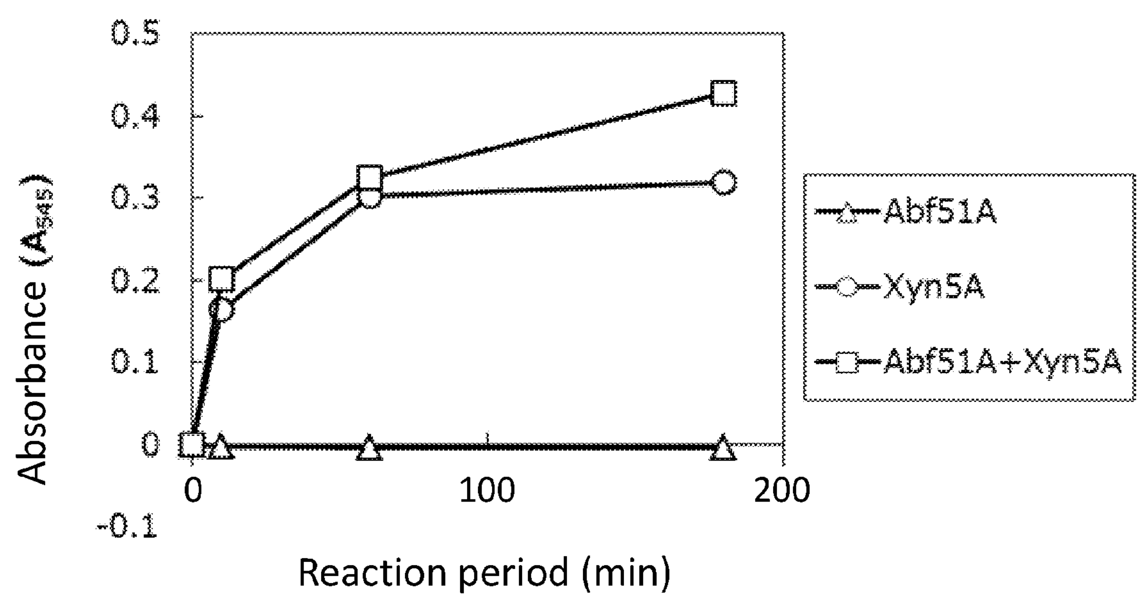
FIG. 6 shows a diagram showing degradation of wheat arabinoxylan by various enzymes.

The results are shown in FIG. 6 (N=2). Addition of both of Abf51A and Xyn5A provided a higher absorbance than that observed when each enzyme was added solely, and hence, showed a synergistic effect on degradation of wheat arabinoxylan.

Example 18: Evaluation of Corn NSP Degradation Activity of Abf51A and Xyn5A

Corn NSP (Nisshoku CELLFER) was suspended in 50 mM Britton-Robinson buffer (pH 6.5) to a final concentration of 3.125%, to obtain a substrate solution. A 400 μL-aliquot of this substrate solution was mixed with 50 μL of 2.15 pmol/mL Abf51A purified enzyme solution, 50 μL of 2.68 pmol/μL Xyn5A purified enzyme solution (Example 4), or both, filled up to 500 μL, and a reaction was carried out at pH 6.5 and 37° C. After the enzymatic reaction, the reaction was terminated by boiling for 2 minutes. An insoluble substrate was precipitated by centrifugation (4° C., 20,400× g, 20 minutes), and a supernatant was recovered. The amount of arabinoxylan in this supernatant was quantified by the phloroglucinol-acetate method.

Figure 7:
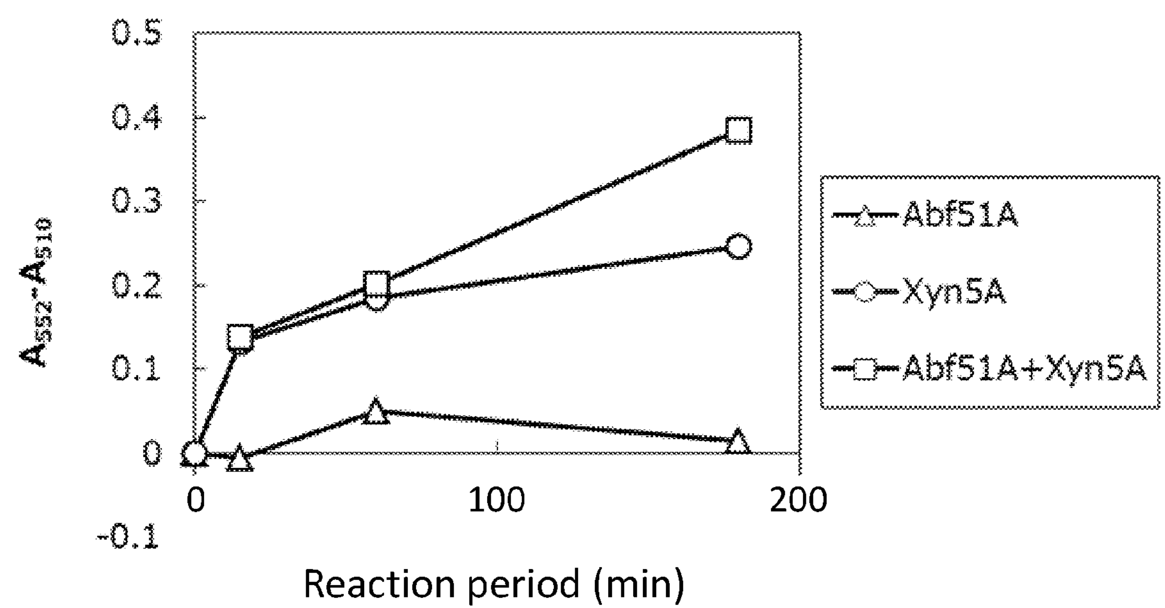
FIG. 7 shows a diagram showing release of soluble arabinoxylan from corn NSP by various enzymes.

The results are shown in FIG. 7 (N=2). Addition of both of Abf51A and Xyn5A provided a larger value of the difference between absorbance at 552 nm and absorbance at 510 nm than that observed when each enzyme was added solely, and hence, showed a synergistic effect on degradation of corn NSP.

INDUSTRIAL APPLICABILITY

According to the present invention, hemicellulase that degrades corn NSP is provided. This hemicellulase is useful for, for example, saccharide production from biomass resources.

<Explanation of Sequence Listing>

SEQ ID NOS:

1: Partial amino acid sequence of Xyn5A protein of *Paenibacillus* sp. H2C

2: Partial amino acid sequence of Xyn10B protein of *Paenibacillus* sp. H2C

3: Nucleotide sequence of Xyn5A gene of *Paenibacillus* sp. H2C

4: Amino acid sequence of Xyn5A protein of *Paenibacillus* sp. H2C

5: Nucleotide sequence of Xyn10B gene of *Paenibacillus* sp. H2C

6: Amino acid sequence of Xyn10B protein of *Paenibacillus* sp. H2C

7: Partial amino acid sequence of Xyn11A protein of *Paenibacillus* sp. H2C

8: Nucleotide sequence of Xyn11A gene of *Paenibacillus* sp. H2C

9: Amino acid sequence of Xyn11A protein of *Paenibacillus* sp. H2C

10: Partial amino acid sequence of Xyn30A protein of *Paenibacillus* sp. H2C

11: Nucleotide sequence of Xyn30A gene of *Paenibacillus* sp. H2C

12: Amino acid sequence of Xyn30A protein of *Paenibacillus* sp. H2C

13: Nucleotide sequence of Xyn43A gene of *Paenibacillus* sp. H2C

14: Amino acid sequence of Xyn43A protein of *Paenibacillus* sp. H2C 15 to 24: Primers 25: Partial amino acid sequence of Xyn43A protein of *Paenibacillus* sp. H2C 26: Amino acid sequence of P1XP2_GH5 protein of *Paenibacillus* sp. P1XP2

27: Nucleotide sequence of P1XP2_GH5 gene of *Paenibacillus* sp. P1XP2

28: Amino acid sequence of JDR-2_GH5 protein of *Paenibacillus* sp. JDR-2

29: Nucleotide sequence of JDR-2_GH5 gene of *Paenibacillus* sp. JDR-2

30: Amino acid sequence of BcGH5 protein of *Bacillus* caseinilyticus

31: Nucleotide sequence of BcGH5 gene of *Bacillus* caseinilyticus

32: Amino acid sequence of TCA20_GH30 protein of *Paenibacillus* sp. TCA20

33: Nucleotide sequence of TCA20_GH30 gene of *Paenibacillus* sp. TCA20

34: Amino acid sequence of BaGH30 protein of *Bacillus amyloliquefaciens*

35: Nucleotide sequence of BaGH30 gene of *Bacillus amyloliquefaciens*

36: Amino acid sequence of Abf51A protein of *Paenibacillus* sp. H2C

37: Nucleotide sequence of Abf51A gene of *Paenibacillus* sp. H2C 38 to 39: Primers

The invention claimed is:

1. A composition comprising a first protein and a second protein, said first and second proteins are each selected from the group consisting of protein (A), protein (B), protein (C), and protein (D) provided that the composition comprises at least the protein (A) or (B);

wherein the protein (A) is selected from the group consisting of:

(A1) a protein comprising the amino acid sequence of positions 1 to 536 of SEQ ID NO: 26, positions 1 to 536 of SEQ ID NO: 28, or positions 1 to 536 of SEQ ID NO: 30, wherein said protein has hemicellulase activity;

(A2) a protein comprising the amino acid sequence of positions 1 to 536 of SEQ ID NO: 26, positions 1 to 536 of SEQ ID NO: 28, or positions 1 to 536 of SEQ ID NO: 30, but which includes substitution, deletion, insertion, and/or addition of 1 to 10 amino acid residues, wherein said protein has hemicellulase activity; and (A3) a protein comprising an amino acid sequence showing an identity of 90% or higher to the amino acid sequence of positions 1 to 536 of SEQ ID NO: 26, positions 1 to 536 of SEQ ID NO: 28, or positions 1 to 536 of SEQ ID NO: 30, wherein said protein has hemicellulase activity;

wherein the protein (B) is selected from the group consisting of:

(B1) a protein comprising the amino acid sequence of positions 1 to 527 of SEQ ID NO: 12, or positions 1 to 390 of SEQ ID NO: 34, wherein said protein has hemicellulase activity, (B2) a protein comprising the amino acid sequence of positions 1 to 527 of SEQ ID NO: 12, or positions 1 to 390 of SEQ ID NO: 34, but which includes substitution, deletion, insertion, and/or addition of 1 to 10 amino acid residues, wherein said protein has hemicellulase activity, and (B3) a protein comprising an amino acid sequence showing an identity of 90% or higher to the amino acid sequence of positions 1 to 527 of SEQ ID NO: 12, or positions 1 to 390 of SEQ ID NO: 34, wherein said protein has hemicellulase activity;

wherein the protein (C) is a hemicellulase of glucoside hydrolase family 10; and where in the protein (D) is a hemicellulose of glucoside hydrolase family 11.

2. The composition according to claim 1, wherein said proteins (A), (B), (C), and (D) each have beta-1,4-xylanase activity.

3. A hemicellulase preparation comprising a protein selected from the group consisting of proteins (A), (B), and combinations thereof;

wherein the protein (A) is selected from the group consisting of:

(A1) a protein comprising the amino acid sequence of positions 1 to 536 of SEQ ID NO: 26, positions 1 to 536 of SEQ ID NO: 28, or positions 1 to 536 of SEQ ID NO: 30, wherein said protein has hemicellulase activity, (A2) a protein comprising the amino acid sequence of positions 1to to 536 of SEQ ID NO: 26, positions 1 to 536 of SEQ ID NO: 28, or positions 1 to 536 of SEQ ID NO: 30, but which includes substitution, deletion, insertion, and/or addition of 1 to 10 amino acid residues, wherein said protein has hemicellulase activity, and (A3) a protein comprising an amino acid sequence showing an identity of 90% or higher to the amino acid sequence of positions 1 to 536 of SEQ ID NO: 26, positions 1 to 536 of SEQ ID NO: 28, or positions 1 to 536 of SEQ ID NO: 30, wherein said protein has hemicellulase activity;

wherein the protein (B) is selected from the group consisting of:

(B1) a protein comprising the amino acid sequence of positions 1 to 527 of SEQ ID NO: 12, or positions 1 to 390 of SEQ ID NO: 34, wherein said protein has hemicellulase activity, (B2) a protein comprising the amino acid sequence of positions 1 to 527 of SEQ ID NO: 12, or positions 1 to 390 of SEQ ID NO: 34, but which includes substitution, deletion, insertion, and/or addition of 1 to 10 amino acid residues, wherein said protein has hemicellulase activity, and (B3) a protein comprising an amino acid sequence showing an identity of 90% or higher to the amino acid sequence of positions 1 to 527 of SEQ ID NO: 12, or positions 1 to 390 of SEQ ID NO: 34, wherein said protein has hemicellulase activity.

4. The hemicellulase preparation according to claim 3, wherein the protein comprises a first protein selected from the group consisting of proteinn (A) and (B), and a second protein selected from the group consisting of the proteins (C) and (D), wherein the protein (C) is a hemicellulose of glucoside hydrolase family 10; and wherein the protein (D) is a hemicellulose of glucoside hydrolase family 11.

5. The hemicellulase preparation according to claim 3, further comprising a protein selected from the group consisting of:

(F1) a protein comprising the amino acid sequence of positions 1 to 469 of SEQ ID NO: 36, wherein said protein has a property of enhancing hemicellulase activity;

(F2) a protein comprising the amino acid sequence of positions 1 to 469 of SEQ ID NO: 36, but which includes substitution, deletion, insertion, and/or addition of 1 to 10 amino acid residues, wherein said protein has a property of enhancing hemicellulase activity; and (F3) a protein comprising an amino acid sequence showing an identity of 90% or higher to the amino acid sequence of positions 1 to 469 of SEQ ID NO: 36, wherein said protein has a property of enhancing hemicellulase activity.

6. A method for producing a saccharification product, the method comprising:

treating a hemicellulosic substrate with the protein according to claim 1.

7. The method according to claim 6, wherein the hemicellulosic substrate is a biomass resource.

8. An animal feed additive comprising a protein selected from the group consisting of proteins (A), (B), and combinations thereof;

wherein the protein (A) is selected from the group consisting of:

(A1) a protein comprising the amino acid sequence of positions 1 to 536 of SEQ ID NO: 26, positions 1 to 536 of SEQ ID NO: 28, or positions 1 to 536 of SEQ ID NO: 30, wherein said protein has hemicellulase activity, (A2) a protein comprising the amino acid sequence of positions 1 to 536 of SEQ ID NO: 26, positions 1 to 536 of SEQ ID NO: 28, or positions 1 to 536 of SEQ ID NO: 30, but which includes substitution, deletion, insertion, and/or addition of 1 to 10 amino acid residues, wherein said protein has hemicellulase activity; and (A3) a protein comprising an amino acid sequence showing an identity of 90% or higher to the amino acid sequence of positions 1 to 536 of SEQ ID NO: 26, positions 1 to 536 of SEQ ID NO: 28, or positions 1 to 536 of SEQ ID NO: 30, wherein said protein has hemicellulase activity;

wherein the protein (B) is selected from the group consisting of:

(B1) a protein comprising the amino acid sequence of positions 1 to 527 of SEQ ID NO: 12, or positions 1 to 390 of SEQ ID NO: 34, wherein said protein has hemicellulase activity;

(B2) a protein comprising the amino acid sequence of positions 1 to 527 of SEQ ID NO: 12, or positions 1 to 390 of SEQ ID NO: 34, but which includes substitution, deletion, insertion, and/or addition of 1 to 10 amino acid residues, wherein said protein has hemicellulase activity; and (B3) a protein comprising an amino acid sequence showing an identity of 90% or higher to the amino acid sequence of positions 1 to 527 of SEQ ID NO: 12, or positions 1 to 390 of SEQ ID NO: 34, wherein said protein has hemicellulase activity.

9. The animal feed additive according to claim 8, further comprising a protein selected from the group consisting of:

(F1) a protein comprising the amino acid sequence of positions 1 to 469 of SEQ ID NO: 36, wherein said protein has a property of enhancing hemicellulase activity;

(F2) a protein comprising the amino acid sequence of positions 1 to 469 of SEQ ID NO: 36, but which includes substitution, deletion, insertion, and/or addition of 1 to 10 amino acid residues, wherein said protein has a property of enhancing hemicellulase activity; and (F3) a protein comprising an amino acid sequence showing an identity of 90% or higher to the amino acid sequence of positions 1 to 469 of SEQ ID NO: 36, wherein said protein has a property of enhancing hemicellulase activity.

10. An animal feed comprising at least one protein selected from the group consisting of proteins (A), (B), and combinations thereof, wherein the protein (A) is selected from the group consisting of:

(A1) a protein comprising the amino acid sequence of positions 1 to 536 of SEQ ID NO: 26, positions 1 to 536 of SEQ ID NO: 28, or positions 1 to 536 of SEQ ID NO: 30, wherein said protein has hemicellulase activity;

(A2) a protein comprising the amino acid sequence of positions 1 to 536 of SEQ ID NO: 26, positions 1 to 536 of SEQ ID NO: 28, or positions 1 to 536 of SEQ ID NO: 30, but which includes substitution, deletion, insertion, and/or addition of 1 to 10 amino acid residues, wherein said protein has hemicellulase activity; and (A3) a protein comprising an amino acid sequence showing an identity of 90% or higher to the amino acid sequence of positions 1 to 536 of SEQ ID NO: 26, positions 1 to 536 of SEQ ID NO: 28, or positions 1 to 536 of SEQ ID NO: 30, wherein said protein has hemicellulase activity;

wherein the protein (B) is selected from the group consisting of:

(B1) a protein comprising the amino acid sequence of positions 1 to 527 of SEQ ID NO: 12, or positions 1 to 390 of SEQ ID NO: 34, wherein said protein has hemicellulase activity;

(B2) a protein comprising the amino acid sequence of positions 1 to 527 of SEQ ID NO: 12, or positions 1 to 390 of SEQ ID NO: 34, but which includes substitution, deletion, insertion, and/or addition of 1 to 10 amino acid residues, wherein said protein has hemicellulase activity; and (B3) a protein comprising an amino acid sequence showing an identity of 90% or higher to the amino acid sequence of positions 1 to 527 of SEQ ID NO: 12, or positions 1 to 390 of SEQ ID NO: 34, wherein said protein has hemicellulase activity.

11. The animal feed according to claim 10, further comprising a protein selected from the group consisting of:

(F1) a protein comprising the amino acid sequence of positions 1 to 469 of SEQ ID NO: 36, wherein said protein has a property of enhancing hemicellulase activity;

(F2) a protein comprising the amino acid sequence of positions 1 to 469 of SEQ ID NO: 36, but which includes substitution, deletion, insertion, and/or addition of 1 to 10 amino acid residues, wherein said protein has a property of enhancing hemicellulase activity;

(F3) a protein comprising an amino acid sequence showing an identity of 90% or higher to the amino acid sequence of positions 1 to 469 of SEQ ID NO: 36, wherein said protein has a property of enhancing hemicellulase activity.

12. The composition according to claim 1, wherein the first protein is selected from the group consisting of the proteins (A) and (B), and wherein the second protein is selected from the group consisting of the proteins (C) and (D).

13. The composition according to claim 1, wherein the first protein is selected from the group consisting of the proteins (A) and (B), and wherein the second protein is the protein (C).

14. The composition according to claim 1, wherein the protein (C) is selected from the group consisting of:

(C1) a protein comprising the amino acid sequence of positions 1 to 448 of SEQ ID NO: 6, wherein said protein has hemicellulase activity;

(C2) a protein comprising the amino acid sequence of positions 1 to 448 of SEQ ID NO: 6, but which includes substitution, deletion, insertion, and/or addition of 1 to 10 amino acid residues, wherein said protein has hemicellulase activity; and (C3) a protein comprising an amino acid sequence showing an identity of 90% or higher to the amino acid sequence of positions 1 to 448 of SEQ ID NO: 6, wherein said protein has hemicellulase activity;

wherein the protein (D) is selected from the group consisting of:

(D1) a protein comprising the amino acid sequence of positions 1 to 183 of SEQ ID NO: 9, wherein said protein has hemicellulase activity;

(D2) a protein comprising the amino acid sequence of positions 1 to 183 of SEQ ID NO: 9, but which includes substitution, deletion, insertion, and/or addition of 1 to 10 amino acid residues, wherein said protein has hemicellulase activity; and (D3) a protein comprising an amino acid sequence showing an identity of 90% or higher to the amino acid sequence of positions 1 to 183 of SEQ ID NO: 9, wherein said protein has hemicellulase activity.

15. The composition according to claim 1, comprising the protein (B), wherein the protein (B) is selected from the group consisting of:

(B1a) a protein comprising the amino acid sequence of positions 1 to 527 of SEQ ID NO: 12, wherein said protein has hemicellulase activity;

(B2a) a protein comprising the amino acid sequence of positions 1 to 527 of SEQ ID NO: 12, but which includes substitution, deletion, insertion, and/or addition of 1 to 10 amino acid residues, wherein said protein has hemicellulase activity; and (B3a) a protein comprising an amino acid sequence showing an identity of 90% or higher to the amino acid sequence of positions 1 to 527 of SEQ ID NO: 12, wherein said protein has hemicellulase activity.

16. The hemicellulase preparation according to claim 4, wherein the first protein is selected from the group consisting of the proteins (A) and (B), and wherein the second protein is selected from the group consisting of the proteins (C) and (D).

17. The hemicellulase preparation according to claim 4, wherein the first protein is selected from the group consisting of the proteins (A) and (B), and wherein the second protein is the protein (C).

18. The hemicellulase preparation according to claim 3, wherein the protein (C) is selected from the group consisting of:

(C1) a protein comprising the amino acid sequence of positions 1 to 448 of SEQ ID NO: 6, wherein said protein has hemicellulase activity;

(C2) a protein comprising the amino acid sequence of positions 1 to 448 of SEQ ID NO: 6, but which includes substitution, deletion, insertion, and/or addition of 1 to 10 amino acid residues, wherein said protein has hemicellulase activity; and (C3) a protein comprising an amino acid sequence showing an identity of 90% or higher to the amino acid sequence of positions 1 to 448 of SEQ ID NO: 6, wherein said protein has hemicellulase activity;

wherein the protein (D) is selected from the group consisting of:

(D1) a protein comprising the amino acid sequence of positions 1 to 183 of SEQ ID NO: 9, wherein said protein has hemicellulase activity;

(D2) a protein comprising the amino acid sequence of positions 1 to 183 of SEQ ID NO: 9, but which includes substitution, deletion, insertion, and/or addition of 1 to 10 amino acid residues, wherein said protein has hemicellulase activity; and (D3) a protein comprising an amino acid sequence showing an identity of 90% or higher to the amino acid sequence of positions 1 to 183 of SEQ ID NO: 9, wherein said protein has hemicellulase activity.

19. The hemicellulase preparation according to claim 3, comprising the protein (B), wherein the protein (B) is selected from the group consisting of:

(B1a) a protein comprising the amino acid sequence of positions 1 to 527 of SEQ ID NO: 12, wherein said protein has hemicellulase activity;

(B2a) a protein comprising the amino acid sequence of positions 1 to 527 of SEQ ID NO: 12, but which includes substitution, deletion, insertion, and/or addition of 1 to 10 amino acid residues, wherein said protein has hemicellulase activity; and (B3a) a protein comprising an amino acid sequence showing an identity of 90% or higher to the amino acid sequence of positions 1 to 527 of SEQ ID NO: 12, wherein said protein has hemicellulase activity.

20. The animal feed additive according to claim 8, wherein the protein comprises a first protein and a second protein, wherein the first protein is selected from the group consisting of (A) and (B); and the second protein is selected from the group consisting of the proteins (C) and (D);

wherein the protein (C) is a hemicellulase of glucoside hydrolase family 10; and wherein the protein (D) is a hemicellulase of glucoside hydrolase family 11.

21. The animal feed additive according to claim 20, wherein the first protein is selected from the group consisting of the proteins (A) and (B), and wherein the second protein is selected from the group consisting of the proteins (C) and (D).

22. The animal feed additive according to claim 20, wherein the first protein is selected from the group consisting of the proteins (A) and (B), and wherein the second protein is the protein (C).

23. The animal feed additive according to claim 8, wherein the protein (C) is selected from the group consisting of:

(C1) a protein comprising the amino acid sequence of positions 1 to 448 of SEQ ID NO: 6, wherein said protein has hemicellulase activity;

(C2) a protein comprising the amino acid sequence of positions 1 to 448 of SEQ ID NO: 6, but which includes substitution, deletion, insertion, and/or addition of 1 to 10 amino acid residues, wherein said protein has hemicellulase activity; and (C3) a protein comprising an amino acid sequence showing an identity of 90% or higher to the amino acid sequence of positions 1 to 448 of SEQ ID NO: 6, wherein said protein has hemicellulase activity;

wherein the protein (D) is selected from the group consisting of:

(D1) a protein comprising the amino acid sequence of positions 1 to 183 of SEQ ID NO: 9, wherein said protein has hemicellulase activity;

(D2) a protein comprising the amino acid sequence of positions 1 to 183 of SEQ ID NO: 9, but which includes substitution, deletion, insertion, and/or addition of 1 to 10 amino acid residues, wherein said protein has hemicellulase activity; and (D3) a protein comprising an amino acid sequence showing an identity of 90% or higher to the amino acid sequence of positions 1 to 183 of SEQ ID NO: 9, wherein said protein has hemicellulase activity.

24. The animal feed additive according to claim 8, comprising the protein (B), wherein the protein (B) is selected from the group consisting of:

(B1a) a protein comprising the amino acid sequence of positions 1 to 527 of SEQ ID NO: 12, wherein said protein has hemicellulase activity;

(B2a) a protein comprising the amino acid sequence of positions 1 to 527 of SEQ ID NO: 12, but which includes substitution, deletion, insertion, and/or addition of 1 to 10 amino acid residues, wherein said protein has hemicellulase activity; and (B3a) a protein comprising an amino acid sequence showing an identity of 90% or higher to the amino acid sequence of positions 1 to 527 of SEQ ID NO: 12, wherein said protein has hemicellulase activity.

25. The animal feed according to claim 10, wherein the protein comprises a first protein and a second protein, wherein the first protein is selected from the group consisting of (A) and (B); and the second protein is selected from the group consisting of the proteins (C) and (D);

wherein the protein (C) is a hemicellulase of glucoside hydrolase family 10; and wherein the protein (D) is a hemicellulase of glucoside hydrolase family 11.

26. The animal feed according to claim 25, wherein the first protein is selected from the group consisting of the proteins (A) and (B), and wherein the second protein is selected from the group consisting of the proteins (C) and (D).

27. The animal feed according to claim 25, wherein the first protein is selected from the group consisting of the proteins (A) and (B), and wherein the second protein is the protein (C).

28. The animal feed according to claim 10, wherein the protein (C) is selected from the group consisting of:

(C1) a protein comprising the amino acid sequence of positions 1 to 448 of SEQ ID NO: 6, wherein said protein has hemicellulase activity;

(C2) a protein comprising the amino acid sequence of positions 1 to 448 of SEQ ID NO: 6, but which includes substitution, deletion, insertion, and/or addition of 1 to 10 amino acid residues, wherein said protein has hemicellulase activity; and (C3) a protein comprising an amino acid sequence showing an identity of 90% or higher to the amino acid sequence of positions 1 to 448 of SEQ ID NO: 6, wherein said protein has hemicellulase activity;

wherein the protein (D) is selected from the group consisting of:

(D1) a protein comprising the amino acid sequence of positions 1 to 183 of SEQ ID NO: 9, wherein said protein has hemicellulase activity;

(D2) a protein comprising the amino acid sequence of positions 1 to 183 of SEQ ID NO: 9, but which includes substitution, deletion, insertion, and/or addition of 1 to 10 amino acid residues, wherein said protein has hemicellulase activity; and (D3) a protein comprising an amino acid sequence showing an identity of 90% or higher to the amino acid sequence of positions 1 to 183 of SEQ ID NO: 9, wherein said protein has hemicellulase activity.

29. The animal feed according to claim 10, comprising the protein (B), wherein the protein (B) is selected from the group consisting of:

(B1a) a protein comprising the amino acid sequence of positions 1 to 527 of SEQ ID NO: 12, wherein said protein has hemicellulase activity;

(B2a) a protein comprising the amino acid sequence of positions 1 to 527 of SEQ ID NO: 12, but which includes substitution, deletion, insertion, and/or addition of 1 to 10 amino acid residues, wherein said protein has hemicellulase activity; and (B3a) a protein comprising an amino acid sequence showing an identity of 90% or higher to the amino acid sequence of positions 1 to 527 of SEQ ID NO: 12, wherein said protein has hemicellulase activity.

* * * * *

SEQUENCE LISTING

```
<160> NUMBER OF SEQ ID NOS: 39

<210> SEQ ID NO 1
<211> LENGTH: 8
<212> TYPE: PRT
<213> ORGANISM: Paenibacillus sp.

<400> SEQUENCE: 1

Ser Gly Met Gln Met Ser Lys Leu
1               5


<210> SEQ ID NO 2
<211> LENGTH: 15
<212> TYPE: PRT
<213> ORGANISM: Paenibacillus sp.
<220> FEATURE:
<221> NAME/KEY: misc_feature
<222> LOCATION: (12)..(12)
<223> OTHER INFORMATION: Xaa can be any naturally occurring amino acid

<400> SEQUENCE: 2

Ser Leu Val Ser Gly Ser Lys Phe Leu Gly Asn Xaa Ile Ala Gly
1               5                   10                  15


<210> SEQ ID NO 3
<211> LENGTH: 1722
<212> TYPE: DNA
<213> ORGANISM: Paenibacillus sp.
<220> FEATURE:
<221> NAME/KEY: CDS
<222> LOCATION: (1)..(1722)
<220> FEATURE:
<221> NAME/KEY: mat_peptide
<222> LOCATION: (115)..(1719)

<400> SEQUENCE: 3

atg aac aag gga gat gag gaa tta atg aaa gca agt tgg aca atc aag       48
Met Asn Lys Gly Asp Glu Glu Leu Met Lys Ala Ser Trp Thr Ile Lys
            -35                 -30                 -25

ctt tta ctg ctc atg gcg tta att atg acg ccg att ctg gtc aat ggg       96
Leu Leu Leu Leu Met Ala Leu Ile Met Thr Pro Ile Leu Val Asn Gly
        -20                 -15                 -10

cag tcg gcg aat gca tgg tca ggc atg cag atg tcg aag ctt cat gtc      144
Gln Ser Ala Asn Ala Trp Ser Gly Met Gln Met Ser Lys Leu His Val
    -5              -1  1               5                   10

agc ggc aaa cag ctc gtg aac agc agc ggt cag ccc gta ctg ctg agc      192
Ser Gly Lys Gln Leu Val Asn Ser Ser Gly Gln Pro Val Leu Leu Ser
                15                  20                  25

ggc tgg cat cag ccg tca ggt gct tac tgg act tat cag aac agc aac      240
Gly Trp His Gln Pro Ser Gly Ala Tyr Trp Thr Tyr Gln Asn Ser Asn
            30                  35                  40

tac tac tta agt cag aac ggc aac aat cgg cat gca gct atc cta gcc      288
Tyr Tyr Leu Ser Gln Asn Gly Asn Asn Arg His Ala Ala Ile Leu Ala
        45                  50                  55

tat ttg aaa gac atc act gat acc ttc acg gac acc tca gcg aaa tat      336
Tyr Leu Lys Asp Ile Thr Asp Thr Phe Thr Asp Thr Ser Ala Lys Tyr
```

```
    60                  65                  70

ggc aat acg cat ggc tgg tat atg aac caa gta cgt cta ttc atc gac      384
Gly Asn Thr His Gly Trp Tyr Met Asn Gln Val Arg Leu Phe Ile Asp
75                  80                  85                  90

cgt gat gat atg ggc gat gta gca gca gga act tat aat ttc gcc ggc      432
Arg Asp Asp Met Gly Asp Val Ala Ala Gly Thr Tyr Asn Phe Ala Gly
                95                  100                 105

ttg cag agc gta acg caa aac gtc att ata ccg tac atc aac tac gct      480
Leu Gln Ser Val Thr Gln Asn Val Ile Ile Pro Tyr Ile Asn Tyr Ala
            110                 115                 120

aaa aca aaa ggc ctg tac gta acg ctg ggt ctt gat ttc acc ctt ctg      528
Lys Thr Lys Gly Leu Tyr Val Thr Leu Gly Leu Asp Phe Thr Leu Leu
        125                 130                 135

gac aac aag gcg acg acg cct tcg aac cta gct aaa ttc aat caa ata      576
Asp Asn Lys Ala Thr Thr Pro Ser Asn Leu Ala Lys Phe Asn Gln Ile
    140                 145                 150

tgg ggc tat ctc gca tcg cag cca gca atc aaa agc gcg gac aac gtg      624
Trp Gly Tyr Leu Ala Ser Gln Pro Ala Ile Lys Ser Ala Asp Asn Val
155                 160                 165                 170

atg ttc gag ctc gtt aac gag ccg gtg ctc tcc gat gtg aac ggc gta      672
Met Phe Glu Leu Val Asn Glu Pro Val Leu Ser Asp Val Asn Gly Val
                175                 180                 185

tgg ggc ggc aat ccg tcg caa tcc aat ttc gtc gac tac tgg aac tcg      720
Trp Gly Gly Asn Pro Ser Gln Ser Asn Phe Val Asp Tyr Trp Asn Ser
            190                 195                 200

ctg aag aac ttc cag aac tcg atg atc tcg acg ata cga aac caa ggc      768
Leu Lys Asn Phe Gln Asn Ser Met Ile Ser Thr Ile Arg Asn Gln Gly
        205                 210                 215

gca gat aat gtc atc tgg gca gcc gga ctt ggc tgg gat caa tat tac      816
Ala Asp Asn Val Ile Trp Ala Ala Gly Leu Gly Trp Asp Gln Tyr Tyr
    220                 225                 230

cag ctg tgc gca tcg aat ccg ctg acg gat ccg ctg aac aat ctc ggg      864
Gln Leu Cys Ala Ser Asn Pro Leu Thr Asp Pro Leu Asn Asn Leu Gly
235                 240                 245                 250

tat tcc gtt cac tgg tac ccg ggc tac ggc gcc aat gac aat ttc gca      912
Tyr Ser Val His Trp Tyr Pro Gly Tyr Gly Ala Asn Asp Asn Phe Ala
                255                 260                 265

acg ctg cag aac atc tgg aat aca acg atc aag cct tgc gcc gac aac      960
Thr Leu Gln Asn Ile Trp Asn Thr Thr Ile Lys Pro Cys Ala Asp Asn
            270                 275                 280

tat ccg atc aac att acg gag acg act tgg ttc aag aag aag gca ggg     1008
Tyr Pro Ile Asn Ile Thr Glu Thr Thr Trp Phe Lys Lys Lys Ala Gly
        285                 290                 295

gac tcc gat tat tgg agc ctg ttc aac ggc tcg aat gag ggc ttc ggc     1056
Asp Ser Asp Tyr Trp Ser Leu Phe Asn Gly Ser Asn Glu Gly Phe Gly
    300                 305                 310

aag aac acg aaa gcg atc ttt act gca gca ggc aac gtc agc att gcg     1104
Lys Asn Thr Lys Ala Ile Phe Thr Ala Ala Gly Asn Val Ser Ile Ala
315                 320                 325                 330

gcg cat atg aac ggc ttc att ctc gac cct ggt acg cga agc tcg ttc     1152
Ala His Met Asn Gly Phe Ile Leu Asp Pro Gly Thr Arg Ser Ser Phe
                335                 340                 345

gcg gat ccg aca gca ggt ttg aag tac gat ggc gat gcg acg cgc gac     1200
Ala Asp Pro Thr Ala Gly Leu Lys Tyr Asp Gly Asp Ala Thr Arg Asp
            350                 355                 360

ggc atg gcg cgt ttc ctg ttc gag tgg tat tat gag cgc gct caa ttc     1248
Gly Met Ala Arg Phe Leu Phe Glu Trp Tyr Tyr Glu Arg Ala Gln Phe
        365                 370                 375

aat cct tgg aac ggc att tgg aac gga cta acg aac ggc ggg act tac     1296
```

```
Asn Pro Trp Asn Gly Ile Trp Asn Gly Leu Thr Asn Gly Gly Thr Tyr
    380                 385                 390

aaa ttc gtc aac cgc gct tcg ggc aag gtg atc gat gtt ccg ggc agc      1344
Lys Phe Val Asn Arg Ala Ser Gly Lys Val Ile Asp Val Pro Gly Ser
395                 400                 405                 410

cag aat acg aac gcg ctg cag ctg tcg cag tat acg gat aat ggc gga      1392
Gln Asn Thr Asn Ala Leu Gln Leu Ser Gln Tyr Thr Asp Asn Gly Gly
                415                 420                 425

acc aac caa aaa tgg gtg att aca gac caa ggc acg tac aat aac ttc      1440
Thr Asn Gln Lys Trp Val Ile Thr Asp Gln Gly Thr Tyr Asn Asn Phe
            430                 435                 440

tac aaa ttg acc agc gta agc tca tcc gac ggt aaa gta atg gac gtg      1488
Tyr Lys Leu Thr Ser Val Ser Ser Ser Asp Gly Lys Val Met Asp Val
        445                 450                 455

cgc aat gga acc tcc aat aac ggt gaa gcg att cag ttg atg cag agc      1536
Arg Asn Gly Thr Ser Asn Asn Gly Glu Ala Ile Gln Leu Met Gln Ser
    460                 465                 470

ttt agt aat acg gct caa caa ttc cga ttg atc aag ttg agc aat gga      1584
Phe Ser Asn Thr Ala Gln Gln Phe Arg Leu Ile Lys Leu Ser Asn Gly
475                 480                 485                 490

tat tac tgc atc ctc aat gtc aat agt aac agg gct gta gag gtt gcg      1632
Tyr Tyr Cys Ile Leu Asn Val Asn Ser Asn Arg Ala Val Glu Val Ala
                495                 500                 505

agc tcc tcc acc tcg aac ggc gcg ttg atc cag cag aac ttg tat cgc      1680
Ser Ser Ser Thr Ser Asn Gly Ala Leu Ile Gln Gln Asn Leu Tyr Arg
            510                 515                 520

ggc gat ctg aac caa caa tgg caa tta gtc aaa atc aat taa              1722
Gly Asp Leu Asn Gln Gln Trp Gln Leu Val Lys Ile Asn
        525                 530                 535


<210> SEQ ID NO 4
<211> LENGTH: 573
<212> TYPE: PRT
<213> ORGANISM: Paenibacillus sp.

<400> SEQUENCE: 4

Met Asn Lys Gly Asp Glu Glu Leu Met Lys Ala Ser Trp Thr Ile Lys
            -35                 -30                 -25

Leu Leu Leu Leu Met Ala Leu Ile Met Thr Pro Ile Leu Val Asn Gly
        -20                 -15                 -10

Gln Ser Ala Asn Ala Trp Ser Gly Met Gln Met Ser Lys Leu His Val
    -5              -1  1               5                   10

Ser Gly Lys Gln Leu Val Asn Ser Ser Gly Gln Pro Val Leu Leu Ser
                15                  20                  25

Gly Trp His Gln Pro Ser Gly Ala Tyr Trp Thr Tyr Gln Asn Ser Asn
            30                  35                  40

Tyr Tyr Leu Ser Gln Asn Gly Asn Asn Arg His Ala Ala Ile Leu Ala
        45                  50                  55

Tyr Leu Lys Asp Ile Thr Asp Thr Phe Thr Asp Thr Ser Ala Lys Tyr
    60                  65                  70

Gly Asn Thr His Gly Trp Tyr Met Asn Gln Val Arg Leu Phe Ile Asp
75                  80                  85                  90

Arg Asp Asp Met Gly Asp Val Ala Ala Gly Thr Tyr Asn Phe Ala Gly
                95                  100                 105

Leu Gln Ser Val Thr Gln Asn Val Ile Ile Pro Tyr Ile Asn Tyr Ala
            110                 115                 120

Lys Thr Lys Gly Leu Tyr Val Thr Leu Gly Leu Asp Phe Thr Leu Leu
        125                 130                 135
```

```
Asp Asn Lys Ala Thr Thr Pro Ser Asn Leu Ala Lys Phe Asn Gln Ile
    140                 145                 150

Trp Gly Tyr Leu Ala Ser Gln Pro Ala Ile Lys Ser Ala Asp Asn Val
155                 160                 165                 170

Met Phe Glu Leu Val Asn Glu Pro Val Leu Ser Asp Val Asn Gly Val
                175                 180                 185

Trp Gly Gly Asn Pro Ser Gln Ser Asn Phe Val Asp Tyr Trp Asn Ser
            190                 195                 200

Leu Lys Asn Phe Gln Asn Ser Met Ile Ser Thr Ile Arg Asn Gln Gly
        205                 210                 215

Ala Asp Asn Val Ile Trp Ala Ala Gly Leu Gly Trp Asp Gln Tyr Tyr
    220                 225                 230

Gln Leu Cys Ala Ser Asn Pro Leu Thr Asp Pro Leu Asn Asn Leu Gly
235                 240                 245                 250

Tyr Ser Val His Trp Tyr Pro Gly Tyr Gly Ala Asn Asp Asn Phe Ala
                255                 260                 265

Thr Leu Gln Asn Ile Trp Asn Thr Thr Ile Lys Pro Cys Ala Asp Asn
            270                 275                 280

Tyr Pro Ile Asn Ile Thr Glu Thr Thr Trp Phe Lys Lys Lys Ala Gly
        285                 290                 295

Asp Ser Asp Tyr Trp Ser Leu Phe Asn Gly Ser Asn Glu Gly Phe Gly
    300                 305                 310

Lys Asn Thr Lys Ala Ile Phe Thr Ala Ala Gly Asn Val Ser Ile Ala
315                 320                 325                 330

Ala His Met Asn Gly Phe Ile Leu Asp Pro Gly Thr Arg Ser Ser Phe
                335                 340                 345

Ala Asp Pro Thr Ala Gly Leu Lys Tyr Asp Gly Asp Ala Thr Arg Asp
            350                 355                 360

Gly Met Ala Arg Phe Leu Phe Glu Trp Tyr Tyr Glu Arg Ala Gln Phe
        365                 370                 375

Asn Pro Trp Asn Gly Ile Trp Asn Gly Leu Thr Asn Gly Gly Thr Tyr
    380                 385                 390

Lys Phe Val Asn Arg Ala Ser Gly Lys Val Ile Asp Val Pro Gly Ser
395                 400                 405                 410

Gln Asn Thr Asn Ala Leu Gln Leu Ser Gln Tyr Thr Asp Asn Gly Gly
                415                 420                 425

Thr Asn Gln Lys Trp Val Ile Thr Asp Gln Gly Thr Tyr Asn Asn Phe
            430                 435                 440

Tyr Lys Leu Thr Ser Val Ser Ser Ser Asp Gly Lys Val Met Asp Val
        445                 450                 455

Arg Asn Gly Thr Ser Asn Asn Gly Glu Ala Ile Gln Leu Met Gln Ser
    460                 465                 470

Phe Ser Asn Thr Ala Gln Gln Phe Arg Leu Ile Lys Leu Ser Asn Gly
475                 480                 485                 490

Tyr Tyr Cys Ile Leu Asn Val Asn Ser Asn Arg Ala Val Glu Val Ala
                495                 500                 505

Ser Ser Ser Thr Ser Asn Gly Ala Leu Ile Gln Gln Asn Leu Tyr Arg
            510                 515                 520

Gly Asp Leu Asn Gln Gln Trp Gln Leu Val Lys Ile Asn
        525                 530                 535
```

<210> SEQ ID NO 5
<211> LENGTH: 1482

```
<212> TYPE: DNA
<213> ORGANISM: Paenibacillus sp.
<220> FEATURE:
<221> NAME/KEY: CDS
<222> LOCATION: (1)..(1482)
<220> FEATURE:
<221> NAME/KEY: mat_peptide
<222> LOCATION: (136)..(1479)

<400> SEQUENCE: 5

atg agc aaa cag aga gaa att gaa ccc att aaa gga gga att gtt ctg       48
Met Ser Lys Gln Arg Glu Ile Glu Pro Ile Lys Gly Gly Ile Val Leu
-45                 -40                 -35                 -30

ttc gca aaa aaa ctt gca aag ctt gtt ggt acg att gct ttg gcc gga       96
Phe Ala Lys Lys Leu Ala Lys Leu Val Gly Thr Ile Ala Leu Ala Gly
                -25                 -20                 -15

atg ctt att aca tcc ctc tcg gtt gat tat gca caa gct agt ctt gta      144
Met Leu Ile Thr Ser Leu Ser Val Asp Tyr Ala Gln Ala Ser Leu Val
            -10                 -5                  -1  1

agc ggc agc aaa ttt ttg ggc aat atc ata gca ggc agc gtc cca tcg      192
Ser Gly Ser Lys Phe Leu Gly Asn Ile Ile Ala Gly Ser Val Pro Ser
    5                   10                  15

agc ttc ggt acg tat tgg aat cag gta aca ccg gag aac ggg acc aaa      240
Ser Phe Gly Thr Tyr Trp Asn Gln Val Thr Pro Glu Asn Gly Thr Lys
20                  25                  30                  35

tgg ggc tcc gtc gaa ggc gcg cgc aac tcg atg aac tgg ggg caa gcg      288
Trp Gly Ser Val Glu Gly Ala Arg Asn Ser Met Asn Trp Gly Gln Ala
                40                  45                  50

gac aca tct tat aac tat gcc aaa agc aat ggc atg cct ttc aag ttc      336
Asp Thr Ser Tyr Asn Tyr Ala Lys Ser Asn Gly Met Pro Phe Lys Phe
            55                  60                  65

cat acg ctc gtc tgg ggc agt caa gag ccg agc tgg gtc ggc agc ctg      384
His Thr Leu Val Trp Gly Ser Gln Glu Pro Ser Trp Val Gly Ser Leu
        70                  75                  80

tcg gcc gct gat cag aag gcg gaa gtt acg cag tgg att caa tta gcc      432
Ser Ala Ala Asp Gln Lys Ala Glu Val Thr Gln Trp Ile Gln Leu Ala
    85                  90                  95

ggc cag cga tat ggc ggc tcc gaa tac gtt gac gtc gtc aac gag cct      480
Gly Gln Arg Tyr Gly Gly Ser Glu Tyr Val Asp Val Val Asn Glu Pro
100                 105                 110                 115

ttg cac gcg aag ccg gat tac cgc aac gcc atc ggc ggc gac ggc gca      528
Leu His Ala Lys Pro Asp Tyr Arg Asn Ala Ile Gly Gly Asp Gly Ala
                120                 125                 130

acc gga tgg gat tgg atc atc tgg tcg ttc cag caa gcc cgg gca gca      576
Thr Gly Trp Asp Trp Ile Ile Trp Ser Phe Gln Gln Ala Arg Ala Ala
            135                 140                 145

ttc ccg aac tcc aaa ctg ctc att aat gag tac ggc atc att aac gat      624
Phe Pro Asn Ser Lys Leu Leu Ile Asn Glu Tyr Gly Ile Ile Asn Asp
        150                 155                 160

cct aac tta gcg gat caa tac gtc aat atc atc aac att cta aag agc      672
Pro Asn Leu Ala Asp Gln Tyr Val Asn Ile Ile Asn Ile Leu Lys Ser
    165                 170                 175

cgc gga ttg gtc gac ggc atc ggc atc caa tgt cac caa ttc agt atg      720
Arg Gly Leu Val Asp Gly Ile Gly Ile Gln Cys His Gln Phe Ser Met
180                 185                 190                 195

gac acc gta tcc gtc agc acg atg aat acg gtc ttg ggc aag ctg tcg      768
Asp Thr Val Ser Val Ser Thr Met Asn Thr Val Leu Gly Lys Leu Ser
                200                 205                 210

gca acc ggt ttg ccg att tat gta tcc gag ctc gac atg acc ggc gat      816
Ala Thr Gly Leu Pro Ile Tyr Val Ser Glu Leu Asp Met Thr Gly Asp
            215                 220                 225
```

```
gac gcg acc cag ctc gct cgg tat cag cag aag ttc cct gta ctg tgg      864
Asp Ala Thr Gln Leu Ala Arg Tyr Gln Gln Lys Phe Pro Val Leu Trp
        230                 235                 240

gag aat ccg aat gtg aaa ggc att acg ctg tgg ggc tat att caa ggc      912
Glu Asn Pro Asn Val Lys Gly Ile Thr Leu Trp Gly Tyr Ile Gln Gly
    245                 250                 255

cag acc tgg atc aac ggc acg cat ttg ctc aac tct aac ggc acg gag      960
Gln Thr Trp Ile Asn Gly Thr His Leu Leu Asn Ser Asn Gly Thr Glu
260                 265                 270                 275

cgt cct gcg ctc cag tgg ctg aaa act tat ctg agc gga aac aac gga     1008
Arg Pro Ala Leu Gln Trp Leu Lys Thr Tyr Leu Ser Gly Asn Asn Gly
                280                 285                 290

ggt tct gga ggt aca acc gcg agc att tat cat gac ttc gaa tcg ggc     1056
Gly Ser Gly Gly Thr Thr Ala Ser Ile Tyr His Asp Phe Glu Ser Gly
            295                 300                 305

acg gaa ggc tgg gct ggc gga act att agc ggc gga cca tgg tcc acc     1104
Thr Glu Gly Trp Ala Gly Gly Thr Ile Ser Gly Gly Pro Trp Ser Thr
        310                 315                 320

acg gca tgg gcc tcc aag aat acc cac tcc ctg caa gta gac atc ccg     1152
Thr Ala Trp Ala Ser Lys Asn Thr His Ser Leu Gln Val Asp Ile Pro
    325                 330                 335

atg gca agc ggt tcg gcg cac tac atg tac aaa acc ggc acc ttc aac     1200
Met Ala Ser Gly Ser Ala His Tyr Met Tyr Lys Thr Gly Thr Phe Asn
340                 345                 350                 355

gtg acg ggc ttc aat cag ctc cgg gca acc gta cac ggt tcc aca tgg     1248
Val Thr Gly Phe Asn Gln Leu Arg Ala Thr Val His Gly Ser Thr Trp
                360                 365                 370

ggc ggc tat ggt tct ggc ttg ggc gtt aag ctg tat gtc aaa tac ggc     1296
Gly Gly Tyr Gly Ser Gly Leu Gly Val Lys Leu Tyr Val Lys Tyr Gly
            375                 380                 385

agc aac tac gcc tgg aaa gac agc ggc tgg gcg aca ata ggc gcg aac     1344
Ser Asn Tyr Ala Trp Lys Asp Ser Gly Trp Ala Thr Ile Gly Ala Asn
        390                 395                 400

ggc acg atc aac ctc acg ctc gat ctg acg ggc att gat aaa acc aat     1392
Gly Thr Ile Asn Leu Thr Leu Asp Leu Thr Gly Ile Asp Lys Thr Asn
    405                 410                 415

atc aag gaa tac ggt att cag ttc att gac gca agc aat tct tcc ggc     1440
Ile Lys Glu Tyr Gly Ile Gln Phe Ile Asp Ala Ser Asn Ser Ser Gly
420                 425                 430                 435

aca gca tcg gtg tac gtc gat aac gtg tat ctg tgg aat taa             1482
Thr Ala Ser Val Tyr Val Asp Asn Val Tyr Leu Trp Asn
                440                 445


<210> SEQ ID NO 6
<211> LENGTH: 493
<212> TYPE: PRT
<213> ORGANISM: Paenibacillus sp.

<400> SEQUENCE: 6

Met Ser Lys Gln Arg Glu Ile Glu Pro Ile Lys Gly Gly Ile Val Leu
-45                 -40                 -35                 -30

Phe Ala Lys Lys Leu Ala Lys Leu Val Gly Thr Ile Ala Leu Ala Gly
                -25                 -20                 -15

Met Leu Ile Thr Ser Leu Ser Val Asp Tyr Ala Gln Ala Ser Leu Val
            -10                 -5              -1  1

Ser Gly Ser Lys Phe Leu Gly Asn Ile Ile Ala Gly Ser Val Pro Ser
    5                   10                  15

Ser Phe Gly Thr Tyr Trp Asn Gln Val Thr Pro Glu Asn Gly Thr Lys
20                  25                  30                  35
```

```
Trp Gly Ser Val Glu Gly Ala Arg Asn Ser Met Asn Trp Gly Gln Ala
                40                  45                  50

Asp Thr Ser Tyr Asn Tyr Ala Lys Ser Asn Gly Met Pro Phe Lys Phe
            55                  60                  65

His Thr Leu Val Trp Gly Ser Gln Glu Pro Ser Trp Val Gly Ser Leu
        70                  75                  80

Ser Ala Ala Asp Gln Lys Ala Glu Val Thr Gln Trp Ile Gln Leu Ala
    85                  90                  95

Gly Gln Arg Tyr Gly Gly Ser Glu Tyr Val Asp Val Val Asn Glu Pro
100                 105                 110                 115

Leu His Ala Lys Pro Asp Tyr Arg Asn Ala Ile Gly Gly Asp Gly Ala
                120                 125                 130

Thr Gly Trp Asp Trp Ile Ile Trp Ser Phe Gln Gln Ala Arg Ala Ala
            135                 140                 145

Phe Pro Asn Ser Lys Leu Leu Ile Asn Glu Tyr Gly Ile Ile Asn Asp
        150                 155                 160

Pro Asn Leu Ala Asp Gln Tyr Val Asn Ile Ile Asn Ile Leu Lys Ser
    165                 170                 175

Arg Gly Leu Val Asp Gly Ile Gly Ile Gln Cys His Gln Phe Ser Met
180                 185                 190                 195

Asp Thr Val Ser Val Ser Thr Met Asn Thr Val Leu Gly Lys Leu Ser
                200                 205                 210

Ala Thr Gly Leu Pro Ile Tyr Val Ser Glu Leu Asp Met Thr Gly Asp
            215                 220                 225

Asp Ala Thr Gln Leu Ala Arg Tyr Gln Gln Lys Phe Pro Val Leu Trp
        230                 235                 240

Glu Asn Pro Asn Val Lys Gly Ile Thr Leu Trp Gly Tyr Ile Gln Gly
    245                 250                 255

Gln Thr Trp Ile Asn Gly Thr His Leu Leu Asn Ser Asn Gly Thr Glu
260                 265                 270                 275

Arg Pro Ala Leu Gln Trp Leu Lys Thr Tyr Leu Ser Gly Asn Asn Gly
                280                 285                 290

Gly Ser Gly Gly Thr Thr Ala Ser Ile Tyr His Asp Phe Glu Ser Gly
            295                 300                 305

Thr Glu Gly Trp Ala Gly Gly Thr Ile Ser Gly Gly Pro Trp Ser Thr
        310                 315                 320

Thr Ala Trp Ala Ser Lys Asn Thr His Ser Leu Gln Val Asp Ile Pro
    325                 330                 335

Met Ala Ser Gly Ser Ala His Tyr Met Tyr Lys Thr Gly Thr Phe Asn
340                 345                 350                 355

Val Thr Gly Phe Asn Gln Leu Arg Ala Thr Val His Gly Ser Thr Trp
                360                 365                 370

Gly Gly Tyr Gly Ser Gly Leu Gly Val Lys Leu Tyr Val Lys Tyr Gly
            375                 380                 385

Ser Asn Tyr Ala Trp Lys Asp Ser Gly Trp Ala Thr Ile Gly Ala Asn
        390                 395                 400

Gly Thr Ile Asn Leu Thr Leu Asp Leu Thr Gly Ile Asp Lys Thr Asn
    405                 410                 415

Ile Lys Glu Tyr Gly Ile Gln Phe Ile Asp Ala Ser Asn Ser Ser Gly
420                 425                 430                 435

Thr Ala Ser Val Tyr Val Asp Asn Val Tyr Leu Trp Asn
                440                 445
```

```
<210> SEQ ID NO 7
<211> LENGTH: 10
<212> TYPE: PRT
<213> ORGANISM: Paenibacillus sp.

<400> SEQUENCE: 7

Ala Thr Asp Tyr Trp Gln Asn Trp Thr Asp
1               5                   10


<210> SEQ ID NO 8
<211> LENGTH: 636
<212> TYPE: DNA
<213> ORGANISM: Paenibacillus sp.
<220> FEATURE:
<221> NAME/KEY: CDS
<222> LOCATION: (1)..(636)
<220> FEATURE:
<221> NAME/KEY: mat_peptide
<222> LOCATION: (85)..(633)

<400> SEQUENCE: 8

atg atg aaa tgg acg aag aaa gcg gtt ttg act gtt ctg gca gca aca       48
Met Met Lys Trp Thr Lys Lys Ala Val Leu Thr Val Leu Ala Ala Thr
            -25                 -20                 -15

atg agc atg ggc atg ttt gcg gca acc tca agt gcg gca act gac tat       96
Met Ser Met Gly Met Phe Ala Ala Thr Ser Ser Ala Ala Thr Asp Tyr
        -10                 -5              -1  1

tgg cag aat tgg acg gac ggc ggc ggc acg gtt aac gcg gtg aac ggt      144
Trp Gln Asn Trp Thr Asp Gly Gly Gly Thr Val Asn Ala Val Asn Gly
5                   10                  15                  20

tcc ggc ggc aat tac agc gtc aat tgg tct aac acc ggc aat ttt gtc      192
Ser Gly Gly Asn Tyr Ser Val Asn Trp Ser Asn Thr Gly Asn Phe Val
                25                  30                  35

gtc ggc aag ggt tgg acc gta ggc tca cct aca cgg acg atc aac tac      240
Val Gly Lys Gly Trp Thr Val Gly Ser Pro Thr Arg Thr Ile Asn Tyr
            40                  45                  50

aat gcg ggc gta tgg gcg cca tct ggc aat ggc tat ctg acg ctc tat      288
Asn Ala Gly Val Trp Ala Pro Ser Gly Asn Gly Tyr Leu Thr Leu Tyr
        55                  60                  65

ggc tgg aca cgc aat tcg ctg atc gaa tat tat gtc gta gat tca tgg      336
Gly Trp Thr Arg Asn Ser Leu Ile Glu Tyr Tyr Val Val Asp Ser Trp
    70                  75                  80

ggc acc tat cgt cct acg gga acg tac aaa gga tcg gta acg agc gat      384
Gly Thr Tyr Arg Pro Thr Gly Thr Tyr Lys Gly Ser Val Thr Ser Asp
85                  90                  95                  100

gga ggc aca tac gat atc tac acg gct act cgc tat aat gcg cct tcc      432
Gly Gly Thr Tyr Asp Ile Tyr Thr Ala Thr Arg Tyr Asn Ala Pro Ser
                105                 110                 115

atc gat ggc acg gca acg ttt acg cag tac tgg agc gtt cgt cag tcg      480
Ile Asp Gly Thr Ala Thr Phe Thr Gln Tyr Trp Ser Val Arg Gln Ser
            120                 125                 130

aag cgt gca acg ggc agc aac gtc gcg atc aca ttc gct aat cac gtt      528
Lys Arg Ala Thr Gly Ser Asn Val Ala Ile Thr Phe Ala Asn His Val
        135                 140                 145

aac gca tgg aag agc aaa ggc atg aat ctg ggc agc agc tgg act tat      576
Asn Ala Trp Lys Ser Lys Gly Met Asn Leu Gly Ser Ser Trp Thr Tyr
    150                 155                 160

cag gtt ctg gcg acg gaa ggc tac caa agc agc ggc agc tcg aac gta      624
Gln Val Leu Ala Thr Glu Gly Tyr Gln Ser Ser Gly Ser Ser Asn Val
165                 170                 175                 180

acg gtc tgg taa                                                      636
Thr Val Trp
```

```
<210> SEQ ID NO 9
<211> LENGTH: 211
<212> TYPE: PRT
<213> ORGANISM: Paenibacillus sp.

<400> SEQUENCE: 9

Met Met Lys Trp Thr Lys Lys Ala Val Leu Thr Val Leu Ala Ala Thr
            -25                 -20                 -15

Met Ser Met Gly Met Phe Ala Ala Thr Ser Ser Ala Ala Thr Asp Tyr
        -10                 -5              -1  1

Trp Gln Asn Trp Thr Asp Gly Gly Gly Thr Val Asn Ala Val Asn Gly
5                   10                  15                  20

Ser Gly Gly Asn Tyr Ser Val Asn Trp Ser Asn Thr Gly Asn Phe Val
                25                  30                  35

Val Gly Lys Gly Trp Thr Val Gly Ser Pro Thr Arg Thr Ile Asn Tyr
            40                  45                  50

Asn Ala Gly Val Trp Ala Pro Ser Gly Asn Gly Tyr Leu Thr Leu Tyr
        55                  60                  65

Gly Trp Thr Arg Asn Ser Leu Ile Glu Tyr Tyr Val Val Asp Ser Trp
    70                  75                  80

Gly Thr Tyr Arg Pro Thr Gly Thr Tyr Lys Gly Ser Val Thr Ser Asp
85                  90                  95                  100

Gly Gly Thr Tyr Asp Ile Tyr Thr Ala Thr Arg Tyr Asn Ala Pro Ser
                105                 110                 115

Ile Asp Gly Thr Ala Thr Phe Thr Gln Tyr Trp Ser Val Arg Gln Ser
            120                 125                 130

Lys Arg Ala Thr Gly Ser Asn Val Ala Ile Thr Phe Ala Asn His Val
        135                 140                 145

Asn Ala Trp Lys Ser Lys Gly Met Asn Leu Gly Ser Ser Trp Thr Tyr
    150                 155                 160

Gln Val Leu Ala Thr Glu Gly Tyr Gln Ser Ser Gly Ser Ser Asn Val
165                 170                 175                 180

Thr Val Trp


<210> SEQ ID NO 10
<211> LENGTH: 14
<212> TYPE: PRT
<213> ORGANISM: Paenibacillus sp.
<220> FEATURE:
<221> NAME/KEY: misc_feature
<222> LOCATION: (9)..(9)
<223> OTHER INFORMATION: Xaa can be any naturally occurring amino acid

<400> SEQUENCE: 10

Ala Ser Asp Ala Ile Val Asn Leu Xaa Ala Glu Lys Gln Leu
1               5                   10


<210> SEQ ID NO 11
<211> LENGTH: 1692
<212> TYPE: DNA
<213> ORGANISM: Paenibacillus sp.
<220> FEATURE:
<221> NAME/KEY: CDS
<222> LOCATION: (1)..(1692)
<220> FEATURE:
<221> NAME/KEY: mat_peptide
<222> LOCATION: (109)..(1689)

<400> SEQUENCE: 11

atg aat gca gtg aaa gta ggt tta aga aag tca atc agc ttg ctt ctc       48
```

-continued

```
Met Asn Ala Val Lys Val Gly Leu Arg Lys Ser Ile Ser Leu Leu Leu
    -35                 -30                 -25

gca tgc gta acc gct ctg tca tgt ctg tta acg aca agt tac tct aac       96
Ala Cys Val Thr Ala Leu Ser Cys Leu Leu Thr Thr Ser Tyr Ser Asn
-20                 -15                 -10                 -5

gag gta tca gcg gcg agc gac gca ata gtc aat cta tcg gca gag aag      144
Glu Val Ser Ala Ala Ser Asp Ala Ile Val Asn Leu Ser Ala Glu Lys
            -1  1               5                   10

cag ttg att cgg ggc ttt ggc ggc atg aac cat ccg gtg tgg aca acg      192
Gln Leu Ile Arg Gly Phe Gly Gly Met Asn His Pro Val Trp Thr Thr
        15                  20                  25

gac ttg acc gct gcg cag cgg gaa acg gtt ttc ggc aat ggc aac aac      240
Asp Leu Thr Ala Ala Gln Arg Glu Thr Val Phe Gly Asn Gly Asn Asn
    30                  35                  40

cag ctt gga ttc tcc gtt ctg cgg att cat gtc gat gag gat ccg aac      288
Gln Leu Gly Phe Ser Val Leu Arg Ile His Val Asp Glu Asp Pro Asn
45                  50                  55                  60

aat tgg tac aaa gag ctt ccg acc gca cag agc gcg att gcg cac ggc      336
Asn Trp Tyr Lys Glu Leu Pro Thr Ala Gln Ser Ala Ile Ala His Gly
                65                  70                  75

gcg atc gta ttc gct acg ccg tgg aac ccg cca agc agc atg acg gag      384
Ala Ile Val Phe Ala Thr Pro Trp Asn Pro Pro Ser Ser Met Thr Glu
            80                  85                  90

acg ttc aat cgc aac ggc gat acg aca gcg aag agg ctg cgt tac gat      432
Thr Phe Asn Arg Asn Gly Asp Thr Thr Ala Lys Arg Leu Arg Tyr Asp
        95                  100                 105

aag tat gcg gct tat gct cag cat ctg aat gat ttt gta aca tat atg      480
Lys Tyr Ala Ala Tyr Ala Gln His Leu Asn Asp Phe Val Thr Tyr Met
    110                 115                 120

aaa aat aac ggc gtc aat ctg tat gcc atc tcg gtc cag aat gaa cct      528
Lys Asn Asn Gly Val Asn Leu Tyr Ala Ile Ser Val Gln Asn Glu Pro
125                 130                 135                 140

gat tac gcg cat aca tgg aca tgg tgg acg ccg gaa gag atg ctt cgt      576
Asp Tyr Ala His Thr Trp Thr Trp Trp Thr Pro Glu Glu Met Leu Arg
                145                 150                 155

ttc atg aag gaa aat gca ggc tcc atc aat tgc aaa gtg atg gcg ccg      624
Phe Met Lys Glu Asn Ala Gly Ser Ile Asn Cys Lys Val Met Ala Pro
            160                 165                 170

gaa tct ttc caa tat ctt aag aac atg tcc gac ccg ata ctg aac gac      672
Glu Ser Phe Gln Tyr Leu Lys Asn Met Ser Asp Pro Ile Leu Asn Asp
        175                 180                 185

gcg caa gcg ctt gcg aat atg gac att ctg gga gcc cat acg tac ggt      720
Ala Gln Ala Leu Ala Asn Met Asp Ile Leu Gly Ala His Thr Tyr Gly
    190                 195                 200

acg ccg ttc agc agc ttc gcc tac ccg cta ttc aag cag aaa gga gcc      768
Thr Pro Phe Ser Ser Phe Ala Tyr Pro Leu Phe Lys Gln Lys Gly Ala
205                 210                 215                 220

ggc aaa gaa ctg tgg atg acg gaa gtc tat tat ccg aat agc gac gcc      816
Gly Lys Glu Leu Trp Met Thr Glu Val Tyr Tyr Pro Asn Ser Asp Ala
                225                 230                 235

aac tcg gcg gat cgc tgg cct gaa gct ttg gat gtt gcg tat cat atg      864
Asn Ser Ala Asp Arg Trp Pro Glu Ala Leu Asp Val Ala Tyr His Met
            240                 245                 250

cac aac gcg atg gtc gaa gga gat ttt caa acc tat gta tgg tgg tat      912
His Asn Ala Met Val Glu Gly Asp Phe Gln Thr Tyr Val Trp Trp Tyr
        255                 260                 265

att cgc agg caa tac ggt cca ttg aaa gag gat gga acg ata agc aaa      960
Ile Arg Arg Gln Tyr Gly Pro Leu Lys Glu Asp Gly Thr Ile Ser Lys
    270                 275                 280
```

```
cgc ggt tac tcc atg gct caa ttc tcg aag ttc gtt cgc cct ggc tat      1008
Arg Gly Tyr Ser Met Ala Gln Phe Ser Lys Phe Val Arg Pro Gly Tyr
285                 290                 295                 300

gtc agg gtc gat gca acg aag aac ccg gat acg aac gtc tat gta tct      1056
Val Arg Val Asp Ala Thr Lys Asn Pro Asp Thr Asn Val Tyr Val Ser
                305                 310                 315

gct tat aaa ggg agc ggc aag gtt gtt atc gta gcg att aac aga ggg      1104
Ala Tyr Lys Gly Ser Gly Lys Val Val Ile Val Ala Ile Asn Arg Gly
            320                 325                 330

aca tct gcc gtg agt caa cga ttc gtg ctg cag aac gga aca gca tcg      1152
Thr Ser Ala Val Ser Gln Arg Phe Val Leu Gln Asn Gly Thr Ala Ser
        335                 340                 345

caa gta aca cca tac gtt acg gat gga acg aga aac acg gca gcg caa      1200
Gln Val Thr Pro Tyr Val Thr Asp Gly Thr Arg Asn Thr Ala Ala Gln
    350                 355                 360

agc aac att agc gta tcg aat ggc gcc ttc aca gcc cag ctt ccg gct      1248
Ser Asn Ile Ser Val Ser Asn Gly Ala Phe Thr Ala Gln Leu Pro Ala
365                 370                 375                 380

cag agc gtg aca acc ttc gtg ggc gat tac agc acg ggc ggc acg gga      1296
Gln Ser Val Thr Thr Phe Val Gly Asp Tyr Ser Thr Gly Gly Thr Gly
                385                 390                 395

ggc ggc agc agt acg acg tat gaa gca gag acg ggc aca acc ttg acg      1344
Gly Gly Ser Ser Thr Thr Tyr Glu Ala Glu Thr Gly Thr Thr Leu Thr
            400                 405                 410

aac gcc gta acc gaa acg ctg tac aca ggc tat aac ggt act ggc tat      1392
Asn Ala Val Thr Glu Thr Leu Tyr Thr Gly Tyr Asn Gly Thr Gly Tyr
        415                 420                 425

gtc aat ttt aat gct tat tcg gat gca gcc att cag tgg aac aat gta      1440
Val Asn Phe Asn Ala Tyr Ser Asp Ala Ala Ile Gln Trp Asn Asn Val
    430                 435                 440

tat tgc gcc gta tcc gga acg aaa aat gtg aaa ttc cgg tac gca ctc      1488
Tyr Cys Ala Val Ser Gly Thr Lys Asn Val Lys Phe Arg Tyr Ala Leu
445                 450                 455                 460

gca tcc ggt aca aga aac ctc gat gta tac gtg aat gga acc aaa gtg      1536
Ala Ser Gly Thr Arg Asn Leu Asp Val Tyr Val Asn Gly Thr Lys Val
                465                 470                 475

atc agc aat gca gcc ttc gcg gcg act ggc agt tgg acg aca tgg gga      1584
Ile Ser Asn Ala Ala Phe Ala Ala Thr Gly Ser Trp Thr Thr Trp Gly
            480                 485                 490

gag caa acg atc cag gtc gca atg aac agc gga acg aat acg att cgg      1632
Glu Gln Thr Ile Gln Val Ala Met Asn Ser Gly Thr Asn Thr Ile Arg
        495                 500                 505

gtc gta acg acc ggc acg gag ggg ccg aat atc gat agt ata aat gta      1680
Val Val Thr Thr Gly Thr Glu Gly Pro Asn Ile Asp Ser Ile Asn Val
    510                 515                 520

tcg gca cag taa                                                      1692
Ser Ala Gln
525
```

<210> SEQ ID NO 12
<211> LENGTH: 563
<212> TYPE: PRT
<213> ORGANISM: Paenibacillus sp.

<400> SEQUENCE: 12

```
Met Asn Ala Val Lys Val Gly Leu Arg Lys Ser Ile Ser Leu Leu Leu
    -35                 -30                 -25

Ala Cys Val Thr Ala Leu Ser Cys Leu Leu Thr Thr Ser Tyr Ser Asn
-20                 -15                 -10                 -5

Glu Val Ser Ala Ala Ser Asp Ala Ile Val Asn Leu Ser Ala Glu Lys
```

-continued

```
            -1  1               5                   10

Gln Leu Ile Arg Gly Phe Gly Gly Met Asn His Pro Val Trp Thr Thr
        15                  20                  25

Asp Leu Thr Ala Ala Gln Arg Glu Thr Val Phe Gly Asn Gly Asn Asn
    30                  35                  40

Gln Leu Gly Phe Ser Val Leu Arg Ile His Val Asp Glu Asp Pro Asn
45                  50                  55                  60

Asn Trp Tyr Lys Glu Leu Pro Thr Ala Gln Ser Ala Ile Ala His Gly
            65                  70                  75

Ala Ile Val Phe Ala Thr Pro Trp Asn Pro Pro Ser Ser Met Thr Glu
            80                  85                  90

Thr Phe Asn Arg Asn Gly Asp Thr Thr Ala Lys Arg Leu Arg Tyr Asp
        95                  100                 105

Lys Tyr Ala Ala Tyr Ala Gln His Leu Asn Asp Phe Val Thr Tyr Met
    110                 115                 120

Lys Asn Asn Gly Val Asn Leu Tyr Ala Ile Ser Val Gln Asn Glu Pro
125                 130                 135                 140

Asp Tyr Ala His Thr Trp Thr Trp Trp Thr Pro Glu Glu Met Leu Arg
                145                 150                 155

Phe Met Lys Glu Asn Ala Gly Ser Ile Asn Cys Lys Val Met Ala Pro
            160                 165                 170

Glu Ser Phe Gln Tyr Leu Lys Asn Met Ser Asp Pro Ile Leu Asn Asp
        175                 180                 185

Ala Gln Ala Leu Ala Asn Met Asp Ile Leu Gly Ala His Thr Tyr Gly
    190                 195                 200

Thr Pro Phe Ser Ser Phe Ala Tyr Pro Leu Phe Lys Gln Lys Gly Ala
205                 210                 215                 220

Gly Lys Glu Leu Trp Met Thr Glu Val Tyr Tyr Pro Asn Ser Asp Ala
                225                 230                 235

Asn Ser Ala Asp Arg Trp Pro Glu Ala Leu Asp Val Ala Tyr His Met
            240                 245                 250

His Asn Ala Met Val Glu Gly Asp Phe Gln Thr Tyr Val Trp Trp Tyr
        255                 260                 265

Ile Arg Arg Gln Tyr Gly Pro Leu Lys Glu Asp Gly Thr Ile Ser Lys
    270                 275                 280

Arg Gly Tyr Ser Met Ala Gln Phe Ser Lys Phe Val Arg Pro Gly Tyr
285                 290                 295                 300

Val Arg Val Asp Ala Thr Lys Asn Pro Asp Thr Asn Val Tyr Val Ser
                305                 310                 315

Ala Tyr Lys Gly Ser Gly Lys Val Val Ile Val Ala Ile Asn Arg Gly
            320                 325                 330

Thr Ser Ala Val Ser Gln Arg Phe Val Leu Gln Asn Gly Thr Ala Ser
        335                 340                 345

Gln Val Thr Pro Tyr Val Thr Asp Gly Thr Arg Asn Thr Ala Ala Gln
    350                 355                 360

Ser Asn Ile Ser Val Ser Asn Gly Ala Phe Thr Ala Gln Leu Pro Ala
365                 370                 375                 380

Gln Ser Val Thr Thr Phe Val Gly Asp Tyr Ser Thr Gly Gly Thr Gly
                385                 390                 395

Gly Gly Ser Ser Thr Thr Tyr Glu Ala Glu Thr Gly Thr Thr Leu Thr
            400                 405                 410

Asn Ala Val Thr Glu Thr Leu Tyr Thr Gly Tyr Asn Gly Thr Gly Tyr
        415                 420                 425
```

```
Val Asn Phe Asn Ala Tyr Ser Asp Ala Ala Ile Gln Trp Asn Asn Val
    430                 435                 440

Tyr Cys Ala Val Ser Gly Thr Lys Asn Val Lys Phe Arg Tyr Ala Leu
445                 450                 455                 460

Ala Ser Gly Thr Arg Asn Leu Asp Val Tyr Val Asn Gly Thr Lys Val
                465                 470                 475

Ile Ser Asn Ala Ala Phe Ala Ala Thr Gly Ser Trp Thr Thr Trp Gly
            480                 485                 490

Glu Gln Thr Ile Gln Val Ala Met Asn Ser Gly Thr Asn Thr Ile Arg
        495                 500                 505

Val Val Thr Thr Gly Thr Glu Gly Pro Asn Ile Asp Ser Ile Asn Val
    510                 515                 520

Ser Ala Gln
525


<210> SEQ ID NO 13
<211> LENGTH: 1905
<212> TYPE: DNA
<213> ORGANISM: Paenibacillus sp.
<220> FEATURE:
<221> NAME/KEY: CDS
<222> LOCATION: (1)..(1905)
<220> FEATURE:
<221> NAME/KEY: mat_peptide
<222> LOCATION: (79)..(1902)

<400> SEQUENCE: 13

atg ttt aag aaa ttg agt tct tta tta tta tcg ctc act ttg ctg tta       48
Met Phe Lys Lys Leu Ser Ser Leu Leu Leu Ser Leu Thr Leu Leu Leu
    -25                 -20                 -15

agc tgt tta tcc tta acg tcc gcg tat gcc gct aac agc tct att gcg       96
Ser Cys Leu Ser Leu Thr Ser Ala Tyr Ala Ala Asn Ser Ser Ile Ala
-10                 -5              -1  1               5

aaa aac ccg gga aac agt aat cca ttg atg gat cac aaa tta ggg gca      144
Lys Asn Pro Gly Asn Ser Asn Pro Leu Met Asp His Lys Leu Gly Ala
            10                  15                  20

gac cct ttc gca ctg acc tat aac ggt cga gtc tac gtc tac atg tca      192
Asp Pro Phe Ala Leu Thr Tyr Asn Gly Arg Val Tyr Val Tyr Met Ser
        25                  30                  35

agc gat gct tat gtt tac aac agc aac gga acg atc aaa gac aat gac      240
Ser Asp Ala Tyr Val Tyr Asn Ser Asn Gly Thr Ile Lys Asp Asn Asp
    40                  45                  50

tac agc gct ttg aac aaa atc aat gtg atc tcc tcc gcc gac atg gtg      288
Tyr Ser Ala Leu Asn Lys Ile Asn Val Ile Ser Ser Ala Asp Met Val
55                  60                  65                  70

aac tgg acg gat cat ggt tcc att ccg gta gca ggc tat aat aat gca      336
Asn Trp Thr Asp His Gly Ser Ile Pro Val Ala Gly Tyr Asn Asn Ala
                75                  80                  85

aat aat gga gcg ggc att gcc aag tgg gcg tcg ctc tct tgg gcg ccg      384
Asn Asn Gly Ala Gly Ile Ala Lys Trp Ala Ser Leu Ser Trp Ala Pro
            90                  95                  100

tcg gtc gcc aaa aag acg att aac gga aag gat aag ttt ttc ctc tat      432
Ser Val Ala Lys Lys Thr Ile Asn Gly Lys Asp Lys Phe Phe Leu Tyr
        105                 110                 115

ttc ggc aat ggc gca tca gga atc ggc gta ctc aca tcg gac acg cca      480
Phe Gly Asn Gly Ala Ser Gly Ile Gly Val Leu Thr Ser Asp Thr Pro
    120                 125                 130

ata gga cca tgg tca gat ccg ctt ggc aaa gcg ctt gtg acg ctc aat      528
Ile Gly Pro Trp Ser Asp Pro Leu Gly Lys Ala Leu Val Thr Leu Asn
135                 140                 145                 150
```

-continued

```
acg cca ggt atg tcc ggc gtt acc tgg ctg ttt gat ccg gca gtg ctc      576
Thr Pro Gly Met Ser Gly Val Thr Trp Leu Phe Asp Pro Ala Val Leu
                155                 160                 165

gta gac gac gac ggt aca ggt tat ctg tac atg ggt ggc ggc atc cca      624
Val Asp Asp Asp Gly Thr Gly Tyr Leu Tyr Met Gly Gly Gly Ile Pro
            170                 175                 180

aat aat tca gat ccg gcg atc atc gcg aat ccg aag acg gcc aga gtc      672
Asn Asn Ser Asp Pro Ala Ile Ile Ala Asn Pro Lys Thr Ala Arg Val
        185                 190                 195

atc agg cta ggt gct gat atg acg agt gtt aac gga agc gct gtc atg      720
Ile Arg Leu Gly Ala Asp Met Thr Ser Val Asn Gly Ser Ala Val Met
    200                 205                 210

att gat gcc cct tat atg ttc gaa gat tcg ggc att cat aag tac aac      768
Ile Asp Ala Pro Tyr Met Phe Glu Asp Ser Gly Ile His Lys Tyr Asn
215                 220                 225                 230

ggc aaa tac tac tat tcg tat tgc atg aat ttc tca ggt acg cat cca      816
Gly Lys Tyr Tyr Tyr Ser Tyr Cys Met Asn Phe Ser Gly Thr His Pro
                235                 240                 245

gct gct tat cca gca ggt gaa atc ggc tat atg gtg agc agc agt ccg      864
Ala Ala Tyr Pro Ala Gly Glu Ile Gly Tyr Met Val Ser Ser Ser Pro
            250                 255                 260

atg gga cca ttc acg tat gcg ggt cat ttt ctg aaa aac cct ggt gct      912
Met Gly Pro Phe Thr Tyr Ala Gly His Phe Leu Lys Asn Pro Gly Ala
        265                 270                 275

ttc ttc ggt tcg ggc ggc aat aac cat cat gca gtg ttt aac ttc aat      960
Phe Phe Gly Ser Gly Gly Asn Asn His His Ala Val Phe Asn Phe Asn
    280                 285                 290

aac cag tgg tat gtc gtc tat cac gct caa acc gtc agc caa gcg ctg     1008
Asn Gln Trp Tyr Val Val Tyr His Ala Gln Thr Val Ser Gln Ala Leu
295                 300                 305                 310

ctg gga tcg ggc aaa ggc tac cgc tct cct cat atc aat aag ctg ttc     1056
Leu Gly Ser Gly Lys Gly Tyr Arg Ser Pro His Ile Asn Lys Leu Phe
                315                 320                 325

tat aac gcg gac gga acg att caa gaa gtg caa gga aac atg gtt ggt     1104
Tyr Asn Ala Asp Gly Thr Ile Gln Glu Val Gln Gly Asn Met Val Gly
            330                 335                 340

gtt agt cag att gcc aat ctg aat cct tac aat cga acg gaa gcg gag     1152
Val Ser Gln Ile Ala Asn Leu Asn Pro Tyr Asn Arg Thr Glu Ala Glu
        345                 350                 355

acg atc ggc tgg aat gca ggg att acg acg gag gta agc caa gcg aca     1200
Thr Ile Gly Trp Asn Ala Gly Ile Thr Thr Glu Val Ser Gln Ala Thr
    360                 365                 370

ggc ggg ccg ttc aac aac atg gac gtg act aat att agc aat gga gat     1248
Gly Gly Pro Phe Asn Asn Met Asp Val Thr Asn Ile Ser Asn Gly Asp
375                 380                 385                 390

tgg gtc gcc gta ggc aat gct gat ttc ggc tcg agc ggg gcg aag tcg     1296
Trp Val Ala Val Gly Asn Ala Asp Phe Gly Ser Ser Gly Ala Lys Ser
                395                 400                 405

ttc aag gcg aat gta gca tct gtc gta ggc ggc agt att gaa atc cgt     1344
Phe Lys Ala Asn Val Ala Ser Val Val Gly Gly Ser Ile Glu Ile Arg
            410                 415                 420

ctt gac agc ccg aca ggt acg ctc gtc ggt acc ttg aat gtg cct tct     1392
Leu Asp Ser Pro Thr Gly Thr Leu Val Gly Thr Leu Asn Val Pro Ser
        425                 430                 435

acc gga gga acg cag aac tgg caa gaa cta agt aca aca gta agc aat     1440
Thr Gly Gly Thr Gln Asn Trp Gln Glu Leu Ser Thr Thr Val Ser Asn
    440                 445                 450

gca aca ggc gtg cac aaa gtt ttc ttt gtg ttc aca gga tcg agc gcc     1488
Ala Thr Gly Val His Lys Val Phe Phe Val Phe Thr Gly Ser Ser Ala
```

455 460 465 470 agc agc ttg ttc aac ttt gat tac tgg cag ttc tcg caa aat tca tcg 1536
Ser Ser Leu Phe Asn Phe Asp Tyr Trp Gln Phe Ser Gln Asn Ser Ser
475 480 485 acc tcg aat gga aca agg ata gaa gta gag gat atg acg att ggt ggt 1584
Thr Ser Asn Gly Thr Arg Ile Glu Val Glu Asp Met Thr Ile Gly Gly
490 495 500 cca tat ggc gga aag gta agt tct cct ttc aat ggc ggg gtg ttc tac 1632
Pro Tyr Gly Gly Lys Val Ser Ser Pro Phe Asn Gly Gly Val Phe Tyr
505 510 515 gct aac aat gat tat gcc tcg tac aat caa tat ttt gcg ttt tcc acc 1680
Ala Asn Asn Asp Tyr Ala Ser Tyr Asn Gln Tyr Phe Ala Phe Ser Thr
520 525 530 cac aca ttc tcg ctt cgc ggt gca tcc agc aac acc tcg aca gcg cgg 1728
His Thr Phe Ser Leu Arg Gly Ala Ser Ser Asn Thr Ser Thr Ala Arg
535 540 545 550 atc gac ctg caa att aat gga acg acg gtc ggt tcc ttc tac ttc acc 1776
Ile Asp Leu Gln Ile Asn Gly Thr Thr Val Gly Ser Phe Tyr Phe Thr
555 560 565 gga acg acg cca act gtc cag acg ttg tct aat gtc tcg cat gcg aca 1824
Gly Thr Thr Pro Thr Val Gln Thr Leu Ser Asn Val Ser His Ala Thr
570 575 580 gga cct gta gaa gtc aag cta atc gtt aca acc gat aat ggc aca tgg 1872
Gly Pro Val Glu Val Lys Leu Ile Val Thr Thr Asp Asn Gly Thr Trp
585 590 595 gat gtc tac gcc gat tat ttg gaa tac acc tag 1905
Asp Val Tyr Ala Asp Tyr Leu Glu Tyr Thr
600 605

<210> SEQ ID NO 14
<211> LENGTH: 634
<212> TYPE: PRT
<213> ORGANISM: Paenibacillus sp.

<400> SEQUENCE: 14

Met Phe Lys Lys Leu Ser Ser Leu Leu Leu Ser Leu Thr Leu Leu Leu
-25 -20 -15

Ser Cys Leu Ser Leu Thr Ser Ala Tyr Ala Ala Asn Ser Ser Ile Ala
-10 -5 -1 1 5

Lys Asn Pro Gly Asn Ser Asn Pro Leu Met Asp His Lys Leu Gly Ala
10 15 20

Asp Pro Phe Ala Leu Thr Tyr Asn Gly Arg Val Tyr Val Tyr Met Ser
25 30 35

Ser Asp Ala Tyr Val Tyr Asn Ser Asn Gly Thr Ile Lys Asp Asn Asp
40 45 50

Tyr Ser Ala Leu Asn Lys Ile Asn Val Ile Ser Ser Ala Asp Met Val
55 60 65 70

Asn Trp Thr Asp His Gly Ser Ile Pro Val Ala Gly Tyr Asn Asn Ala
75 80 85

Asn Asn Gly Ala Gly Ile Ala Lys Trp Ala Ser Leu Ser Trp Ala Pro
90 95 100

Ser Val Ala Lys Lys Thr Ile Asn Gly Lys Asp Lys Phe Phe Leu Tyr
105 110 115

Phe Gly Asn Gly Ala Ser Gly Ile Gly Val Leu Thr Ser Asp Thr Pro
120 125 130

Ile Gly Pro Trp Ser Asp Pro Leu Gly Lys Ala Leu Val Thr Leu Asn
135 140 145 150

-continued

```
Thr Pro Gly Met Ser Gly Val Thr Trp Leu Phe Asp Pro Ala Val Leu
                155                 160                 165

Val Asp Asp Asp Gly Thr Gly Tyr Leu Tyr Met Gly Gly Gly Ile Pro
            170                 175                 180

Asn Asn Ser Asp Pro Ala Ile Ile Ala Asn Pro Lys Thr Ala Arg Val
        185                 190                 195

Ile Arg Leu Gly Ala Asp Met Thr Ser Val Asn Gly Ser Ala Val Met
    200                 205                 210

Ile Asp Ala Pro Tyr Met Phe Glu Asp Ser Gly Ile His Lys Tyr Asn
215                 220                 225                 230

Gly Lys Tyr Tyr Tyr Ser Tyr Cys Met Asn Phe Ser Gly Thr His Pro
                235                 240                 245

Ala Ala Tyr Pro Ala Gly Glu Ile Gly Tyr Met Val Ser Ser Ser Pro
            250                 255                 260

Met Gly Pro Phe Thr Tyr Ala Gly His Phe Leu Lys Asn Pro Gly Ala
        265                 270                 275

Phe Phe Gly Ser Gly Gly Asn Asn His His Ala Val Phe Asn Phe Asn
    280                 285                 290

Asn Gln Trp Tyr Val Val Tyr His Ala Gln Thr Val Ser Gln Ala Leu
295                 300                 305                 310

Leu Gly Ser Gly Lys Gly Tyr Arg Ser Pro His Ile Asn Lys Leu Phe
                315                 320                 325

Tyr Asn Ala Asp Gly Thr Ile Gln Glu Val Gln Gly Asn Met Val Gly
            330                 335                 340

Val Ser Gln Ile Ala Asn Leu Asn Pro Tyr Asn Arg Thr Glu Ala Glu
        345                 350                 355

Thr Ile Gly Trp Asn Ala Gly Ile Thr Thr Glu Val Ser Gln Ala Thr
    360                 365                 370

Gly Gly Pro Phe Asn Asn Met Asp Val Thr Asn Ile Ser Asn Gly Asp
375                 380                 385                 390

Trp Val Ala Val Gly Asn Ala Asp Phe Gly Ser Ser Gly Ala Lys Ser
                395                 400                 405

Phe Lys Ala Asn Val Ala Ser Val Val Gly Gly Ser Ile Glu Ile Arg
            410                 415                 420

Leu Asp Ser Pro Thr Gly Thr Leu Val Gly Thr Leu Asn Val Pro Ser
        425                 430                 435

Thr Gly Gly Thr Gln Asn Trp Gln Glu Leu Ser Thr Thr Val Ser Asn
    440                 445                 450

Ala Thr Gly Val His Lys Val Phe Phe Val Phe Thr Gly Ser Ser Ala
455                 460                 465                 470

Ser Ser Leu Phe Asn Phe Asp Tyr Trp Gln Phe Ser Gln Asn Ser Ser
                475                 480                 485

Thr Ser Asn Gly Thr Arg Ile Glu Val Glu Asp Met Thr Ile Gly Gly
            490                 495                 500

Pro Tyr Gly Gly Lys Val Ser Ser Pro Phe Asn Gly Gly Val Phe Tyr
        505                 510                 515

Ala Asn Asn Asp Tyr Ala Ser Tyr Asn Gln Tyr Phe Ala Phe Ser Thr
    520                 525                 530

His Thr Phe Ser Leu Arg Gly Ala Ser Ser Asn Thr Ser Thr Ala Arg
535                 540                 545                 550

Ile Asp Leu Gln Ile Asn Gly Thr Thr Val Gly Ser Phe Tyr Phe Thr
                555                 560                 565

Gly Thr Thr Pro Thr Val Gln Thr Leu Ser Asn Val Ser His Ala Thr
```

570 575 580

Gly Pro Val Glu Val Lys Leu Ile Val Thr Thr Asp Asn Gly Thr Trp
585 590 595

Asp Val Tyr Ala Asp Tyr Leu Glu Tyr Thr
600 605

<210> SEQ ID NO 15
<211> LENGTH: 37
<212> TYPE: DNA
<213> ORGANISM: Artificial Sequence
<220> FEATURE:
<223> OTHER INFORMATION: Primer P1

<400> SEQUENCE: 15
aaggagatat acatatgagt cttgtaagcg gcagcaa 37

<210> SEQ ID NO 16
<211> LENGTH: 36
<212> TYPE: DNA
<213> ORGANISM: Artificial Sequence
<220> FEATURE:
<223> OTHER INFORMATION: Primer P2

<400> SEQUENCE: 16
ggtggtggtg ctcgagattc cacagataca cgttat 36

<210> SEQ ID NO 17
<211> LENGTH: 37
<212> TYPE: DNA
<213> ORGANISM: Artificial Sequence
<220> FEATURE:
<223> OTHER INFORMATION: Primer P3

<400> SEQUENCE: 17
aaggagatat acatatggcg agcgacgcaa tagtcaa 37

<210> SEQ ID NO 18
<211> LENGTH: 36
<212> TYPE: DNA
<213> ORGANISM: Artificial Sequence
<220> FEATURE:
<223> OTHER INFORMATION: Primer P4

<400> SEQUENCE: 18
ggtggtggtg ctcgagctgt gccgatacat ttatac 36

<210> SEQ ID NO 19
<211> LENGTH: 37
<212> TYPE: DNA
<213> ORGANISM: Artificial Sequence
<220> FEATURE:
<223> OTHER INFORMATION: Primer P5

<400> SEQUENCE: 19
aaggagatat acatatggca actgactatt ggcagaa 37

<210> SEQ ID NO 20
<211> LENGTH: 36
<212> TYPE: DNA
<213> ORGANISM: Artificial Sequence
<220> FEATURE:
<223> OTHER INFORMATION: Primer P6

<400> SEQUENCE: 20
ggtggtggtg ctcgagccag accgttacgt tcgagc 36

```
<210> SEQ ID NO 21
<211> LENGTH: 34
<212> TYPE: DNA
<213> ORGANISM: Artificial Sequence
<220> FEATURE:
<223> OTHER INFORMATION: Primer P7

<400> SEQUENCE: 21

aaggagatat acatatgttt aagaaattga gttc                          34


<210> SEQ ID NO 22
<211> LENGTH: 36
<212> TYPE: DNA
<213> ORGANISM: Artificial Sequence
<220> FEATURE:
<223> OTHER INFORMATION: Primer P8

<400> SEQUENCE: 22

ggtggtggtg ctcgagggtg tattccaaat aatcgg                        36


<210> SEQ ID NO 23
<211> LENGTH: 37
<212> TYPE: DNA
<213> ORGANISM: Artificial Sequence
<220> FEATURE:
<223> OTHER INFORMATION: Primer P9

<400> SEQUENCE: 23

accacagcca ggatccgtgg tcaggcatgc agatgtc                       37


<210> SEQ ID NO 24
<211> LENGTH: 35
<212> TYPE: DNA
<213> ORGANISM: Artificial Sequence
<220> FEATURE:
<223> OTHER INFORMATION: Primer P10

<400> SEQUENCE: 24

atgcggccgc aagctttaat tgattttgac taatt                         35


<210> SEQ ID NO 25
<211> LENGTH: 10
<212> TYPE: PRT
<213> ORGANISM: Paenibacillus sp.

<400> SEQUENCE: 25

Asn Phe Ser Gly Ile Ala Lys Asn Pro Gly
1               5                   10


<210> SEQ ID NO 26
<211> LENGTH: 565
<212> TYPE: PRT
<213> ORGANISM: Paenibacillus sp.
<220> FEATURE:
<221> NAME/KEY: mat_peptide
<222> LOCATION: (30)..(565)

<400> SEQUENCE: 26

Met Lys Lys Met Arg Trp Thr Ile Lys Leu Leu Leu Ala Leu Val Met
                -25                 -20                 -15

Val Val Pro Thr Leu Met Asp Ser Gln Arg Ala Asp Ala Trp Thr Gly
            -10                 -5              -1  1

Met Pro Met Ser Lys Leu His Val Ser Gly Asn Gln Leu Val Asn Ser
    5                   10                  15
```

```
Ser Gly Gln Pro Val Leu Leu Ser Gly Trp His Gln Pro Ser Gly Ser
20                  25                  30                  35

Tyr Trp Thr Tyr Gln Ser Ser Lys Tyr Tyr Leu Asp Arg Asn Gly Gly
                40                  45                  50

Asn Arg His Ala Ala Ile Leu Glu Tyr Leu Lys Asp Ile Thr Asp Thr
            55                  60                  65

Phe Thr Asp Thr Ser Ala Lys Tyr Gly Ser Ser His Gly Trp Tyr Met
        70                  75                  80

Asn Gln Val Arg Leu Phe Ile Asp Arg Glu Asp Met Gly Asp Val Ala
    85                  90                  95

Ala Gly Thr Tyr Asn Phe Ala Gly Leu Gln Ser Val Thr Gln Asn Val
100                 105                 110                 115

Ile Ile Pro Tyr Ile Ala Tyr Ala Lys Thr Lys Gly Leu Tyr Val Thr
                120                 125                 130

Leu Gly Leu Asp Phe Thr Leu Ser Asn Asn Gln Ala Thr Thr Pro Ser
            135                 140                 145

Asn Leu Asn Lys Phe Asn Glu Ile Trp Gly Tyr Leu Ala Ser Gln Pro
        150                 155                 160

Ala Ile Lys Ser Ala Asp Asn Val Met Phe Glu Leu Ile Asn Glu Pro
    165                 170                 175

Val Leu Ser Asp Val Asn Gly Gln Trp Gly Gly Asn Pro Ser Gln Pro
180                 185                 190                 195

Asn Phe Ala Asp Tyr Trp Asn Ser Leu Lys Lys Phe Gln Asn Ser Ile
                200                 205                 210

Ile Ser Thr Ile Arg Ser Lys Gly Ala Asp Asn Val Ile Trp Ala Ala
            215                 220                 225

Gly Leu Gly Trp Asp Gln Tyr Tyr Gln Leu Cys Ala Ser Ser Pro Leu
        230                 235                 240

Thr Asp Pro Leu Asn Asn Ile Gly Tyr Ser Val His Trp Tyr Pro Gly
    245                 250                 255

Tyr Gly Ala His Asp Asp Tyr Ala Thr Leu Gln Gln Gln Trp Asp Thr
260                 265                 270                 275

Asn Ile Lys Pro Cys Ala Asp His Tyr Pro Ile Asn Ile Thr Glu Thr
                280                 285                 290

Thr Trp Phe Lys Thr Gln Pro Gly Asp Ser Ser Tyr Trp Glu Leu Phe
            295                 300                 305

Asn Gly Ser Asn Glu Gly Phe Gly Lys Asn Thr Lys Ala Ile Phe Thr
        310                 315                 320

Ala Ala Gly Asn Val Ser Met Thr Ala His Met Asn Gly Phe Leu Leu
    325                 330                 335

Glu Pro Gly Pro Arg Ser Ser Phe Ala Asp Pro Thr Ala Gly Leu Lys
340                 345                 350                 355

Tyr Asp Gly Asn Ala Ala Arg Asp Gly Met Ala Arg Phe Leu Phe Glu
                360                 365                 370

Trp Tyr Tyr Glu Arg Ala Gln Leu Asn Pro Trp Asn Gly Ile Trp Asn
            375                 380                 385

Gly Val Leu Ser Gly Ser Thr Tyr Lys Ile Leu Asn Arg Ala Ser Gly
        390                 395                 400

Lys Ala Ile Asp Val Pro Gly Gly Gln Asn Thr Asn Gly Leu Gln Leu
    405                 410                 415

Gln Gln Trp Thr Asp Asn Gln Ala Thr Ala Gln Gln Trp Val Ala Ser
420                 425                 430                 435
```

```
Asp Met Gly Thr Tyr Asn Asn Val Tyr Lys Leu Arg Ser Val Ser Ser
                440                 445                 450

Ala Asp Gln Lys Val Met Asp Ile Arg Asn Gly Thr Lys Asn Asn Gly
            455                 460                 465

Glu Ala Val Gln Leu Met Gln Asp Leu Gly Asn Ala Ala Gln Gln Phe
        470                 475                 480

Arg Leu Ile Lys Leu Ser Asn Gly Tyr Trp Ser Ile Leu Asn Val Asn
    485                 490                 495

Ser Asn Lys Ala Val Glu Val Ala Gly Ala Ser Ser Ser Asp Gly Ala
500                 505                 510                 515

Lys Leu Gln Gln Asn Leu Tyr Arg Gly Asn Pro Asn Gln Gln Trp Gln
                520                 525                 530

Leu Val Lys Ile Asn
            535


<210> SEQ ID NO 27
<211> LENGTH: 1698
<212> TYPE: DNA
<213> ORGANISM: Paenibacillus sp.

<400> SEQUENCE: 27

gtgaagaaaa tgagatggac catcaagctt ttgctggctc tggtcatggt agtgccgacg     60

ctaatggaca gccagcgcgc agatgcatgg accggcatgc ccatgtccaa gctccacgtt    120

agcggcaacc agctggtgaa cagcagcgga cagcccgtcc tgctaagcgg ctggcatcag    180

ccctcgggct cctattggac ctaccagtcc agcaagtact acctggatcg gaacggaggg    240

aaccggcatg cggccatttt ggagtacttg aaggatatca ccgatacctt taccgatacg    300

tctgccaaat acggcagcag ccacggctgg tacatgaatc aggtccggct gtttattgac    360

cgggaagaca tgggcgatgt agccgccggc acctataatt ttgccggttt gcaaagtgtt    420

acgcaaaacg tcatcattcc gtatattgcc tatgccaaga caaagggcct gtatgttacg    480

ctggggctcg atttcactct ttccaacaac caggcgacca ccccatccaa tctgaacaag    540

ttcaacgaaa tctggggtta ccttgcctcc caaccggcga tcaaaagcgc ggacaacgtg    600

atgttcgaac tgatcaatga accggtcctg tccgatgtca acgggcaatg ggcggaaat    660

ccctctcaac ccaatttcgc cgattactgg aactccctta aaaaattcca aaactccatc    720

atatccacca tacgcagtaa aggtgccgac aacgtgatat gggcggcggg gcttggctgg    780

gatcaatact accagctgtg cgcgtccagt ccgctgaccg atcccttgaa caatatcggg    840

tattccgtcc actggtaccc agggtacggt gcccatgacg attatgcgac tttgcagcag    900

cagtgggata cgaatattaa gccctgcgcc gatcattatc ccatcaacat tacggagacc    960

acctggttca agacgcagcc cggcgattcc tcctactggg agctgttcaa cgggtccaat   1020

gaaggtttcg gcaaaaacac gaaggccata ttcacagcgg ccggcaatgt cagcatgacc   1080

gcccatatga acgggttttt gctggagccc ggcccaagaa gttcttttgc tgacccgacc   1140

gcaggcctca aatatgacgg caatgccgca cgggacggca tggcccgttt tctcttcgaa   1200

tggtattatg aacgcgcgca gctgaatcct tggaacggga tctggaacgg ggttttgtcc   1260

ggctcgacct ataagatcct gaaccgcgct tcgggcaaag cgattgacgt gcctggcgga   1320

cagaatacca acgggctgca gcttcagcag tggacagaca accaagcgac agcccagcaa   1380

tgggttgcca gtgatatggg gacttacaac aatgtgtaca agctgcgaag cgtcagctcg   1440

gccgaccaaa aagtcatgga tatccggaac ggcacgaaga acaacggcga agcggtccaa   1500
```

```
ctcatgcagg acttggggaa tgccgcacag caattcagat tgatcaaact gagcaacggt   1560

tactggagca tcctgaatgt gaacagcaac aaggccgtcg aggttgccgg agcctcatcc   1620

tcggatggag cgaagcttca gcaaaatctc taccggggca atccgaacca gcaatggcag   1680

ctggtaaaaa tcaattag                                                 1698


<210> SEQ ID NO 28
<211> LENGTH: 568
<212> TYPE: PRT
<213> ORGANISM: Paenibacillus sp.
<220> FEATURE:
<221> NAME/KEY: mat_peptide
<222> LOCATION: (33)..(568)

<400> SEQUENCE: 28

Met Lys Lys Ser Asn Ser Ser Trp Ile Leu Lys Leu Phe Thr Leu Met
        -30                 -25                 -20

Ala Leu Met Leu Thr Pro Ser Leu Leu Asn Ser His Pro Ala Lys Ala
    -15                 -10                 -5                  -1

Trp Ser Gly Met Thr Met Ser Lys Leu His Ala Ser Gly Asn Gln Leu
1               5                   10                  15

Val Asn Ser Ser Gly Gln Pro Val Leu Leu Ser Gly Trp His Gln Pro
            20                  25                  30

Ser Gly Ser Tyr Trp Thr Tyr Gln Asp Ser Lys Tyr Tyr Leu Asp Gln
        35                  40                  45

Tyr Gly Gly Asn Arg His Ala Ala Val Leu Ala Tyr Leu Lys Asp Ile
    50                  55                  60

Thr Asp Thr Phe Thr Asn Thr Ser Ser Lys Tyr Gly Asn Ser His Gly
65                  70                  75                  80

Trp Tyr Met Asn Gln Val Arg Leu Phe Ile Asp Arg Glu Asp Met Gly
                85                  90                  95

Asp Val Ala Ala Gly Thr Tyr Asn Phe Ala Gly Leu Gln Ser Val Thr
            100                 105                 110

Gln Asp Val Ile Ile Pro Tyr Ile Asn Tyr Ala Lys Thr Lys Gly Val
        115                 120                 125

Tyr Val Thr Leu Gly Leu Asp Phe Thr Ile Leu Asn Asn Gln Ala Thr
    130                 135                 140

Thr Gln Ala Asn Leu Asp Lys Phe Asn Gln Ile Trp Gly Tyr Leu Ser
145                 150                 155                 160

Ser Gln Ser Ala Ile Lys Ser Ala Asp Asn Val Met Phe Glu Leu Ile
                165                 170                 175

Asn Glu Pro Val Gln Ala Phe Ala Asn Gly Ser Trp Gly Gly Asn Pro
            180                 185                 190

Ala Gln Ser Asp Phe Val Ala Tyr Trp Asn Ser Leu Lys Thr Phe Gln
        195                 200                 205

Asn Ser Ile Ile Ser Thr Ile Arg Asn Asn Gly Ala Asp Asn Val Ile
    210                 215                 220

Trp Ala Ala Gly Leu Gly Trp Asp Gln Tyr Tyr Gln Leu Cys Ala Ser
225                 230                 235                 240

Tyr Pro Leu Thr Asp Pro Leu Asn Asn Tyr Gly Tyr Ala Val His Trp
                245                 250                 255

Tyr Pro Gly Tyr Gly Ala His Asp Asp Tyr Ala Ala Leu Gln Gln Ile
            260                 265                 270

Trp Asp Asp Thr Ile Lys Pro Cys Ala Asn Asn Tyr Pro Ile Asn Ile
        275                 280                 285
```

```
Thr Glu Thr Thr Trp Phe Lys Thr Leu Ser Gly Asp Ser Ser Tyr Trp
    290                 295                 300

Asp Leu Phe Asn Gly Ser Asn Glu Gly Phe Gly Lys Asn Thr Lys Ala
305                 310                 315                 320

Ile Phe Thr Ala Ala Gly Asn Val Ser Ile Ala Val His Met Asn Gly
                325                 330                 335

Phe Leu Leu Glu Pro Gly Thr Arg Ser Ser Phe Ala Asp Pro Thr Ala
            340                 345                 350

Gly Leu Lys Tyr Asp Gly Asn Thr Ala Arg Asp Gly Met Ala Arg Phe
        355                 360                 365

Ile Phe Glu Trp Tyr Tyr Glu Arg Ala Gln Leu His Pro Trp Asn Gly
    370                 375                 380

Ile Trp Asn Gly Ile Gln Ser Gly Ser Thr Tyr Lys Ile Ile Asn Arg
385                 390                 395                 400

Ala Ser Gly Lys Ala Leu Glu Val Pro Gly Gly Gln Asn Thr Asn Ala
                405                 410                 415

Leu Gln Leu Gln Gln Tyr Thr Asp Asn Gly Ala Thr Ala Gln Gln Trp
            420                 425                 430

Val Ile Thr Asp Gln Gly Thr Tyr Asn Asn Tyr Tyr Lys Leu Arg Ser
        435                 440                 445

Val Ser Ser Ser Asp Asn Lys Val Met Asp Val Arg Asn Gly Thr Lys
    450                 455                 460

Asn Asn Gly Glu Ala Ile Gln Leu Met Ser Asp Tyr Asn Asn Thr Ala
465                 470                 475                 480

Gln Gln Phe Arg Leu Ile Lys Leu Ser Ser Gly Tyr Trp Ser Ile Ile
                485                 490                 495

Asn Val Asn Ser Asn Lys Ala Val Glu Val Ala Asn Ser Ser Thr Asn
            500                 505                 510

Asn Ser Ala Leu Ile Gln Gln Asn Met Tyr Arg Gly Asn Pro Asn Gln
        515                 520                 525

Gln Trp Gln Leu Val Lys Ile Asn
    530                 535
```

```
<210> SEQ ID NO 29
<211> LENGTH: 1707
<212> TYPE: DNA
<213> ORGANISM: Paenibacillus sp.

<400> SEQUENCE: 29

atgaaaaaga gcaattcaag ctggattctg aagctgttca ccctaatggc gcttatgcta      60

acgccatcct tgctgaacag tcatccggcg aaagcgtggt cgggaatgac catgtccaag     120

cttcatgcaa gcggcaatca gctggtgaac agcagcgggc agcccgtgct cctgagcgga     180

tggcatcaac cttccggttc gtattggacg taccaggaca gcaaatatta tctggatcaa     240

tacggcggga acagacatgc ggcggttctg gcgtatctga aggacattac ggatactttc     300

accaatacat caagtaaata cggcaacagc cacggctggt atatgaacca ggttcgcttg     360

tttatcgatc gcgaggacat gggcgatgtc gcggcaggca catacaattt cgcaggactg     420

caatccgtaa cccaggacgt tatcattcca tacatcaact atgccaagac caaaggggta     480

tacgtcacgc ttggccttga cttcactatt cttaataacc aggcgacaac gcaagccaat     540

ctcgataaat tcaatcaaat ctggggttat ctgtcctccc aatcggctat caagagtgcg     600

gataacgtca tgttcgagct tatcaacgag cccgttcaag ccttcgccaa cggctcctgg     660

ggaggcaatc ctgcgcaaag cgactttgtt gcctactgga attcactcaa gaccttccag     720
```

```
aattccatca tttccacgat ccggaataac ggtgcagaca atgtgatctg ggcggccggg     780

cttggctggg atcaatacta ccagctgtgt gcttcctatc cgctgacgga tccgctcaac     840

aattacgggt atgccgttca ttggtatccg ggttacggcg cccatgacga ttatgccgct     900

cttcagcaga tctgggatga tacgatcaag ccttgcgcca acaattaccc gatcaatatt     960

accgaaacga catggttcaa gacgttatcc ggcgactctt cttattggga cctgttcaac    1020

ggctccaacg agggcttcgg caaaaatacg aaagccatct tcacggcggc gggcaatgtc    1080

agcatagccg ttcatatgaa cggtttcttg ctcgagcccg gcaccagaag ctccttcgcc    1140

gatccgacgg ccggcttgaa gtacgacggc aatacagcaa gggacggaat ggcccggttt    1200

attttcgaat ggtattatga gcgggcgcag ctgcatccat ggaacggaat ctggaatggc    1260

atccagtcgg gatcgaccta caaaatcata aaccgggcct cgggaaaagc gcttgaggta    1320

ccgggggggcc agaatacgaa cgccttgcag cttcagcaat atacggataa tggcgctacc    1380

gcccaacaat gggtgattac ggatcaaggt acctataaca attactataa acttcgaagc    1440

gtcagctctt ccgacaacaa agtcatggac gtacgcaacg ggacaaagaa caacggggaa    1500

gccattcagc tcatgtccga ttacaataat accgctcagc agttccggct gattaagctg    1560

agcagcggat attggagcat cattaacgta aatagcaaca aagcagttga ggttgccaat    1620

tcttcgacaa acaactccgc tttgatccaa cagaatatgt atcggggcaa cccgaatcag    1680

cagtggcaac tggtgaaaat caactag                                        1707
```

```
<210> SEQ ID NO 30
<211> LENGTH: 565
<212> TYPE: PRT
<213> ORGANISM: Bacillus caseinilyticus
<220> FEATURE:
<221> NAME/KEY: mat_peptide
<222> LOCATION: (30)..(565)

<400> SEQUENCE: 30

Met Lys Lys Val Gly Trp Thr Val Lys Leu Leu Leu Val Met Ile Leu
                -25                 -20                 -15

Val Val Pro Ala Leu Leu Asn Ser Ser Pro Ala Lys Ala Trp Thr Gly
            -10                 -5              -1  1

Met Pro Met Asp Lys Leu His Val Ser Gly Asn Gln Leu Val Asn Ser
    5                   10                  15

Asn Gly Gln Pro Val Leu Leu Ser Gly Trp His Gln Pro Ser Gly Ser
20                  25                  30                  35

Tyr Trp Thr Tyr Gln Ser Ser Asn Tyr Tyr Leu Asn Arg Asn Gly Gly
                40                  45                  50

Asn Arg His Ala Ala Thr Leu Glu Tyr Leu Lys Asp Ile Thr Asp Thr
            55                  60                  65

Phe Thr Asp Thr Ser Pro Lys Tyr Gly Asn Asp His Gly Trp Tyr Met
        70                  75                  80

Asn Gln Ile Arg Leu Phe Ile Asp Arg Glu Asp Met Gly Asp Val Ala
    85                  90                  95

Gly Gly Thr Tyr Asn Phe Ala Gly Leu Gln Ala Val Thr Gln Asn Val
100                 105                 110                 115

Ile Ile Pro Tyr Val Glu Tyr Ala Lys Thr Lys Gly Leu Tyr Val Thr
                120                 125                 130

Leu Gly Leu Asp Phe Thr Leu Gln Asn Asn Gln Ala Thr Thr Gln Ala
            135                 140                 145
```

```
Asn Leu Asp Lys Phe Asn Glu Ile Trp Gly Tyr Leu Ala Ser Gln Pro
        150                 155                 160

Ala Leu Arg Ser Ala Asp Asn Val Met Phe Glu Ile Ile Asn Glu Pro
    165                 170                 175

Val Leu Ser Tyr Ala Asn Gly Lys Trp Gly Gly His Pro Ser Glu Pro
180                 185                 190                 195

Asp Phe Glu Ala His Trp Asn Ala Leu Arg Asp Phe Gln Asn Ser Ile
                200                 205                 210

Ile Ser Thr Ile Arg Asn Lys Gly Ala Asp Asn Val Ile Trp Ala Ala
            215                 220                 225

Gly Leu Gly Trp Asp Gln Tyr Tyr Gln Leu Cys Ala Ser His Pro Leu
        230                 235                 240

Thr Asp Pro Leu Asn Asn Thr Gly Tyr Ala Val His Trp Tyr Pro Gly
    245                 250                 255

Tyr Gly Ala Asn Asp Asn Tyr Ser Ile Leu Gln Gln Gln Trp Asp Thr
260                 265                 270                 275

Asn Ile Lys Pro Cys Ala Glu His Tyr Pro Ile Asn Ile Thr Glu Thr
                280                 285                 290

Thr Trp Tyr Lys Trp Leu Pro Gly Asp Pro Glu Tyr Trp Arg Leu Phe
            295                 300                 305

Asp Gly Thr Asn Glu Gly Phe Gly Lys Asn Thr Lys Ala Ile Phe Thr
        310                 315                 320

Ala Ala Gly Asn Val Ser Ile Ala Val His Met Asn Gly Phe Leu Leu
    325                 330                 335

Glu Pro Gly Thr Arg Ser Thr Phe Ala Asp Pro Thr Ala Gly Leu Lys
340                 345                 350                 355

Tyr Asp Gly Asp Lys Ala Arg Asp Gly Met Ala Arg Phe Leu Phe Glu
                360                 365                 370

Trp Tyr Tyr Glu Arg Ala Gln Leu Tyr Pro Trp Asn Gly Ile Trp Asn
            375                 380                 385

Ala Ile His Thr Gly Ala Thr Tyr Lys Leu Gln Asn Arg Ala Ser Gly
        390                 395                 400

Lys Met Ile Asp Val Pro Gly Gly Gln Asn Thr Asn Ala Leu Gln Leu
    405                 410                 415

Gln Gln Trp Ser Asp Asn Gly Ala Thr Ala Gln Gln Trp Val Val Asp
420                 425                 430                 435

Asp Val Gly Val Tyr Asn Asn Tyr Tyr Arg Leu Arg Ser Val Ser Ser
                440                 445                 450

Ser Asp Asn Lys Val Met Asp Val Arg Asn Gly Thr Lys Ser Asn Gly
            455                 460                 465

Glu Ala Ile Gln Leu Met Thr Asp Phe Gly Asn Ser Ala Gln Gln Phe
        470                 475                 480

Arg Leu Ile Arg Leu Ser Asn Gly Tyr Trp Ser Ile Leu Asn Val Asn
    485                 490                 495

Ser Asn Lys Ala Val Glu Val Ala Gly Ser Ser Ala Ala Asp Gly Ala
500                 505                 510                 515

Lys Leu Gln Gln Asn Met Tyr Arg Gly Asp Leu Asn Gln Gln Trp Asn
                520                 525                 530

Leu Ile Arg Ile Asn
            535
```

<210> SEQ ID NO 31
<211> LENGTH: 1698
<212> TYPE: DNA

<213> ORGANISM: Bacillus caseinilyticus

<400> SEQUENCE: 31

```
atgaaaaagg ttggttggac agtcaagctg ctgcttgtga tgatcctggt agttcccgct     60
ttgctgaaca gcagtccggc aaaggcgtgg acgggtatgc caatggacaa gctccatgta    120
agtggcaatc aattagtgaa cagtaatgga cagccggttt tattaagcgg ctggcatcag    180
ccttcaggtt cttattggac gtaccaaagc agtaattact acttgaacag aaatggcggt    240
aatcgtcatg cggcaactct cgagtacctg aaagatatta cagacacatt taccgacaca    300
tcgccgaaat atggaaacga tcacgggtgg tatatgaatc agattcggct gttcatcgat    360
cgggaagata tgggcgatgt tgcagggggg acatacaatt tcgccggttt gcaggccgtt    420
actcaaaatg tcattattcc ttatgttgaa tatgccaaga caaaaggtct ttatgttaca    480
ctcggccttg acttcactct gcaaaataat caagcgacga cgcaagcgaa ccttgataag    540
ttcaatgaga tttggggtta tcttgcgtcg cagccggcat tgagaagcgc ggacaatgtc    600
atgtttgaaa ttattaatga gccggttctt tcctacgcaa acggaaaatg gggcgggcac    660
ccgtccgagc cagactttga agctcactgg aacgccctta gagatttcca aaactctatc    720
atctctacga tccgaaacaa aggagcagat aacgtcattt gggcggcagg ccttggatgg    780
gatcaatatt atcagttatg cgcttctcat ccgctgacag accctttaaa taataccggc    840
tatgccgttc attggtatcc aggatatggc gctaatgaca attactctat tcttcagcag    900
caatgggata caaatattaa gccgtgcgcg gaacattatc ccattaatat cacggaaaca    960
acttggtata agtggcttcc gggagaccct gaatattggc gcttgtttga tggtacaaat   1020
gaaggatttg ggaaaaatac aaaagctatt tttacagcag caggaaacgt cagtattgct   1080
gttcatatga atggattttt actggaaccc ggtacaagaa gtacgttcgc ggatccaaca   1140
gccggtttga aatacgacgg tgataaggca cgcgacggta tggcgcgctt tctctttgag   1200
tggtattacg agcgcgcgca actgtatcct tggaatggca tttggaatgc aatccatacc   1260
ggagcaacgt acaagcttca gaatcgcgca tccggaaaaa tgattgacgt gcctggggga   1320
caaaatacca acgcccttca actccaacag tggtccgaca atggtgcgac agcgcagcaa   1380
tgggtcgtgg atgatgtggg cgtgtacaat aattattacc ggctgcgtag tgtcagctcg   1440
tctgacaaca aagtaatgga tgttcgtaat ggtacaaaaa gtaatggaga agccattcag   1500
ttaatgactg attttggaaa tagcgcgcaa cagttcagat taatcagact aagcaatggt   1560
tactggagca tcctcaatgt gaacagcaat aaagccgtcg aggttgctgg ttcctcagcg   1620
gcagacggcg caaaattgca gcaaaatatg taccgtgggg acttaaatca acaatggaat   1680
ttgattagaa taaattaa                                                 1698
```

<210> SEQ ID NO 32
<211> LENGTH: 559
<212> TYPE: PRT
<213> ORGANISM: Paenibacillus sp.
<220> FEATURE:
<221> NAME/KEY: mat_peptide
<222> LOCATION: (31)..(559)

<400> SEQUENCE: 32

```
Met Arg Val Asn Ile Lys Lys Ser Val Leu Ile Leu Leu Ala Phe Leu
-30                 -25                 -20                 -15

Thr Ala Leu Pro Leu Ile Val Thr Pro Thr Gln Val Thr Ala Ala Ser
                -10                 -5              -1   1
```

```
Asp Ala Asn Ile Asn Leu Ser Ser Glu Lys Gln Leu Ile Lys Gly Phe
        5                   10                  15

Gly Gly Ile Asn His Pro Ala Trp Ile Gly Asp Leu Thr Pro Ala Gln
    20                  25                  30

Arg Glu Thr Ala Phe Gly Asn Gly Ala Asn Gln Leu Gly Phe Ser Ile
35                  40                  45                  50

Leu Arg Ile Tyr Val Asp Glu Asn Arg Asn Asn Trp Tyr Arg Glu Val
                55                  60                  65

Pro Thr Ala Gln Lys Ala Ile Glu Gln Gly Ala Ile Val Phe Ala Ser
            70                  75                  80

Pro Trp Asn Pro Pro Ser Asp Met Val Glu Thr Phe Asn Arg Asn Gly
        85                  90                  95

Asp Pro Asn Ala Lys Arg Leu Arg Tyr Asp Lys Tyr Ala Ala Tyr Ala
    100                 105                 110

Gln His Leu Asn Asp Phe Val Thr Tyr Met Lys Asn Asn Gly Val Asp
115                 120                 125                 130

Leu Tyr Ala Ile Ser Val Gln Asn Glu Pro Asp Tyr Ala His Glu Trp
                135                 140                 145

Thr Trp Trp Thr Pro Gln Glu Ile Leu Arg Phe Met Lys Glu Asn Ala
            150                 155                 160

Gly Ser Ile Gln Gly Thr Lys Val Met Ala Pro Glu Ser Phe Gln Tyr
        165                 170                 175

Leu Lys Asn Met Ser Asp Pro Ile Leu Asn Asp Pro Gly Ala Leu Ala
    180                 185                 190

Asn Met Asp Ile Leu Gly Ala His Thr Tyr Gly Thr Gln Ile Lys Asp
195                 200                 205                 210

Phe Ala Tyr Pro Leu Phe Lys Gln Lys Gly Ala Gly Lys Glu Leu Trp
                215                 220                 225

Met Thr Glu Val Tyr Tyr Pro Asn Ser Asp Asn Asn Ser Ser Asp Arg
            230                 235                 240

Trp Pro Glu Ala Leu Glu Val Ser Tyr His Met His Asn Ala Met Val
        245                 250                 255

Glu Gly Asp Phe Gln Ala Tyr Val Trp Trp Tyr Ile Arg Arg Gln Tyr
    260                 265                 270

Gly Pro Met Asn Glu Asn Gly Thr Ile Ser Lys Arg Gly Tyr Asn Met
275                 280                 285                 290

Ala His Phe Ser Lys Phe Val Arg Pro Gly Tyr Ile Arg Val Asp Ala
                295                 300                 305

Thr Lys Asn Pro Asp Thr Asn Thr Phe Val Ser Ala Tyr Lys Gly Asp
            310                 315                 320

Asn Lys Val Val Ile Val Ala Ile Asn Arg Gly Thr Ser Ala Ala Ser
        325                 330                 335

Gln Lys Phe Val Leu Gln Asn Gly Asn Ala Ser Thr Val Ser Ser Trp
    340                 345                 350

Val Thr Asp Ser Ser Arg Asn Met Ala Ser Gly Ala Pro Ile Thr Val
355                 360                 365                 370

Ser Ser Gly Ala Phe Thr Ala Gln Leu Pro Ala Gln Ser Val Thr Thr
                375                 380                 385

Phe Val Ala Asn Ile Thr Gly Gly Gly Gly Ser Pro Val Thr Gly Thr
            390                 395                 400

Thr Tyr Glu Ala Glu Thr Gly Thr Thr Leu Thr Asn Ala Ala Ile Glu
        405                 410                 415

Ser Leu Tyr Pro Gly Tyr Thr Gly Ser Gly Tyr Val Asn Phe Asn Ala
```

```
    420                 425                 430

Tyr Thr Asp Ser Ala Ile Gln Trp Asn Ala Ile Asn Asn Thr Ile Thr
435                 440                 445                 450

Gly Thr Lys Asn Ile Lys Phe Arg Tyr Ala Leu Glu Ser Gly Thr Arg
                455                 460                 465

Asn Leu Asp Ile Phe Val Asn Gly Thr Lys Val Ile Ser Asn Glu Pro
            470                 475                 480

Phe Pro Ala Thr Gly Ser Trp Ser Thr Trp Ser Glu Lys Ser Ile Gln
        485                 490                 495

Val Pro Met Asn Ala Gly Thr Asn Thr Leu Lys Ile Val Thr Thr Gly
    500                 505                 510

Thr Glu Gly Pro Asn Val Asp Asn Ile Thr Val Thr Ala Val Gln
515                 520                 525
```

```
<210> SEQ ID NO 33
<211> LENGTH: 1680
<212> TYPE: DNA
<213> ORGANISM: Paenibacillus sp.

<400> SEQUENCE: 33

ttgagagtga acataaaaaa atcagtcctt attttattgg catttttaac ggctctacct      60

ctgattgtaa ctccaacaca ggtgacagca gctagcgatg ctaacattaa tttgtcctct     120

gagaaacagc tcattaaagg atttggagga ataaaccatc ccgcctggat cggtgacctg     180

acaccagctc agcgtgaaac tgcctttggt aatggagcga atcagcttgg gttttcgatt     240

ctacgaatct acgtagatga gaatagaaat aattggtaca gagaggttcc taccgcacaa     300

aaagcgattg agcaaggagc cattgtattt gcttcaccct ggaacccacc gagtgatatg     360

gtcgaaacct ttaatcgcaa cggggatccg aacgccaaac gactgagata cgacaaatat     420

gcagcttacg ctcagcatct gaacgacttt gtcacttata tgaaaaacaa tggtgtagac     480

ctgtacgcca tttcggtgca aaacgagccg gattatgctc atgaatggac ctggtggaca     540

ccacaggaaa tcctccgttt catgaaagag aatgcgggat ctattcaagg caccaaggtt     600

atggcacctg aatcgtttca gtatctaaag aacatgtctg atccaatcct gaatgatcct     660

ggggcactgg ctaatatgga tattctagga gcacatacgt atggaactca gatcaaagat     720

tttgcatacc cgctctttaa gcaaaaaggt gcaggtaagg aactgtggat gaccgaagta     780

tattacccga acagtgacaa caattcatcg gaccgttggc cagaggcact ggaggtatcc     840

taccatatgc acaacgccat ggttgaagga gatttccagg cttatgtatg gtggtacatt     900

cggagacagt acggtcctat gaatgagaac ggcaccatta gtaaacgtgg atataatatg     960

gctcacttct ccaaatttgt gcgaccaggc tatatcagag tagatgcaac caaaaatcca    1020

gatacgaaca cttttgtttc cgcttacaaa ggtgataaca aagtcgtcat cgtcgccatt    1080

aatcgcggca cttcagctgc aagccaaaaa ttcgttctgc aaaatggaaa cgcatctact    1140

gtctcctcat gggttacaga tagcagtcgc aatatggcaa gcggagcacc gatcaccgta    1200

tcgtcgggag cctttacagc gcaacttcct gcccaaagtg taacgacgtt tgtagcaaat    1260

attactggcg gcggggggag tccagttact ggaaccacat acgaagcaga aacagggact    1320

acacttacta atgctgctat tgaatcactc tatccaggat acactggatc cggatatgtt    1380

aactttaatg cttacaccga ttctgcgatt cagtggaatg ccatcaataa cacgataaca    1440

ggtaccaaaa acataaagtt ccgatatgca ttggaaagcg ggacacgtaa cctcgatatt    1500

tttgtcaatg ggaccaaggt gatcagcaac gagcctttcc cggcaacggg aagctggtca    1560
```

```
acttggagcg agaagagcat tcaagtcccc atgaacgcgg gaaccaatac gttaaaaata   1620

gtaacaaccg gaactgaagg accaaatgtg gataacatta cagtgacagc tgttcaataa   1680


<210> SEQ ID NO 34
<211> LENGTH: 420
<212> TYPE: PRT
<213> ORGANISM: Bacillus amyloliquefaciens
<220> FEATURE:
<221> NAME/KEY: mat_peptide
<222> LOCATION: (31)..(420)

<400> SEQUENCE: 34

Met Lys Lys Leu Ile Cys Val Leu Leu Ala Tyr Val Thr Met Leu Ser
-30                 -25                 -20                 -15

Leu Met Leu Thr Gly Pro Ala Ala Ser Glu Val Ser Ala Ala Ser Asp
                -10                 -5              -1  1

Ala Thr Val Arg Leu Ser Ala Glu Lys Gln Val Ile Arg Gly Phe Gly
        5                   10                  15

Gly Met Asn His Pro Ala Trp Ile Gly Asp Leu Thr Ala Ala Gln Arg
    20                  25                  30

Glu Thr Ala Phe Gly Asn Gly Gln Asn Gln Leu Gly Phe Ser Ile Leu
35                  40                  45                  50

Arg Ile His Val Asp Glu Asn Arg Asn Asn Trp Tyr Arg Glu Val Glu
                55                  60                  65

Thr Ala Lys Ser Ala Ile Lys His Gly Ala Ile Val Phe Ala Ser Pro
            70                  75                  80

Trp Asn Pro Pro Ser Asp Met Val Glu Thr Phe Asn Arg Asn Gly Asp
        85                  90                  95

Thr Ser Ala Lys Arg Leu Arg Tyr Asp Lys Tyr Ala Ala Tyr Ala Lys
    100                 105                 110

His Leu Asn Asp Phe Val Thr Phe Met Lys Asn Asn Gly Val Asn Leu
115                 120                 125                 130

Tyr Ala Ile Ser Val Gln Asn Glu Pro Asp Tyr Ala His Asp Trp Thr
                135                 140                 145

Trp Trp Thr Pro Gln Glu Ile Leu Arg Phe Met Lys Glu Asn Ala Gly
            150                 155                 160

Ser Ile Asn Ala Arg Val Ile Ala Pro Glu Ser Phe Gln Tyr Leu Lys
        165                 170                 175

Asn Ile Ser Asp Pro Ile Leu Asn Asp Pro Lys Ala Leu Ala Asn Met
    180                 185                 190

Asp Ile Leu Gly Ala His Leu Tyr Gly Thr Gln Leu Asn Asn Phe Ala
195                 200                 205                 210

Tyr Pro Leu Phe Lys Gln Lys Gly Ala Gly Lys Asp Leu Trp Met Thr
                215                 220                 225

Glu Val Tyr Tyr Pro Asn Ser Asp Asn His Ser Ala Asp Arg Trp Pro
            230                 235                 240

Glu Ala Leu Asp Val Ser His His Ile His Asn Ser Met Val Glu Gly
        245                 250                 255

Asp Phe Gln Ala Tyr Val Trp Trp Tyr Ile Arg Arg Ser Tyr Gly Pro
    260                 265                 270

Met Lys Glu Asp Gly Thr Ile Ser Lys Arg Gly Tyr Asn Met Ala His
275                 280                 285                 290

Phe Ser Lys Phe Val Arg Pro Gly Tyr Val Arg Val Asp Ala Thr Lys
                295                 300                 305
```

-continued

```
Ser Pro Ala Ser Asn Val Tyr Val Ser Ala Tyr Lys Gly Asp Asn Lys
            310                 315                 320

Val Val Ile Val Ala Ile Asn Lys Asn Asn Ser Gly Val Asn Gln Asn
        325                 330                 335

Phe Val Leu Gln Asn Gly Ser Val Ser Gln Val Ser Arg Trp Ile Thr
    340                 345                 350

Ser Ser Ser Ser Asn Leu Gln Pro Gly Thr Asn Leu Asn Val Thr Asp
355                 360                 365                 370

Asn His Phe Trp Ala His Leu Pro Ala Gln Ser Val Thr Thr Phe Val
                375                 380                 385

Ala Asn Leu Arg
            390


<210> SEQ ID NO 35
<211> LENGTH: 1263
<212> TYPE: DNA
<213> ORGANISM: Bacillus amyloliquefaciens

<400> SEQUENCE: 35

gtgaaaaaat taatttgtgt attgttggca tatgtaacga tgctgtcgct catgttaacc      60

gggcctgccg cttctgaagt ttcagcagcc agtgacgcaa cagttcgtct atctgcagaa     120

aaacaagtga ttcgcggttt tggagggatg aatcacccgg cttggatcgg ggatcttaca     180

gcagctcaaa gagaaaccgc ctttggcaat ggacagaatc agttaggctt ttcaatttta     240

agaattcatg ttgatgaaaa tagaaacaat tggtacagag aagtggagac ggcaaagagt     300

gcgatcaaac acggagcaat cgtttttgct tctccctgga atccgccaag cgatatggtt     360

gagactttca atcggaatgg agacacatca gctaaacggc tgagatacga taagtacgcc     420

gcatacgcga agcatcttaa cgactttgtt accttcatga aaaataatgg cgtgaatctg     480

tatgcgattt ccgtccaaaa cgagcctgat tacgcacacg actggacgtg gtggacaccg     540

caagaaatac ttcgctttat gaaagagaac gccggctcga ttaatgcccg tgtcatcgcg     600

cctgagtcgt ttcaatactt aaaaaatata tcggatccga ttttgaatga tccgaaggcg     660

cttgccaata tggatattct tggcgctcat ctttatggta cacagcttaa caatttcgct     720

tatccactgt tcaaacaaaa aggagcagga aaagatcttt ggatgacgga agtatattat     780

ccgaacagtg acaatcattc tgcggaccgc tggcctgagg cattggatgt ttcgcaccat     840

attcacaatt cgatggtaga gggagatttt caggcttatg tatggtggta catccgcaga     900

tcatacggtc ctatgaaaga agacggtacg atcagcaagc gcggttacaa tatggctcat     960

ttctcgaagt ttgtccgtcc cggttatgtc agggttgatg cgacaaagag ccccgcttca    1020

aacgtttacg tatctgccta taaaggtgac aacaaagtcg ttatagttgc cattaataaa    1080

aacaactcag ggttaacca aaacttcgtt ctgcagaatg gatctgtttc tcaagtatcc    1140

agatggatca cgagcagcag cagcaacctt caacctggaa cgaatctcaa tgtaacagac    1200

aatcattttt gggcgcatct tccggctcag agtgtgacaa catttgtcgc taacctccgc    1260

taa                                                                  1263


<210> SEQ ID NO 36
<211> LENGTH: 496
<212> TYPE: PRT
<213> ORGANISM: Paenibacillus sp.
<220> FEATURE:
<221> NAME/KEY: mat_peptide
<222> LOCATION: (28)..(496)
```

<400> SEQUENCE: 36

```
Met Ala Thr Lys Pro Thr Ala Val Leu Asn Ala Asp Leu Thr Thr Gly
        -25                 -20                 -15

Thr Ile Asn Arg Asn Ile Tyr Gly His Phe Ala Glu His Leu Gly Arg
    -10                 -5                  -1  1               5

Cys Ile Tyr Glu Gly Leu Trp Val Gly Asp Asn Pro Glu Ile Gln Asn
                10                  15                  20

Thr Gly Gly Ile Arg Asn Asp Val Leu Glu Ala Leu Arg Asn Leu Asn
            25                  30                  35

Ile Pro Val Leu Arg Trp Pro Gly Gly Cys Phe Ala Asp Glu Tyr His
        40                  45                  50

Trp Lys Asp Gly Val Gly Pro Val Glu Ser Arg Lys Arg Met Val Asn
    55                  60                  65

Thr His Trp Gly Cys Val Val Glu Asp Asn Ser Phe Gly Thr His Glu
70                  75                  80                  85

Tyr Met His Leu Val Glu Leu Leu Gly Cys Glu Pro Tyr Ile Asn Gly
                90                  95                  100

Asn Val Gly Ser Gly Thr Val Gln Glu Met Ser Glu Trp Val Glu Tyr
            105                 110                 115

Ile Thr Phe Glu Gly Glu Ser Pro Met Ala Asn Trp Arg Arg Glu Asn
        120                 125                 130

Gly Arg Glu Lys Pro Trp Lys Leu Lys Tyr Phe Gly Val Gly Asn Glu
    135                 140                 145

Ser Trp Gly Cys Gly Gly Asn Met Arg Pro Glu Tyr Tyr Ala Asp Leu
150                 155                 160                 165

Tyr Arg Gln Phe Gln Thr Tyr Val Arg Asn Tyr Gly Asp Asn Lys Ile
                170                 175                 180

Tyr Arg Ile Ala Cys Gly Ala Asn Val Asp Asp Tyr Arg Trp Thr Glu
            185                 190                 195

Val Leu Met Glu Arg Ala Gly Asn His Met Asp Gly Leu Ser Leu His
        200                 205                 210

Tyr Tyr Thr Tyr Pro Gly Leu Trp Glu Asp Glu Lys Lys Pro Ala Leu
    215                 220                 225

Gln Phe Asp Glu Gly Ile Trp Phe Glu Thr Met Phe Lys Ala Tyr Phe
230                 235                 240                 245

Met Asp Glu Leu Ile Thr Arg His Ser Lys Val Met Asp Lys Phe Asp
                250                 255                 260

Pro Lys Lys Arg Val Gly Ile Ile Leu Asp Glu Trp Gly Thr Trp Phe
            265                 270                 275

Gly Val Glu Pro Gly Thr Asn Pro Gly Phe Leu Tyr Gln Gln Ser Thr
        280                 285                 290

Met Arg Asp Ala Leu Val Ala Gly Leu His Phe Asn Ile Phe His Asn
    295                 300                 305

His Asn Asp Arg Leu His Met Ala Asn Ile Ala Gln Thr Ile Asn Val
310                 315                 320                 325

Leu Gln Ala Val Ala Leu Thr Asp Gly Pro Arg Met Leu Leu Thr Pro
                330                 335                 340

Thr Tyr His Val Phe Glu Met Tyr Lys Val His Gln Asp Ala Gln Gln
            345                 350                 355

Val Gln Leu Asn Tyr Asp Ser Pro Val Tyr Glu Met Asp Gly Arg Ser
        360                 365                 370

Ile Asn Gln Val Ser Met Thr Ala Ser Lys Ala Ala Asp Gly Thr Ile
    375                 380                 385
```

```
Asn Leu Gly Leu Cys Asn Val His His Ala Asp Ala Val Ser Ile Ser
390                 395                 400                 405

Ile Glu Leu Arg Gly Gln Thr Phe Ser Ser Ile Glu Gly Arg Val Leu
                410                 415                 420

Thr Ser Ala Glu Leu Arg Asp Cys Asn Thr Phe Asp Asn Pro Asp Val
            425                 430                 435

Val Lys Pro Val Pro Phe Thr Ala Phe Thr Ile Glu Asp Gly Val Leu
        440                 445                 450

Arg Leu Asp Leu Pro Ala Arg Ser Val Thr Ser Leu Ala Leu Lys Ala
    455                 460                 465
```

<210> SEQ ID NO 37
<211> LENGTH: 1491
<212> TYPE: DNA
<213> ORGANISM: Paenibacillus sp.

<400> SEQUENCE: 37

```
atggcaacga agcctactgc tgtactgaac gctgatctga cgaccggtac aattaaccgt      60

aacatctacg gccatttcgc cgagcatctc ggccgctgca tatatgaagg cttgtgggtt     120

ggcgacaatc ccgaaattca gaacacaggc ggtatccgca acgacgtatt ggaagcgctt     180

cgcaacttga acattcctgt tctgcgttgg ccaggcggct gcttcgccga cgagtaccac     240

tggaaagacg gcgtaggtcc tgttgaatcg cgcaaacgca tggtcaatac gcactggggc     300

tgcgtagtgg aagataacag ctttggtacg catgaatata tgcaccttgt tgaactgctc     360

ggctgcgagc cttacatcaa cggcaacgtg ggcagcggca ccgttcaaga gatgtccgaa     420

tgggttgaat acataacgtt cgaaggcgaa tcgccaatgg cgaactggcg ccgcgagaac     480

ggtcgcgaga agccttggaa gctcaaatat ttcggtgtag gcaacgaaag ctggggctgc     540

ggcggcaaca tgcgtcctga atactatgcc gacttgtacc gccaattcca gacgtatgtc     600

cgcaactatg gcgacaacaa aatctaccgc atcgcatgcg gcgctaacgt ggacgactac     660

cgctggacgg aagtgctcat ggagcgcgct ggcaatcaca tggacggcct gagcctccac     720

tattatacgt accctggtct gtgggaagat gagaagaagc ctgcgctgca gttcgacgag     780

ggcatctggt tcgagacgat gttcaaagcg tacttcatgg acgagctcat cacgcgtcac     840

tccaaagtga tggacaaatt cgatccgaag aaacgcgtcg gcatcatcct tgacgagtgg     900

ggcacttggt tcggcgtaga gccgggcacg aacccaggct tcctgtatca gcaaagcacg     960

atgcgcgacg cgcttgtcgc gggtctgcac tttaacattt tccacaacca taacgatcgt    1020

ctccacatgg cgaacatcgc gcagacgatt aacgtcctgc aagcggtagc gctgacggac    1080

ggtcctcgta tgctgctcac gccaacgtac catgtattcg agatgtacaa ggtgcaccaa    1140

gacgcgcagc aggttcaact gaactatgac agccctgtgt acgaaatgga cggccgctcg    1200

atcaaccaag tgagcatgac ggcttccaaa gcagcagacg gcacgatcaa cctcggcctc    1260

tgtaacgttc accacgccga tgcggtgagc atcagcatcg agctgcgcgg tcaaacgttc    1320

tcttcgatcg aaggtcgtgt gctgacgagc gctgagctgc gcgactgcaa cacgttcgac    1380

aatccggacg ttgtgaagcc agtgccgttc acggcattca cgatcgaaga cggtgtactc    1440

cgcctcgacc tgcctgcacg ctcggttaca tcgctcgcac tgaaagctta a             1491
```

<210> SEQ ID NO 38
<211> LENGTH: 34
<212> TYPE: DNA
<213> ORGANISM: Artificial Sequence -continued

```
<220> FEATURE:
<223> OTHER INFORMATION: primer

<400> SEQUENCE: 38

aaggagatat acatatggca acgaagccta ctgc                              34


<210> SEQ ID NO 39
<211> LENGTH: 36
<212> TYPE: DNA
<213> ORGANISM: Artificial Sequence
<220> FEATURE:
<223> OTHER INFORMATION: primer

<400> SEQUENCE: 39

ggtggtggtg ctcgagagct ttcagtgcga gcgatg                            36
```